United States Patent
Berry et al.

(10) Patent No.: US 10,563,163 B2
(45) Date of Patent: Feb. 18, 2020

(54) CROSS-SCALE MODELING OF BIOREACTOR CULTURES USING RAMAN SPECTROSCOPY

(71) Applicant: Biogen MA Inc., Cambridge, MA (US)

(72) Inventors: Brandon Berry, Boston, MA (US); Justin Moretto, Apex, NC (US)

(73) Assignee: Biogen MA Inc., Cambridge, MA (US)

( * ) Notice: Subject to any disclaimer, the term of this patent is extended or adjusted under 35 U.S.C. 154(b) by 335 days.

(21) Appl. No.: 15/322,560

(22) PCT Filed: Jul. 2, 2015

(86) PCT No.: PCT/US2015/039011
§ 371 (c)(1),
(2) Date: Dec. 28, 2016

(87) PCT Pub. No.: WO2016/004322
PCT Pub. Date: Jan. 7, 2016

(65) Prior Publication Data
US 2017/0130186 A1    May 11, 2017
US 2017/0355947 A9    Dec. 14, 2017

Related U.S. Application Data

(60) Provisional application No. 62/020,371, filed on Jul. 2, 2014.

(51) Int. Cl.
C12M 1/34    (2006.01)
C12M 1/36    (2006.01)
G01N 21/65   (2006.01)

(52) U.S. Cl.
CPC ............ *C12M 41/32* (2013.01); *C12M 41/48* (2013.01); *G01N 21/65* (2013.01); *G01N 2201/12* (2013.01)

(58) Field of Classification Search
None
See application file for complete search history.

(56) References Cited

U.S. PATENT DOCUMENTS

| | | |
|---|---|---|
| 5,243,983 A | 9/1993 | Taff et al. |
| 6,350,367 B1 | 2/2002 | West |
| 7,521,203 B2 | 4/2009 | Lin et al. |
| 8,224,415 B2 | 7/2012 | Budiman |
| 9,506,867 B2 | 11/2016 | Moretto et al. |
| 2001/0034478 A1 | 10/2001 | Lambert et al. |
| 2004/0180379 A1 | 9/2004 | Van Dunye et al. |
| 2004/0204634 A1 | 10/2004 | Womble et al. |
| 2005/0089993 A1 | 4/2005 | Boccazzi et al. |
| 2006/0281068 A1 | 12/2006 | Maier et al. |
| 2008/0299539 A1 | 12/2008 | Lee et al. |
| 2009/0023804 A1 | 1/2009 | Baugh et al. |
| 2009/0046284 A1 | 2/2009 | Wang et al. |
| 2009/0063101 A1 | 3/2009 | Yeshwantpur et al. |
| 2009/0104594 A1 | 4/2009 | Webb |
| 2009/0134043 A1 | 5/2009 | Ward et al. |
| 2009/0312851 A1 | 12/2009 | Mishra |
| 2010/0114514 A1 | 5/2010 | Wang et al. |
| 2010/0256336 A1 | 10/2010 | Yuk et al. |
| 2012/0123688 A1 | 5/2012 | Ramasubramanyan et al. |
| 2012/0229796 A1 | 9/2012 | Priore |
| 2012/0316446 A1 | 12/2012 | Vukelic et al. |
| 2013/0161191 A1 | 6/2013 | Wilhelm et al. |
| 2013/0189723 A1 | 7/2013 | Felder et al. |
| 2013/0286380 A1 | 10/2013 | Selker et al. |
| 2014/0185033 A1 | 7/2014 | Moretto et al. |
| 2016/0025633 A1 | 1/2016 | Moretto et al. |
| 2017/0276659 A1 | 9/2017 | Turyan et al. |
| 2018/0291329 A1 | 10/2018 | Moretto et al. |

FOREIGN PATENT DOCUMENTS

| | | |
|---|---|---|
| WO | WO 1997/014430 A | 4/1997 |
| WO | WO 1998/041611 A1 | 9/1998 |
| WO | WO 2002/033388 A1 | 4/2002 |
| WO | WO 2004/104186 A1 | 12/2004 |
| WO | WO 2012/059748 A1 | 5/2012 |
| WO | WO 2014/144999 A1 | 9/2014 |
| WO | WO 2016/004322 A2 | 1/2016 |

OTHER PUBLICATIONS

Abu-Absi, Nicholas R., et al. "Real time monitoring of multiple parameters in mammalian cell culture bioreactors using an in-line Raman spectroscopy probe." Biotechnology and bioengineering 108.5 (2011): 1215-1221.*

Abu-Absi et al., Real time monitoring of multiple parameters in mammalian cell culture bioreactors using an in-line Raman spectroscopy probe. Biotechnol Bioeng. May 2011;108(5):1215-21. doi: 10.1002/bit.23023. Epub Dec. 22, 2010.

Berry et al., Cross-scale predictive modeling of CHO cell culture growth and metabolites using Raman spectroscopy and multivariate analysis. Biotechnol Prog. Mar.-Apr. 2015;31(2):566-77. doi:10.1002/btpr.2035. Epub Dec. 29, 2014.

Chen et al., Effects of elevated ammonium on glycosylation gene expression in CHO cells. Metab Eng. Mar. 2006;8(2):123-32. Epub Dec. 27, 2005.

Cline et al., Anomalously Slow Electron Transfer at Ordered Graphite Electrodes: Influence of Electronic Factors and Reactive Sites. J. Phys. Chem. 1994;98(2):5314-5319.

Houde et al., Determination of protein oxidation by mass spectrometry and method transfer to quality control. J Chromatogr A. Aug. 11, 2006;1123(2):189-98. Epub May 22, 2006.

Jackson et al., Surface-enhanced Raman scattering on tunable plasmonic, nanoparticle substrates. PNAS. Dec. 28, 2004;101(52):17930-17935.

Jia et al., Label-free fluorometric assay for acetylcholinesterase and inhibitor screening based on supramolecular assemblies. Anal Methods. 2013;5:5431-5436.

(Continued)

*Primary Examiner* — G Steven Vanni
(74) *Attorney, Agent, or Firm* — Wolf, Greenfield & Sacks, P.C.

(57) ABSTRACT

Aspect of the disclosure relate to methods of assessing a bioreactor culture that involve determining a culture parameter of the manufacturing-scale bioreactor culture using a model that relates a Raman spectrum to the culture parameter. Related bioreactor system are also provided.

21 Claims, 23 Drawing Sheets

(56) References Cited

OTHER PUBLICATIONS

Lee et al., Characterization of raw material influence on mammalian cell culture performance: chemometrics based data fusion approach. Accessed via http://focapo.cheme.cmu.edu/2012/proceedings/data/papers/085.pdf on Dec. 12, 2011. 6 pages.
Lee et al., Data fusion-based assessment of raw materials in mammalian cell culture. Biotechnol Bioeng. Nov. 2012;109(11):2819-28. doi: 10.1002/bit.24548, Epub May 28, 2012.
Li et al., Rapid characterization and quality control of complex cell culture media solution using raman spectroscopy and chemometrics. Biotechnol Bioeng. Oct. 1, 2010;107(2):290-301. doi: 10.1002/bit.22813.
Li et al., Using surface-enhanced Raman scattering (SERS) and fluorescence spectroscopy for screening yeast extracts, a complex component of cell culture media. J. Raman Spectroscopy. 2012;43(8):1074-1082. doi: 10.1002/jrs.3141. Supplemental information.
Martens et al., Extended multiplicative signal correction and spectral interference subtraction: new preprocessing methods for near infrared spectroscopy. J Pharm Biomed Anal. 1991;9(8):625-35.
Molloy et al., Human furin is a calcium-dependent serine endoprotease that recognizes the sequence Arg-X-X-Arg and efficiently cleaves anthrax toxin protective antigen. J Biol Chem. Aug. 15, 1992;267(23):16396-402.
Moretto et al., Process Raman Spectroscopy for In-Line CHO Cell Culture Monitoring. Apr. 2011. American Pharmaceutical Review.
Mungikar et al., Use of In-line Raman Spectroscopy as a Nondestructive and Rapid Analytical Technique to Monitor Aggregation of a Therapeutic Protein. Nov. 2010. American Pharmaceutical Review.
Raman et al., A New Type of Secondary Radiation. Nature. Mar. 1928;121:501-502.
Rodrigues et al., Assessment of enamel chemistry composition and its relationship with caries susceptibility. Proceedings SPIE. 2005;5687:132-139.
Ryan et al., Prediction of cell culture media performance using fluorescence spectroscopy. Anal Chem. Feb. 15, 2010;82(4):1311-7. doi: 10.1021/ac902337c.
Seli et al., Noninvasive metabolomic profiling of embryo culture media using Raman and near-infrared spectroscopy correlates with reproductive potential of embryos in women undergoing in vitro fertilization. Fertil Steril. Nov. 2007;88(5):1350-7. Epub Oct. 17, 2007.
Shen et al., Accurate and noninvasive embryos screening during in vitro fertilization (IVF) assisted by Raman analysis ofembryos culture medium. Laser Physics Letters. 2012;9(4):322-328.
Thomson et al., Resurrecting ancestral alcohol dehydrogenases from yeast. Nat Genet. Jun. 2005;37(6):630-5. Epub May 1, 2005.
Wen et al., Application of Raman Spectroscopy in Biopharmaceutical Manufacturing. Raman. Jun. 2010. 46-53.
Witjes et al., Automatic correction of peak shifts in Raman spectra before PLS regression. Chemo. Intell. Lab. Systems. Aug. 2000;52(1):105-116.
Invitation to Pay Additional Fees for Application No. PCT/US2016/034717 dated Sep. 5, 2016.
International Search Report and Written Opinion for Application No. PCT/US2016/034717 dated Nov. 18, 2016.
International Preliminary Report on Patentability for Application No. PCT/US2016/034717 dated Dec. 14, 2017.
Supplementary European Search Report for Application No. EP 15815514.3 dated Feb. 20, 2018.
Partial Supplementary European Search Report for Application No. EP 15838214.3 dated Jun. 8, 2018.
Supplementary European Search Report for Application No. 15838214.3 dated Sep. 19, 2018.
Al-Jabri et al., Second derivative differential electrolytic potentiometry for oxidation—reduction reactions. Journal of Chemical and Pharmaceutical Research. 2001;4(4):2180-2187.
Ashton et al., The challenge of applying Raman spectroscopy to monitor recombinant antibody production. Analyst. Nov. 21, 2013;138(22):6977-85. doi:10.1039/c3an01341c.
Chang et al., Multi-stage continuous high cell density culture systems: a review. Biotechnol Adv. Mar.-Apr. 2014;32(2):514-25. doi: 10.1016/j.biotechadv.2014.01.004. Epub Jan. 21, 2014.
Chen et al., A new approach to near-infrared spectral data analysis using independent component analysis. J Chem Inf Comput Sci. Jul.-Aug. 2001;41(4):992-1001.
Collins et al., Indirect procedure for the determination of Tin(II) by potentiometric titration. Analytical Chemistry. Oct. 1962;34(11):1511-1513.
Gorfien et al., Optimized Nutrient Additives for fed-batch cultures. BioPharm International. Apr. 2003. 34-40.
Harris, Quantitative Chemical Analaysis. 7th edition. 2007 W.H. Freeman and Company. pp. 299, 300, 327-331.
Kowalsky, Technetium Radiopharmaceutical Chemistry, Continuing Education for Nuclear Pharmacists and Nuclear Medicine Professionals. vol. 12, Lesson 3. 2006. The University of New Mexico Health Sciences Center College of Pharmacy. 77 pages.
Kowalsky et al., Re: Stability of stannous ion in stannous pyrophosphate kits. J Nucl Med. Nov. 1983;24(11):1080-1.
Li et al., Performance monitoring of mammalian cell based bioprocess using Raman spectroscopy. Analytica Chimica Acta. Aug. 6, 2013;796:84-91.
Matthews et al., Closed loop control of lactate concentration in mammalian cell culture by Raman spectroscopy leads to improved cell density, viability, and biopharmaceutical protein production. Biotechnol Bioeng. Nov. 2016;113(11):2416-24. doi: 10.1002/bit.26018. Epub Jun. 9, 2016.
Milligan et al., Semisynthetic model calibration for monitoring glucose in mammalian cell culture with in situ near infrared spectroscopy. Biotechnol Bioeng. May 2014;111(5):896-903. doi:10.1002/bit.25161. Epub Dec. 17, 2013.
Ozturk et al., Real-time monitoring and control of glucose and lactate concentrations in a mammalian cell perfusion reactor. Biotechnol Bioeng. Feb. 20, 1997;53(4):372-8.
Ponte, Special safety considerations in preparation of technetium Tc-99m DTPA for cerebrospinal fluid-related imaging procedures. J Am Pharm Assoc (2003). May-Jun. 2008;48(3):413-6. doi: 10.1331/JAPhA.2008.07038.
Vanlić-Razumenić et al., Oxidation states of technetium in diphosphonate complexes. D. Journal of Radioanalytical and Nuclear Chemistry, Articles. 1995;190(1):149-154.
Whelan et al., In Situ Raman Spectroscopy for Simultaneous Monitoring of Multiple Process Parameters in Mammalian Cell Culture Bioreactors. Biotechnology Progress. Jul. 20, 2012;28(5):1355-1362.
Yuk et al., Controlling glycation of recombinant antibody in fed-batch cell cultures. Biotechnol Bioeng. Nov. 2011;108(11):2600-10. doi:10.1002/bit.23218. Epub Jun. 15, 2011.

* cited by examiner or# CROSS-SCALE MODELING OF BIOREACTOR CULTURES USING RAMAN SPECTROSCOPY

RELATED APPLICATIONS

This application is a national stage filing under 35 U.S.C. § 371 of International Application No. PCT/US2015/039011, filed Jul. 2, 2015, which claims the benefit under 35 U.S.C. § 119(e) of U.S. Provisional Application No. 62/020,371, entitled "CROSS-SCALE MODELING OF BIOREACTOR CULTURES USING RAMAN SPECTROSCOPY," filed Jul. 2, 2014, the contents of which are hereby incorporated herein by reference in their entirety.

BACKGROUND OF INVENTION

In recent years the United States Food and Drug Administration (FDA) and the European Medicines Agency (EMEA) have emphasized a desire to see greater control and process understanding in the area of pharmaceutical development, manufacturing and quality assurance which is collectively referred to as process analytical technology (PAT). Likewise, bioprocessing and specifically cell culture application users are interested in attaining more advanced, informative and significant real-time data out of their systems to drive process development and manufacturing success while also ushering in a generation of advanced process control (APC).

While the real-time monitoring of pH, dissolved oxygen (DO), dissolved CO2 and temperature are relevant to cell culture applications and have been typical online monitoring and control parameters within cell culture and bioprocessing applications for decades, there are also other process parameters that involve manual bioreactor sampling and offline analysis. These parameters may include total cell density (TCD) and, viable cell density (TCD), protein production and cell metabolism components including amino acids, growth nutrients, and cell waste products. A need exists to transfer the monitoring of these traditionally offline measured parameters towards an in situ application which will create the potential for real-time control. Driving this transition to PAT and APC while also meeting the guidance provided in the regulatory framework poses specific challenges for the development, manufacturing and quality assurance of biologics due to the multivariate nature of the environments required for synthesizing these complex protein structures.

SUMMARY OF INVENTION

Aspects of the disclosure relate to methods of monitoring and/or assessing bioreactor cultures using Raman spectroscopy. In particular, methods are provided for assessing culture parameters (e.g., the level of a component of a bioreactor culture) using scale independent multivariate models developed based on Raman spectral data obtained from bioreactor cultures of one or more different scales. In some embodiments, methods provided herein involve multivariate models based on Raman spectral data obtained at test-scales (e.g., bench and/or pilot-scales) that are accurate at larger manufacturing-scale (e.g., 1000 L or greater) settings. Thus, in some embodiments, multivariate models provided herein have the ability to predict process performance in commercial manufacturing based on data from scaled down bioreactor models. Smaller development scale test reactors, which may include bench-scale and/or pilot-scale reactors, are advantageous because they allow more parameters to be tested for a given cost. However, in some embodiments, methods provided herein involve multivariate models based on Raman spectral data obtained across multiple different scales of bioreactor cultures, including, for example, bench and/or pilot-scales, that are accurate across a range of scales, including manufacturing-scales. In some embodiments, by gathering data at bench, pilot and/or manufacturing-scales, models incorporate tremendous process variability, offering a great deal of robustness to the final model.

Accordingly, aspects of the disclosure relate to methods of monitoring and/or assessing a bioreactor culture. In some embodiments, the methods involve (i) obtaining a Raman spectrum of a manufacturing-scale bioreactor culture; and (ii) determining a culture parameter of the manufacturing-scale bioreactor culture using a model that relates the Raman spectrum to the culture parameter, in which the model is developed based on one or more test bioreactor cultures of a smaller volume than the manufacturing-scale bioreactor culture. In some embodiments, the volume of the manufacturing-scale bioreactor culture is in a range of 1000 L to 4000 L. In some embodiments, the volume of the test bioreactor culture is in a range of 1 L to 400 L. In some embodiments, the test bioreactor culture is a bench-scale bioreactor culture. In some embodiments, the bench-scale bioreactor culture is in a range of 1 L to 5 L. In some embodiments, the test bioreactor culture is a pilot-scale bioreactor culture. In some embodiments, the pilot-scale bioreactor culture is in a range of 50 L to 100 L.

In some embodiments of the methods, the model is a multivariate model, such as a partial least squares model. In some embodiments, the culture parameter is a level of glucose, glutamate, ammonia or lactate in the culture. In some embodiments, the culture parameter is a level of glucose, and the model has: (i) a root mean square error of estimation in a range of 0.50 g/L to 1 g/L, and/or (ii) a root mean square error of cross validation in a range of 0.50 g/L to 1 g/L, and/or (iii) a root mean square error of prediction in a range of 0.50 g/L to 1.5 g/L, and/or (iv) an average percentage error of up to 10%. In some embodiments, the culture parameter is a level of lactate, and the model has: (i) a root mean square error of estimation in a range of 0.10 g/L to 0.20 g/L, and/or (ii) a root mean square error of cross validation in a range of 0.10 g/L to 0.20 g/L, and/or (iii) a root mean square error of prediction in a range of 0.10 g/L to 0.20 g/L, and/or (iv) an average percentage error of up to 20%. In some embodiments, the culture parameter is a level of glutamate, and the model has: (i) a root mean square error of estimation in a range of 0.10 mM to 0.20 mM, and/or (ii) a root mean square error of cross validation in a range of 0.10 mM to 0.40 mM, and/or (iii) a root mean square error of prediction in a range of 0.40 mM to 1.5 mM, and/or (iv) an average percentage error of up to 35%. In some embodiments, the culture parameter is a level of ammonium, and the model has: (i) a root mean square error of estimation in a range of 0.20 mM to 0.40 mM, and/or (ii) a root mean square error of cross validation in a range of 0.20 mM to 0.50 mM, and/or (iii) a root mean square error of prediction in a range of 0.40 mM to 1.5 mM, and/or (iv) an average percentage error of up to 20%.

In some embodiments of the methods, the culture parameter is the osmolality of the culture. In some embodiments, the culture parameter is the osmolality of the culture and the model has: (i) a root mean square error of estimation in a range of 5 mOsm/kg to 15 mOsm/kg, and/or (ii) a root mean square error of cross validation in a range of 10 mOsm/kg to 15 mOsm/kg, and/or (iii) a root mean square error of prediction in a range of 10 mOsm/kg to 25 mOsm/kg, and/or (iv) an average percentage error of up to 10%.

In some embodiments, methods provided herein of monitoring and/or assessing a bioreactor culture involve (i) obtaining a Raman spectrum of a first bioreactor culture of a first volume; and (ii) determining a culture parameter of the first bioreactor culture using a model, developed based on a second bioreactor culture of a second volume, that relates the Raman spectrum to the culture parameter. In some embodiments, the second volume is in a range of 0.0005% to 90% or 0.0005% to 50% of first volume. In some embodiments, the second volume is in a range of 0.1% to 10% of first volume.

In some embodiments, methods provided herein of monitoring and/or assessing a bioreactor culture involve (i) obtaining a Raman spectrum of a manufacturing-scale bioreactor culture and (ii) determining a culture parameter of the manufacturing-scale bioreactor culture using a model that relates the Raman spectrum to the culture parameter, wherein the model is developed based on at least one bioreactor culture of a smaller volume than the manufacturing-scale bioreactor culture and at least one bioreactor culture of substantially the same volume as the manufacturing-scale bioreactor culture. In some embodiments, the manufacturing-scale bioreactor culture is in a range of 1000 L to 4000 L. In some embodiments, the at least one bioreactor culture of a smaller volume than the manufacturing-scale bioreactor culture is in a range of 1 L to 100 L.

In some embodiments of methods disclosed herein, a Raman spectrum comprises spectral signal in the 200 cm$^{-1}$ to 3400 cm$^{-1}$ wavenumber range. In some embodiments, a Raman spectrum comprises spectral signal in the visible, near infrared, infrared, near ultraviolet, or ultraviolet (UV) range. In some embodiments, a Raman spectrum is obtained using Surface Enhanced Raman Spectroscopy (SERS), resonance Raman spectroscopy, tip-enhanced Raman spectroscopy, polarized Raman spectroscopy, stimulated Raman spectroscopy, transmission Raman spectroscopy, spatially offset Raman spectroscopy, difference Raman spectroscopy, Fourier Transform (FT) Raman, or hyper Raman spectroscopy. In some embodiments, a Raman spectrum is obtained using a Raman analyzer configured with a laser or other suitable light source that operates at wavelengths in a range of 325 nm to 1064 nm.

Aspects of the disclosure relate to bioreactor systems. In some embodiments, the bioreactor systems comprise: a bioreactor chamber configured for containing a bioreactor culture (e.g., a manufacturing-scale bioreactor culture) and a probe configured for obtaining a Raman spectrum of the bioreactor culture. In some embodiments, bioreactor systems disclosed herein further comprises a computer configured for determining a culture parameter of a bioreactor culture (e.g., a manufacturing-scale bioreactor culture). In some embodiments, a computer of a bioreactor system comprises an input interface configured to receive information indicative of a Raman spectrum obtained from the probe. In some embodiments, a computer of a bioreactor system further comprises at least one processor programmed to evaluate a model that relates a Raman spectrum (e.g., obtained from a Raman probe) to a culture parameter. In some embodiments, the model is developed based on one or more test bioreactor cultures of a smaller volume than the manufacturing-scale bioreactor culture. In some embodiments, a computer further comprises an output interface configured to output a signal indicative of the determined culture parameter. In some embodiments, the output comprises a feedback control signal for controlling operation of a device for altering the culture parameter. In some embodiments, the device for altering the culture parameter is a pump or valve that controls flow, into or out from the bioreactor culture, of a medium comprising one or more culture components.

Aspects of the disclosure relate to bioreactor systems that comprises: a bioreactor chamber configured for containing a manufacturing-scale bioreactor culture; a probe configured for obtaining a Raman spectrum of the manufacturing-scale bioreactor culture; and a computer configured for determining a culture parameter of the manufacturing-scale bioreactor culture, in which the computer comprises: an input interface configured to receive information indicative of the Raman spectrum obtained from the probe; at least one processor programmed to evaluate a model that relates the Raman spectrum to the culture parameter, in which the model is developed based on at least one bioreactor culture of a smaller volume than the manufacturing-scale bioreactor culture and at least one bioreactor culture of substantially the same volume as the manufacturing-scale bioreactor culture an output interface configured to output a signal indicative of the determined culture parameter.

In some embodiments of bioreactor systems disclosed herein, the volume of the manufacturing-scale bioreactor culture is in a range of 1000 L to 4000 L. In some embodiments, the volume of the test bioreactor culture is in a range of 1 L to 400 L. In some embodiments, the test bioreactor culture is a bench-scale bioreactor culture. In some embodiments, the bench-scale bioreactor culture is in a range of 1 L to 5 L. In some embodiments, the test bioreactor culture is a pilot-scale bioreactor culture. In some embodiments, the pilot-scale bioreactor culture is in a range of 50 L to 100 L. In some embodiments, the model is a multivariate model, such as a partial least squares model. In some embodiments, the culture parameter is a level of glucose, glutamate, ammonia or lactate in the culture. In some embodiments, the culture parameter is a level of glucose, and the model has: (i) a root mean square error of estimation in a range of 0.50 g/L to 1 g/L, and/or (ii) a root mean square error of cross validation in a range of 0.50 g/L to 1 g/L, and/or (iii) a root mean square error of prediction in a range of 0.50 g/L to 1.5 g/L, and/or (iv) an average percentage error of up to 10%. In some embodiments, the culture parameter is a level of lactate, and the model has: (i) a root mean square error of estimation in a range of 0.10 g/L to 0.20 g/L, and/or (ii) a root mean square error of cross validation in a range of 0.10 g/L to 0.20 g/L, and/or (iii) a root mean square error of prediction in a range of 0.10 g/L to 0.20 g/L, and/or (iv) an average percentage error of up to 20%. In some embodiments, the culture parameter is a level of glutamate, and the model has (i) a root mean square error of estimation in a range of 0.10 mM to 0.20 mM, and/or (ii) a root mean square error of cross validation in a range of 0.10 mM to 0.40 mM, and/or (iii) a root mean square error of prediction in a range of 0.40 mM to 1.5 mM, and/or (iv) an average percentage error of up to 35%. In some embodiments, the culture parameter is a level of ammonium, and the model has: (i) a root mean square error of estimation in a range of 0.20 mM to 0.40 mM, and/or (ii) a root mean square error of cross validation in a range of 0.20 mM to 0.50 mM, and/or (iii) a root mean square error of prediction in a range of 0.40 mM to 1.5 mM, and/or (iv) an average percentage error of up to 20%. In some embodiments, the culture parameter is the osmolality of the culture. In some embodiments, the culture parameter is the osmolality of the culture and the model has: (i) a root mean square error of estimation in a range of 5 mOsm/kg to 15 mOsm/kg, and/or (ii) a root mean square error of cross validation in a range of 10 mOsm/kg to 15 mOsm/kg, and/or (iii) a root mean square error of prediction in a range of 10 mOsm/kg to 25 mOsm/kg, and/or (iv) an average percentage error of up to 10%.

In some embodiments of the bioreactor systems disclosed herein, a Raman spectrum comprises spectral signal in the visible, near infrared, infrared, near ultraviolet, or ultraviolet (UV) range. In some embodiments, the Raman spectrum is obtained using Surface Enhanced Raman Spectroscopy (SERS), resonance Raman spectroscopy, tip-enhanced Raman spectroscopy, polarized Raman spectroscopy, stimulated Raman spectroscopy, transmission Raman spectroscopy, spatially offset Raman spectroscopy, difference Raman spectroscopy, Fourier Transform (FT) Fourier Transform (FT) Raman, or hyper Raman spectroscopy. In some embodiments, the probe comprises a Raman analyzer configured with a laser or other suitable light source that operates at wavelengths in a range of 325 nm to 1064 nm.

DETAILED DESCRIPTION OF INVENTION

Figure 1:
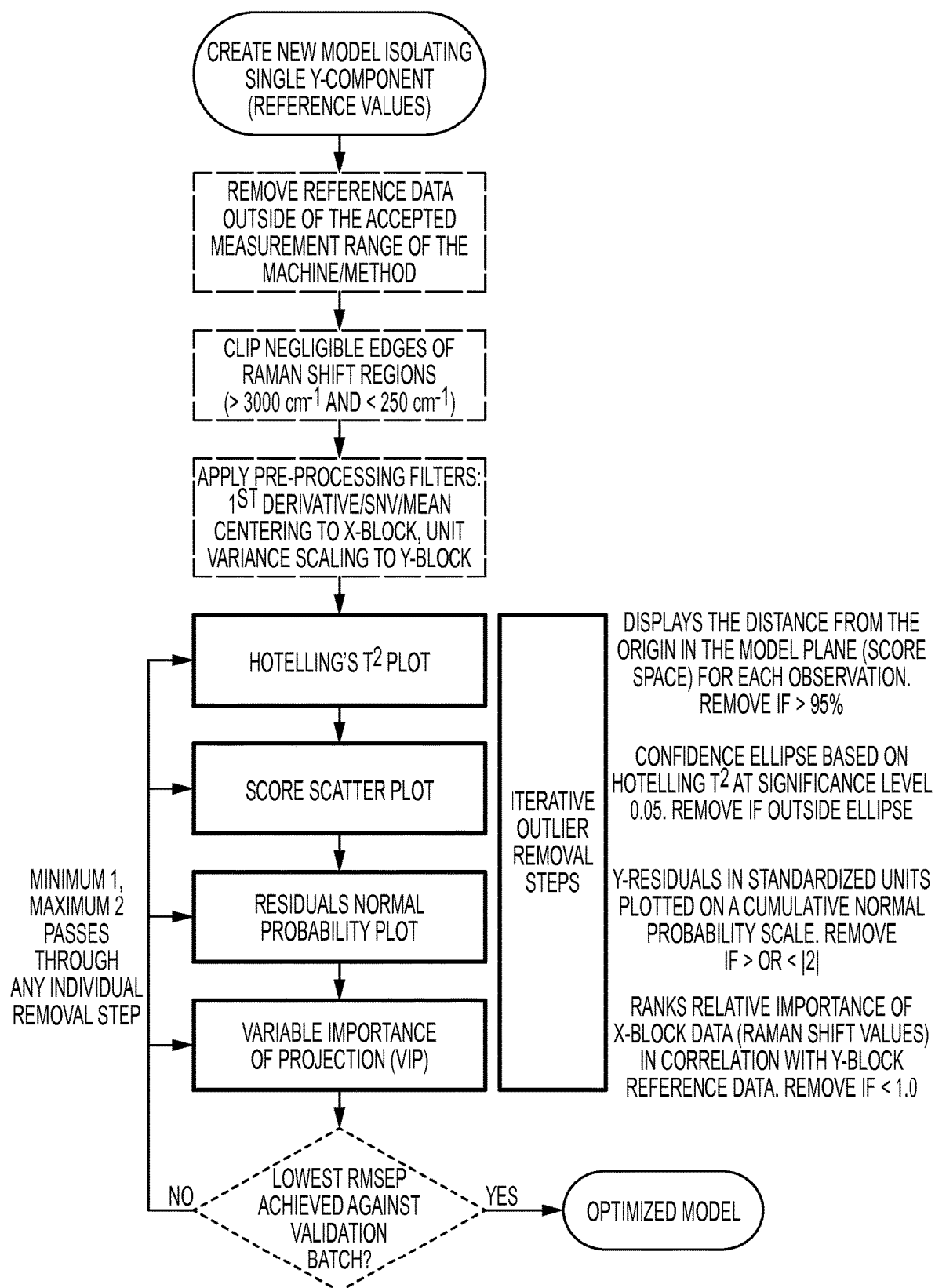
FIG. 1 is a non-limiting example of a process flow diagram for data preprocessing, multivariate model building, optimization, and selection criteria of PLS models.

Aspects of the disclosure relate to methods of monitoring and/or assessing bioreactor cultures using Raman spectroscopy. In particular, methods are provided for assessing culture parameters (e.g., the level of a component of a bioreactor culture) using scale independent multivariate models developed based on Raman spectral data. In some embodiments, methods provided herein involve multivariate models based on Raman spectral data obtained at one or more different scales that are accurate at larger manufacturing-scale (e.g., 1000 L or greater) settings. In some embodiments, methods provided herein involve obtaining a Raman spectrum of a first bioreactor culture of a first volume (e.g., a manufacturing-scale) and determining a culture parameter of the first bioreactor culture using a model, developed based on a second bioreactor culture of a second volume (e.g., a bench or pilot-scale), that relates the Raman spectrum to the culture parameter, wherein the second volume is smaller than the first volume. For example, the second volume may be the volume of a developmental scale bioreactor, such as a laboratory (e.g., bench top scale bioreactor) or a pilot-scale bioreactor. In some embodiments, the second volume is in a range of 0.0005% to 50% of first volume. In some embodiments, methods provided herein involve obtaining a Raman spectrum of a manufacturing-scale bioreactor culture and determining a culture parameter of the manufacturing-scale bioreactor culture using a model that relates the Raman spectrum to the culture parameter, in which the model is developed based on one or more test bioreactor cultures of a smaller volume than the manufacturing-scale bioreactor culture.

Bioreactor Cultures and Components Thereof

Generally, a bioreactor refers to an engineered device that supports or is capable of supporting cell culture, e.g., for the production of a therapeutic agent by cells of the culture. For example, a bioreactor may comprise a vessel in which a chemical process is carried out that involves organisms, cells or biochemically active substances derived from such organisms. While many bioreactors are made primarily of corrosion resistant alloys, such as stainless steel (e.g., grade-316 L stainless steel), it should be appreciated that a bioreactor may be made of glass, ceramics, plastic, or any number of materials or combinations thereof.

The term "manufacturing-scale bioreactor culture" refers to a bioreactor culture of scale sufficient to produce commercial or production scale quantities of a molecule (e.g., a therapeutic protein, e.g., a therapeutic antibody). In some embodiments, a manufacturing-scale bioreactor culture has a working volume (e.g., of culture medium) of at least 500 L, at least 1000 L, at least 2000 L, at least 3000 L, at least 4000 L, at least 5000 L, at least 7500 L, at least 10000 L, at least 12500 L, at least 15000 L, at least 20000 L, at least 100000 L, or more. In some embodiments, the manufacturing-scale bioreactor culture has a working volume of 2000 L or 15000 L. In some embodiments, a manufacturing-scale bioreactor culture has a working volume in a range of 500 L to 1000 L, 500 L to 2500 L, 500 L to 5000 L, 500 L to 10000 L, 500 L to 15000 L, 500 L to 20000 L, 500 L to 100000 L, 2000 L to 5000 L, 2000 L to 10000 L, 2000 L to 15000 L, 2000 L to 20000 L, 2000 L to 100000 L, 15000 L to 20000 L, 15000 L to 100000 L, 20000 L to 50000 L, 20000 L to 100000 L, or 50000 L to 100000 L. In some embodiments, a manufacturing-scale bioreactor culture produces or is capable of producing at least 1 gram, at least 10 grams, at least 100 grams, 500 grams, 1000 grams, 2000 grams, 3000 grams, or more of a molecule. In some embodiments, a manufacturing-scale bioreactor culture produces or is capable of producing 1 gram to 10 grams, 1 gram to 100 grams, 1 gram to 500 grams, 10 gram to 1000 grams, 10 grams to 2000 grams, 100 grams to 1000 grams, 500 grams to 5000 grams, or more of a molecule. For example, a manufacturing-scale bioreactor may be a custom ABEC manufacturing-scale stainless steel bioreactor (e.g., in range of 2000 L to 15000 L).

The term "test bioreactor culture" refers to a bioreactor culture of a scale smaller than a manufacturing-scale bioreactor culture but sufficient for research and development purposes, e.g., to establish appropriate cell growth conditions, protein purification methods, etc. In some embodiments, a test-scale bioreactor culture produces less than 1 gram of a therapeutic molecule. In some embodiments, a test-scale bioreactor culture is a bench-scale bioreactor culture that has a working volume of 20 L or less, 10 L or less, 5 L or less, 4 L or less, 3 L or less, 2 L or less, 1 L or less, or 0.1 L or less. In some embodiments, the bench-scale bioreactor culture has a working volume of about 3 L. In some embodiments, a test-scale bioreactor culture is a bench-scale bioreactor culture that has a working volume of in a range of 100 mL to 500 mL, 100 mL to 1 L, 100 mL to 2 L, 100 mL to 5 L, 100 mL to 10 L, 100 mL to 20 L, 1 L to 3 L, 1 L to 5 L, 1 L to 10 L, or 1 L to 20 L. For example, the bench-scale bioreactor may be a 3 L or 5 L Applikon (Applikon Biotechnology, The Netherlands) bench-scale glass bioreactor. In some embodiments, a test-scale bioreactor culture is of a pilot-scale that has a working volume from 20 L to 1000 L or 50 L to 1000 L. In some embodiments, a test-scale bioreactor culture is a pilot-scale bioreactor culture that has a working volume in a range of 20 L to 100 L, 20 L to 250 L, 20 L to 500 L, 20 L to 1000 L, 100 L to 250 L, 100 L to 500 L, 100 L to 1000 L, 250 L to 500 L, 250 L to 1000 L or 500 L 1000 L. In some embodiments, the pilot-scale bioreactor culture has a working volume of 200 L. For example, the pilot-scale bioreactor may be a 200 L custom ABEC (ABEC Inc., Bethlehem, Pa.) pilot-scale stainless steel bioreactor.

It should be appreciated that the bioreactor scale may be defined by relative working volume capacity. In some embodiments, the test-scale bioreactor has is in a range of 0.0005% to 90%, 0.005% to 90%, 0.05% to 90%, 0.5% to 90%, 0.0005% to 50%, 0.005% to 50%, 0.05% to 50%, 0.5% to 50%, 0.0005% to 25%, 0.005% to 25%, 0.05% to 25%, or 0.5% to 25% of the working volume of the manufacturing-scale bioreactor. In some embodiments, the bench-scale bioreactor has between 0.0005% and 4% the working volume of the manufacturing-scale bioreactor. In some embodiments, the pilot-scale bioreactor has between 0.1% and 90% the working volume of the manufacturing-scale bioreactor. In some embodiments, the bench-scale bioreactor has about 0.15% the working volume of the manufacturing-scale bioreactor. In some embodiments the pilot-scale bioreactor has about 10% the working volume of the manufacturing-scale bioreactor.

Methods provided herein utilize models (e.g., statistical models) that relate Raman spectral data obtained from a bioreactor culture to a culture parameter. The term "culture parameter" refers to any physicochemical or cellular characteristic of the culture including, for example, the level of a constituents, the tonicity of a culture, the osmolality of a culture, the pH of a culture, the level of a cell (e.g., mammalian cell, insect cells, yeast cell, bacterial cells) in a culture, and other similar parameters.

It should be appreciated that a culture parameter may refer to any component of a culture, including but not limited to serum components, nutrient components, waste components, biological cells or biological products. In some embodiments, a culture parameter being assessed may be a molecular parameter, a cellular parameter, or a chemical parameter. In some embodiments a culture component is a nutrient, protein, peptide, carbohydrate, growth factor, cytokine or salt. For example, a culture component may be glucose glutamine, glutamate, lactose, ammonium or another component. In some embodiments, a culture component is a protein or other molecule, including a therapeutic or clinical molecule, expressed in or by a cell of a culture. In some embodiments, a protein or other molecule of interest is expressed in or by a recombinant cell. In some embodiments, a cell of a culture is a bacterial cell, a yeast cell, a plant cell, a mammalian cell, an insect cell, an algal cell or another cell type.

In some embodiments, a culture parameter may be a cellular parameter. It should be appreciated that a cellular parameter may pertain to any cell or collection of cells of the bioreactor culture. In some embodiments, a cell may be a bacterial cell, a yeast cell, a plant cell, a mammalian cell, an insect cell, an algal cell or another cell type. In some embodiments, a cellular parameter is viable cell density (VCD). In some embodiments, a cellular parameter is total cell density (TCD). In some embodiments, a bioreactor contains more than one cell type. In some embodiments, a cellular parameter is the VCD or TCD of one or more cell types when more than one cell types are present in the bioreactor culture.

In some embodiments, a culture parameter is a chemical parameter. It should be appreciated that a chemical parameter may pertain to any chemical species present in a bioreactor culture. In some embodiments, a chemical parameter is the level of a molecule. In some embodiments, a chemical parameter is a level of a dissolved gas. In some embodiments, a chemical parameter is pH. In some embodiments, a chemical parameter is a level of concentration of a salt or ion.

Multivariate Models

Aspects of the disclosure relate to methods of assessing a bioreactor culture using Raman spectroscopy. In some embodiments, a culture parameter of a bioreactor culture is modeled in a test-scale bioreactor using Raman spectroscopy, in which the model is used to predict a molecular parameter in a manufacturing-scale bioreactor culture based on a Raman spectra of the manufacturing-scale bioreactor culture. In some embodiments, the method of assessing a culture parameter of a manufacturing-scale bioreactor culture comprises obtaining a Raman spectrum of a manufacturing-scale bioreactor culture and determining a culture parameter of the manufacturing-scale bioreactor culture using a model that relates the Raman spectrum to the molecular parameter, in which the model is developed using at least one test-scale bioreactor culture.

Any appropriate statistical model may be used in methods disclosed herein. In some embodiments, the model is a regression model that relates predicted variables (e.g., culture parameters) and observable variables (e.g., Raman spectral data). In some embodiments, the regression model is a partial least squares model. In some embodiments, the model is a bilinear factor model that projects predicted variables (e.g., culture parameters) and observable variables (Raman spectral data) into a new space. In some embodiments, the model is a regression model that uses principal components analysis (PCA) for estimating unknown regression coefficients in the model. However, other multivariate analytical techniques may be used including, for example, support vector machines, multivariate linear regression, and others.

In some embodiments, Raman spectroscopy data is analyzed using multivariate partial least square (PLS) models. As disclosed herein, a set of single-scale and combination-scale models have been generated for various nutrient, metabolic waste and cell growth parameters of a cell culture process.

In some embodiments, methods provided herein involve multivariate models based on Raman spectral data obtained across multiple different scales of bioreactor cultures, including, for example, bench (e.g., up to 20 L) and/or pilot-scales (e.g., between 20 L and 1000 L), that are accurate at across a range of scales, including manufacturing-scales (e.g., 500 L or more). In some embodiments, by gathering data at bench, pilot and manufacturing-scales, models incorporate tremendous process variability, offering a great deal of robustness to the final model.

It should be appreciated that univariate-Y, multivariate-X predictive component models may be built from spectral data collected from bioreactors (e.g., during fed-batch cell culture processing). In some embodiments, no spectral data is collected off line or via reference solutions of chemically defined media or nutrient solutions. In one aspect, spectra are exported from an Raman instrument, e.g., a Raman probe configured for real-time measurements of Raman spectral data. In one embodiment, mathematical pre-processing methods are applied to all X-block cell culture spectra (e.g., including smoothing (e.g., 1st derivative Savitzky-Golay smoothing with 15 cm-1 point spacing and a quadratic polynomial) followed by Standard Normal Variate (SNV) and mean-centering). In one embodiment, Y-block reference component data is treated with unit-variance scaling (UV). In one embodiment, Y-block reference data outliers are identified and removed through analysis of scores plots, loading plots, residual plots, and Hotelling's $T^2$ plots or other appropriate techniques. The variable influence on projection (VIP) algorithm, which ranks the importance of the X-variables (spectral regions) taking into consideration the amount of explained variation in the Y-component variance (offline measurements), may be calculated and used to determine relative correlation of spectral regions throughout the full Raman shift range with offline data.

In some embodiments, because Raman spectroscopy is a form of vibrational spectroscopy, a user may have more confidence in identifying strong correlations within the Raman spectrum via modeling for chemically discrete components such as glucose, lactate, and others. Cellular density values are much less chemically discrete and may be based on imaging software techniques coupled with microscopes or visually with a hemocytometer. However, it has been found that robust Raman wavenumber regions and data preprocessing steps for generating strong correlations with VCD and TCD without experiencing the scale-dependent prediction quality may be used.

Many organic compounds naturally fluoresce and fluorescence interference background signal may change (e.g., increase) throughout a batch due to continuous accumulation of cells or cellular metabolism components within the system. Fluorescence interference may display a stronger signal than the inelastic Raman scattering which may lead to large backgrounds in Raman spectra as well as a degradation of the signal to noise ratio of the inelastic scattering data of interest. In this context, the use of longer wavelength excitation sources, such as 1064 nm, yield fluorescence responses in fewer materials. A five-fold improvement in glucose measurement capability, due to reduced fluorescence interference within a complex aqueous sample environment, was obtained when switching from 514.5 nm to 785 nm laser wavelength excitation.

Fluorescent background can also be managed by employing preprocessing and baseline normalization techniques to Raman spectral data, including first and second differentiation, Savitzky-Golay smoothing differentiation, SNV, multiplicative signal correction (MSC), extended multiplicative signal correction (EMSC) polynomial fitting, Fourier Transform, wavelet analysis, orthogonal signal correction (OSC) and extended inverted signal correction (EISC) among others. In some embodiments, the use of normalization techniques are not applicable to a long-duration fed-batch cell culture processes as the level of fluorescence interference is gradually scaled into the data over time meaning efficient normalization must be dynamic to a large group of spectra rather than static to a constant fluorescent background. In some embodiments, a consideration surrounding the choice of laser wavelength excitation involves the sample degradation potential of shorter wavelength, higher frequency lasers as photochemical degradation of biological samples may occur at 514.5 nm but not with 660 nm excitation wavelength.

In some embodiments, a universal cross-program models is provided that manages (e.g., through normalization) differences in peak cell growth and metabolic rates across different cell culture processes. In such embodiments, the Raman multivariate PLS models are built from one mammalian cell culture process and applied to another.

Further aspects of the disclosure relate to multivariate analyses using of Raman spectroscopy to monitor or assess bioreactor culture conditions in real-time. For example, multi-component, multi-scale Raman spectroscopy modeling may be used to monitor in real-time a bioreactor culture comprising cells engineered to produce a therapeutic protein (e.g., a monoclonal antibody). Culture conditions can be altered in response to the real-time information to maintain culture components within acceptable limits for production of the therapeutic protein.

In some embodiments, multivariate analysis techniques are disclosed herein that are advantageous because they do not involve overly-iterative processes. In particular, simplified protocols are provided for addressing relevant analytical steps including spectral preprocessing, spectral region selection, and outlier removal to create models exclusively from cell culture process data without the inclusion of spectral data from chemically defined nutrient solutions or targeted component spiking studies. Thus, an array of single-scale and combination-scale modeling iterations may be generated to evaluate technology capabilities and model scalability. Using such methods, analysis of prediction errors across models has shown that glucose, lactate, osmolality, glutamate and ammonia are well modeled, for example. Model strength may be assessed via predictive validation and by examining performance similarity across single-scale and combination-scale models. Accurate predictive models were generated for viable cell density (VCD) and total cell density (TCD), but demonstrated scale-dependencies in cross-scale predictions where only development data was used in calibration. Thus, for certain parameters, scale-dependencies may be considered when generating accurate predictive models. Glutamate and ammonia models also demonstrated accurate predictions within and across scales.

Aspects of the disclosure relate to the generation of biological sample growth and metabolite predictive models across development and manufacturing-scale bioreactors using in situ Raman spectroscopy. Raman spectroscopy provides a viable option for real-time bioreactor monitoring due to its ability to measure a myriad of chemical species with minimal interference from water, thus enabling in situ, real time process knowledge and quantification of a bioreactor environment. Research establishing chemical detection and measurement specificity within simple aqueous solutions is available as a reference for biochemically relevant components including glucose and other sugar carbohydrates, lactic acid and sodium lactate, glutamic acid and its derivatives, as well as non-aqueous solutions of liquid-phase ammonia. Progress has extended from the demonstration of neat component solution measurement specificity to complex aqueous solution applications related to the biomedical and biotechnology industries. Some examples of these areas include: a) clinically precise quantitative prediction of blood analytes for glucose, urea, albumin and hemoglobin in samples still containing red blood cells previously believed to distort and degrade the quality of optical data, establishing the limits of detection of glucose, lactate, glutamine and ammonia for different laser wavelengths in the spent media supernatant material of bioreactor samples, c) quality control motivated pre-screening of the chemically defined complex basal and feed media preparations used in mammalian cell culture with the aim of establishing a robust lot acceptance criteria and d) the pre-batch estimation of cell culture process yield via calibration of non-aqueous raw material spectroscopic data and batch output attributes.

Raman Spectroscopy

Raman spectroscopy relies on the inelastic scattering observed when a photon is impinged upon a chemical bond. The Raman equipment fires photons of a specific wavelength (energy level) at a target to be analyzed. When the photons enter the electron cloud of the chemical bond they are converted into energy and then back into photons and ejected from the bond. With inelastic scattering, the photon loses energy in the form of a wavelength shift. This wavelength shift is measured by the Raman system and the frequency of occurrence for all shifts is added to generate peaks (resulting in a Raman spectrum). These peaks, which represent a count of Raman shifts at a given energy, can be correlated to specific constituents in the system. In some embodiments, the intensities of one or more peaks can be used to determine the concentration of a component in a solution (e.g., by comparing to a standard curve of intensities generated using known concentrations).

In some embodiments, the Raman spectroscopy may be performed in the visible, near infrared, infrared, near ultraviolet, or ultraviolet (UV) range. In some embodiments, a signal enhancement technique known as Surface Enhanced Raman Spectroscopy (SERS), which relies on a phenomenon known as surface plasmonic resonance, may be used. In some embodiments, resonance Raman spectroscopy, tip-enhanced Raman spectroscopy, polarized Raman spectroscopy, stimulated Raman spectroscopy, transmission Raman spectroscopy, spatially offset Raman spectroscopy, difference Raman spectroscopy, Fourier Transform (FT) Raman, or hyper Raman spectroscopy may be used. In some embodiments, a Raman analyzer can be used that is configured with a laser or other suitable light source that operates at appropriate wavelengths (e.g., 325 nm, 514.5 nm, 532 nm, 632.8 nm, 647 nm, 752 nm, 785 nm, 830 nm, 1064 nm, etc.)

In some embodiments, data fusion may be used to augment the spectroscopic analysis. For example, a second spectroscopic analysis (e.g., Nuclear Magnetic Resonance (NMR), X-Ray Fluorescence (XRF), Small Angle X-Ray Scattering (SAXS), Powder Diffraction, Near Infrared Spectroscopy (NIR), or Fourier Transform Infrared Spectroscopy (FTIR)) may be performed to obtain a second spectrum of a lot sample, and data fusion analysis may be used to evaluate the lot sample.

In some embodiments, prediction models that are to be used herein for evaluating culture components are developed using a training data set based on one or more informative subsets or an entire Raman spectra, e.g., across 500 $cm^{-1}$ to 1700 $cm^{-1}$. For example, in some embodiments, a prediction model (e.g., a PLS model) will be established based on useful training information present within the entire spectra across 500 $cm^{-1}$-1700 $cm^{-1}$.

In one aspect, the disclosure provides methods of defining a Raman signature of a culture component and using the Raman signature to establish the level of the culture component within the bioreactor culture. In some embodiments, methods comprise obtaining a Raman spectrum of a culture component in a non-interfering or minimally-interfering solution, identifying peaks in the Raman spectrum that are associated with the culture component, obtaining a Raman spectrum of a culture medium comprising the culture component, and, removing peaks of the culture component in the Raman spectrum of the culture medium that are distorted compared to the peaks identified in the Raman spectrum of the culture component in a non-interfering or minimally-interfering solution. In some embodiments, the distorted peaks are laterally shifted peaks and inverted peaks. In some embodiments, the laterally shifted peak or inverted peak is removed if it is shifted by more than 5 cm$^{-1}$ in a concentration dependent fashion. In some embodiments of methods provided herein, the culture component is glucose. In some embodiments of methods provided herein, the culture component is lactate, glutamate, ammonia or osmolality. In some embodiments of methods provided herein, the culture component is VCD or TCD.

In one aspect of methods provided herein, a Raman spectrum of a component in a non-interfering or minimally-interfering solution is obtained. A non-interfering or minimally-interfering solution is a solution that allows for the generation of a Raman spectrum of a component with little to no interference of the component with other agents in the solution. In some embodiments, a non-interfering or minimally-interfering solution would be water, which may or may not have additional non-interfering or minimally-interfering components, such as buffers or salts. However, other non-interfering or minimally-interfering solutions may be used as aspects of the disclosure are not limited in this respect.

In some embodiments, a Raman spectra may be obtained of a component of interest (e.g., glucose) dissolved in a simple solvent such as water (e.g., by using an excitation laser) for purposes of determining the location of peaks or other components of a Raman spectrum that relate to the component. In some embodiments, Raman spectra may be obtained of multiple samples of a particular culture component at multiple concentrations. The samples used to build this spectral Raman library cover a range of concentrations that represents a reasonable approximation of the experimental range (e.g., the concentration range of the component in a culture medium). In some embodiments, a particular component is at a concentration in a range of 0.001 g/L to 0.05 g/L, 0.001 g/L to 0.1 g/L, 0.001 g/L to 0.5 g/L, 0.001 g/L to 1.0 g/L, 0.001 g/L to 10 g/L, 0.01 g/L to 0.05 g/L, 0.01 g/L to 0.1 g/L, 0.01 g/L to 0.5 g/L, 0.01 g/L to 1.0 g/L, 0.01 g/L to 10 g/L, 0.1 g/L to 0.5 g/L, 0.1 g/L to 1.0 g/L, 0.1 g/L to 10 g/L, 0.5 g/L to 1.0 g/L, or 0.5 g/L to 10 g/L. Thus, for instance, Raman spectra may be obtained from the same component at different concentration increments, such as increments of 0.001 g/L, 0.005 g/L, 0.01 g/L, 0.05 g/L, 0.1 g/L, 0.2 g/L, 0.3 g/L, 0.4 g/L, 0.5 g/L, 0.6 g/L, 0.7 g/L, 0.8 g/L, 0.9 g/L, 1.0 g/L, etc. The data obtained by using these Raman spectra are analyzed, including derivatizing and normalizing of the data if needed. Computer programs, including statistical software, may be used in this process. The data analysis results in peaks in the Raman spectrum that represent the basis peaks for the component of interest. The spectra are correlated with the known concentration of the component of interest (e.g., glucose).

In some embodiments, Raman spectra are also obtained of various concentrations of a component of interest (e.g., glucose) added to a culture medium of interest. It should be appreciated that the culture medium of interest may have a variety of make ups. However, the culture medium of interest ideally mimics closely the biological production culture medium and should include the major components present in cell culture media (polypeptide, sugars, salts, nucleic acids, cellular debris, and nutrients). The peaks identified in the Raman spectra of the component of interest (e.g., glucose) in the non-interfering or minimally-interfering solution are used to identify peaks in the Raman spectra of the component of interest (e.g., glucose) in the culture medium. The spectra of the component of interest (e.g., glucose) in the culture medium are trimmed to match the previously the peaks identified in the Raman spectra of the component of interest (e.g., glucose) in the non-interfering or minimally-interfering solution. In some embodiments, the spectra are trimmed by removing peaks that are distorted. In some embodiments, peaks that are distorted are peaks that are laterally shifted or inverted. However, it should be appreciated that distorted peaks may include any peak that fails to meet certain criteria (e.g., intensity, signal-to-noise (S/N) ratio, shape, closeness to other peaks). Distorted peaks can be identified by visual inspection or by using a computer program that identifies (and removes) peaks that do not meet certain criteria. For example, peaks may be excluded because they are laterally shifted or inverted by at least 5%, at least 10%, at least 20%, at least 30%, at least 40%, or at least 50% compared with a reference peak (e.g., a non-distorted peak). Similarly, peaks may be excluded because they have a S/N ratio that is at least 5%, at least 10%, at least 20%, at least 30%, at least 40%, or at least 50% less than the S/N of a reference peak (e.g., a non-distorted peak).

In some embodiments, only a portion of a Raman spectrum is evaluated. For example, data relating to only a portion of the Raman spectrum is evaluated and the remaining data is filtered or otherwise removed prior to analysis. In some embodiments, the distorted peaks that are removed are lateral peak shifts. In some embodiments, a lateral peak shift looks like a 2-dimensional peak that has been stretched out. This peak distortion is likely the result of a component in the culture medium that is interacting with one of the bonds on the molecule of interest, the presence of a bond with similar character, solvent distortion, or any combination of these phenomena. In some embodiments, the laterally shifted peak or inverted peak is shifted by more than 5 cm$^{-1}$ in a concentration dependent fashion. In some embodiments, the lateral peak is removed if it is shifted by more than 1 cm$^{-1}$, more than 2 cm$^{-1}$, more than 5 cm$^{-1}$, more than 10 cm$^{-1}$, or more than 20 cm$^{-1}$ or more. In some embodiments, the lateral peak is removed if it is shifted by more than 1 cm$^{-1}$, more than 2 cm$^{-1}$, more than 5 cm$^{-1}$, more than 10 cm$^{-1}$, or more than 20 cm$^{-1}$ or more, in a concentration dependent fashion.

In some embodiments, the distorted peaks that are removed are inversion peaks (also called "inverted peaks" herein). As provided for instance in the figures herein, an inversion peak is a peak where it appears that the lower concentration data is higher in magnitude than the high concentration data, when this relationship did not exist in the basis peaks. This type of distortion is usually due to a molecular species within the media that has similar vibrational properties and therefore similar peaks. In some embodiments, the inverted peak is removed if there is a lack of baseline.

In one aspect, the spectra from which the distorted peaks have been removed provide the Raman signature of the culture component. However it should be appreciated that the Raman signature may be further refined by using the trimmed spectra with the identified peaks through a larger cell culture dataset, e.g., by building a predictive PLS (partial least square) model. For instance, relevant cell culture spectra could be included along with the corresponding offline data for the constituent of interest into a multivariate software package such as SIMCA or the PLS Toolbox add-on for Matlab. In some embodiments, offline constituent data are collected through an appropriate analytical method and added to the model.

In some embodiments, the Raman signature comprises a selected number of peaks and associated peak ranges that allow for the evaluation (e.g., identification) of a culture component in a culture medium. In some embodiments, the Raman signature comprises a selected number of peaks and associated peak ranges that allow for the evaluation of the level of a culture component in a culture medium. In some embodiments, a Raman signature of a culture component comprises multiple combinations of identifying peaks. It should be appreciated that a minimal number of peaks may define a Raman signature. However, additional peaks may help refine the Raman signature. Thus, for instance, a Raman signature consisting of 4 peaks may provide a 95% certainty that a culture composition that shows those peaks contains the component associated with the Raman signature. However, a Raman signature consisting of 10 peaks may provide a 99% certainty that a culture composition that shows those peaks contains the component associated with the Raman signature. Similarly, a Raman signature consisting of 4 peaks may provide a 90% certainty that a culture composition that shows those peaks contains the component at the level of the component associated with the Raman signature. However, a Raman signature consisting of 10 peaks may provide a 98% certainty that a culture composition that shows those peaks contains the component at the level of the component associated with the Raman signature.

In one aspect, the disclosure provides Raman signatures of culture components. In some embodiments, the culture component is glucose. In some embodiments, the disclosure provides Raman signatures of glucose that allow for evaluating the presence of glucose in a sample. In some embodiments, the disclosure provides Raman signatures of glucose that allow for evaluating the level of glucose in a sample. In some embodiments, the disclosure provides Raman signatures of glucose that allow for evaluating the presence of glucose in a culture medium. In some embodiments, the disclosure provides Raman signatures of glucose that allow for evaluating the level of glucose in a culture medium.

In one aspect, the Raman signature of glucose comprises peaks in the 200 $cm^{-1}$ to 3400 $cm^{-1}$ wavenumber range. As used herein, wavenumber refers to the spatial frequency of a wave, which may be in cycles per unit distance or radians per unit distance. In some embodiments, the Raman signature of glucose comprises at least 4 peaks in the 200 $cm^{-1}$ to 3400 $cm^{-1}$ wavenumber range. In some embodiments, the Raman signature of glucose comprises at least 6 peaks in the 200 $cm^{-1}$ to 3400 $cm^{-1}$ wavenumber range. In some embodiments, the Raman signature of glucose comprises at least 10 peaks in the 200 $cm^{-1}$ to 3400 $cm^{-1}$ wavenumber range. In some embodiments, the Raman signature of glucose comprises at least 20 peaks in the 200 $cm^{-1}$ to 3400 $cm^{-1}$ wavenumber range. In some embodiments, the Raman signature of glucose comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, or at least 30 peaks in the 200 $cm^{-1}$ to 3400 $cm^{-1}$ wavenumber range.

In some embodiments, the Raman signature of glucose comprises at least 4 peaks in the 200 $cm^{-1}$ to 3400 $cm^{-1}$ wavenumber range. In some embodiments, the 4 peaks are selected from the following 6 peaks:
peak 1, range: 364-440, peak 402 (all in $cm^{-1}$),
peak 2, range: 511-543, peak 527 (all in $cm^{-1}$),
peak 3, range: 577-600, peak 589 (all in $cm^{-1}$),
peak 4, range: 880-940, peak 911 (all in $cm^{-1}$),
peak 5, range: 1130-1180, peak 1155 (all in $cm^{-1}$), and
peak 6, range: 1262-1290, peak 1276 (all in $cm^{-1}$).

In some embodiments, the set of 4 selected peaks is: {peak 1, peak 2, peak 3, peak 4}, {peak 1, peak 2, peak 3, peak 5}, {peak 1, peak 2, peak 3, peak 6}, {peak 1, peak 2, peak 4, peak 5}, {peak 1, peak 2, peak 4, peak 6}, {peak 1, peak 2, peak 5, peak 6}, {peak 1, peak 3, peak 4, peak 5}, {peak 1, peak 3, peak 4, peak 6}, {peak 1, peak 3, peak 5, peak 6}, {peak 1, peak 4, peak 5, peak 6}, {peak 2, peak 3, peak 4, peak 5}, {peak 2, peak 3, peak 4, peak 6}, {peak 2, peak 3, peak 5, peak 6}, {peak 2, peak 4, peak 5, peak 6}, or {peak 3, peak 4, peak 5, peak 6}.

In some embodiments, the Raman signature of glucose comprises at least 6 peaks in the 200 $cm^{-1}$ to 3400 $cm^{-1}$ wavenumber range. In some embodiments, the 6 peaks are:
peak 1, range: 364-440, peak 402 (all in $cm^{-1}$),
peak 2, range: 511-543, peak 527 (all in $cm^{-1}$),
peak 3, range: 577-600, peak 589 (all in $cm^{-1}$),
peak 4, range: 880-940, peak 911 (all in $cm^{-1}$),
peak 5, range: 1130-1180, peak 1155 (all in $cm^{-1}$), and
peak 6, range: 1262-1290, peak 1276 (all in $cm^{-1}$).

In some embodiments, the Raman signature of glucose comprises at least 10 peaks in the 200 $cm^{-1}$ to 3400 $cm^{-1}$ wavenumber range. In some embodiments, the 10 peaks are:
peak 1, range: 364-440, peak 402 (all in $cm^{-1}$),
peak 2, range: 511-543, peak 527 (all in $cm^{-1}$),
peak 3, range: 577-600, peak 589 (all in $cm^{-1}$),
peak 4, range: 749-569, peak 759 (all in $cm^{-1}$),
peak 5, range: 880-940, peak 911 (all in $cm^{-1}$),
peak 6, range: 1050-1070, peak 1060 (all in $cm^{-1}$),
peak 7, range: 1110-1140, peak 1125 (all in $cm^{-1}$),
peak 8, range: 1130-1180, peak 1155 (all in $cm^{-1}$),
peak 9, range: 1262-1290, peak 1276 (all in $cm^{-1}$), and
peak 10, range: 1520-1578, peak 1549 (all in $cm^{-1}$).

In some embodiments, the Raman signature of glucose comprises at least 20 peaks in the 200 $cm^{-1}$ to 3400 $cm^{-1}$ wavenumber range. In some embodiments, the 20 peaks are:
peak 1, range: 364-440, peak 402 (all in $cm^{-1}$),
peak 2, range: 511-543, peak 527 (all in $cm^{-1}$),
peak 3, range: 577-600, peak 589 (all in $cm^{-1}$),
peak 4, range: 720-740, peak 732 (all in $cm^{-1}$),
peak 5, range: 769-799, peak 789 (all in $cm^{-1}$),
peak 6, range: 835-875, peak 855 (all in $cm^{-1}$),
peak 7, range: 880-940, peak 911 (all in $cm^{-1}$),
peak 8, range: 950-1015, peak 968 (all in $cm^{-1}$),
peak 9, range: 1050-1070, peak 1060 (all in $cm^{-1}$),
peak 10, range: 1063-1080, peak 1073 (all in $cm^{-1}$),
peak 11, range: 1110-1140, peak 1125 (all in $cm^{-1}$),
peak 12, range: 1130-1180, peak 1155 (all in $cm^{-1}$),
peak 13, range: 1190-1240, peak 1210 (all in $cm^{-1}$),
peak 14, range: 1262-1290, peak 1276 (all in $cm^{-1}$),
peak 15, range: 1330-1342, peak 1336 (all in $cm^{-1}$),
peak 16, range: 1350-1380, peak 1371 (all in $cm^{-1}$),
peak 17, range: 1390-1410, peak 1401 (all in $cm^{-1}$),
peak 18, range: 1425-1475, peak 1450 (all in $cm^{-1}$),
peak 19, range: 1465-1480, peak 1473 (all in $cm^{-1}$), and
peak 20, range: 1520-1578, peak 1549 (all in $cm^{-1}$).

In some embodiments, a culture component is lactate. In some embodiments, the disclosure provides Raman signatures of lactate that allow for evaluating the presence of lactate in a sample. In some embodiments, the disclosure provides Raman signatures of lactate that allow for evaluating the level of lactate in a sample. In some embodiments, the disclosure provides Raman signatures of lactate that allow for evaluating the presence of lactate in a culture medium. In some embodiments, the disclosure provides Raman signatures of lactate that allow for evaluating the level of lactate in a culture medium.

In one aspect, the Raman signature of lactate comprises peaks in the 200 cm-1 to 3400 cm-1 wavenumber range (FIGS. 6A-D). In some embodiments, the Raman signature of lactate comprises at least 2 peaks in the 200 cm-1 to 3400 cm-1 wavenumber range. In some embodiments, the Raman signature of lactate comprises at least 4 peaks in the 200 cm-1 to 3400 cm-1 wavenumber range. In some embodiments, the Raman signature of lactate comprises at least 6 peaks in the 200 cm-1 to 3400 cm-1 wavenumber range. In some embodiments, the Raman signature of lactate comprises at least 7 peaks in the 200 cm-1 to 3400 cm-1 wavenumber range. In some embodiments, the Raman signature of lactate comprises at least 1, at least 2, at least 3, at least 4, at least 5, at least 6 or at least 7 peaks in the 200 cm-1 to 3400 cm-1 wavenumber range.

In some embodiments, the Raman signature of lactate comprises at least 2 peaks in the 200 cm-1 to 3400 cm-1 wavenumber range. In some embodiments, the 2 peaks are selected from the following 7 peak ranges:
 peak 1, range: 500-575, (all in cm-1),
 peak 2, range: 820-880, (all in cm-1),
 peak 3, range: 900-950, (all in cm-1),
 peak 4, range: 1010-1110, (all in cm-1),
 peak 5, range: 1290-1340, (all in cm-1),
 peak 6, range: 1360-1510, (all in cm-1), and
 peak 7, range: 2840-3020, (all in cm-1).
In some embodiments, the set of 2 selected peaks is: {peak 1, peak 2}, {peak 1, peak 3}, {peak 1, peak 4}, {peak 1, peak 5}, {peak 1, peak 6}, {peak 1, peak 7}, {peak 2, peak 3}, {peak 2, peak 4}, {peak 2, peak 5}, {peak 2, peak 6}, {peak 2, peak 7}, {peak 3, peak 4}, {peak 3, peak 5}, {peak 3, peak 6}, {peak 3, peak 7}, {peak 4, peak 5}, {peak 4, peak 6}, {peak 4, peak 7}, {peak 5, peak 6}, {peak 5, peak 7}, or {peak 6, peak 7}.

In some embodiments, the Raman signature of lactate comprises at least 4 peaks in the 200 cm-1 to 3400 cm-1 wavenumber range. In some embodiments, the 4 peaks are selected from the following 7 peak ranges:
 peak 1, range: 500-575, (all in cm-1),
 peak 2, range: 820-880, (all in cm-1),
 peak 3, range: 900-950, (all in cm-1),
 peak 4, range: 1010-1110, (all in cm-1),
 peak 5, range: 1290-1340, (all in cm-1),
 peak 6, range: 1360-1510, (all in cm-1), and
 peak 7, range: 2840-3020, (all in cm-1).
In some embodiments, the Raman signature of lactate comprises at least 6 peaks in the 200 cm-1 to 3400 cm-1 wavenumber range. In some embodiments, the 6 peaks are selected from the following 7 peak ranges:
 peak 1, range: 500-575, (all in cm-1),
 peak 2, range: 820-880, (all in cm-1),
 peak 3, range: 900-950, (all in cm-1),
 peak 4, range: 1010-1110, (all in cm-1),
 peak 5, range: 1290-1340, (all in cm-1),
 peak 6, range: 1360-1510, (all in cm-1), and
 peak 7, range: 2840-3020, (all in cm-1).
In some embodiments, the Raman signature of lactate comprises at least 7 peaks in the 200 cm-1 to 3400 cm-1 wavenumber range. In some embodiments, the 7 peaks are:
 peak 1, range: 500-575, (all in cm-1),
 peak 2, range: 820-880, (all in cm-1),
 peak 3, range: 900-950, (all in cm-1),
 peak 4, range: 1010-1110, (all in cm-1),
 peak 5, range: 1290-1340, (all in cm-1),
 peak 6, range: 1360-1510, (all in cm-1), and
 peak 7, range: 2840-3020, (all in cm-1).

It should be appreciated that, as for glucose and lactate, the parameters including but not limited to glutamate, ammonium, osmolality, VCD and TCD may be similarly evaluated.

Monitoring and Control of Culture Parameters

In one aspect, the disclosure provides methods for evaluating the level of a component in of a bioreactor culture. As used herein, the term "level" refers to an amount or concentration of a molecule entity, chemical species, component, or object. In one aspect, the disclosure provides methods for adjusting a level of a component in of a bioreactor culture. In some embodiments, the culture component is glucose.

The production of biological products, such as therapeutic proteins, by biological processes has been used for many years. However, controlling the composition of the culture medium remains challenging especially for large scale and continuous production methods. A problem of sub-optimal titer has been described by the Crabtree effect and higher level analogs, e.g., a situation in which cell culture cells are exposed to high levels of glucose and oxidative phosphorylation is inhibited and cellular processes become stunted due to the stressful nature of the environment (Thomson J M, Gaucher E A, Burgan M F, De Kee D W, Li T, Aris J P, Benner S A. (2005). "Resurrecting ancestral alcohol dehydrogenases from yeast." Nat Genet. 37 (6): 630-635). The Crabtree effect (as well as mammalian analogs) is seen as an acceptable tradeoff for the nutrient-deficiency safety buffer offered by high levels of glucose in a bolus feed strategy. A second issue is one of highly variable nutrient levels leading to erratic protein glycosylation, sialylation as well as other key product quality attributes. The effects of inconsistent cell culture environments on product quality attributes have been described previously (Castilho, Leda dos Reis. Animal cell technology: from biopharmaceuticals to gene therapy. 2008. Taylor and Francis Group. P138; Peifeng Chen, Sarah W. Harcum, Effects of elevated ammonium on glycosylation gene expression in CHO cells, Metabolic Engineering, Volume 8, Issue 2, March 2006, Pages 123-132).

A feed strategy of daily bolus feeds (fed-batch) provides a conservative but sub-optimal approach to cellular productivity and product quality. The drawback to this conservative approach is two-fold. First, to ensure that the culture is not depleted of nutrients in between data points, certain nutrients are kept at safe, high levels. These variable levels, of glucose for example, may limit the batch productivity and consistency. By controlling these nutrient levels at a consistent concentration throughout the run, the individual cell ultimately receives a stable level of feed/nutrients. The second drawback is that a single daily feed is designed to have all of the nutrients that the culture needs to sustain it until the next feed. Because this is fed into the system over a relatively short period of time (less than 1 hour) it causes substantial swings in the nutrient levels that the cells are exposed to. This leads to inconsistencies in the product quality output of the cells. Another challenge of current methods is the sampling requirement to determine the levels of components (e.g., nutrients, metabolites). Sampling is a main source for labor and contamination.

In one aspect, the disclosure provides methods for evaluating and adjusting a culture component level in a culture medium that addresses challenges associated with current methods of biological production.

In one aspect, the disclosure provides methods of evaluating a culture component level in a culture medium. In some embodiments, methods provided herein comprise obtaining a Raman spectrum of a culture medium, parsing the Raman spectrum with a Raman signature of the culture component to identify peaks corresponding the culture component, and measuring the intensity of the identified peaks to evaluate the culture component level in the medium. In some embodiments, methods provided herein further comprises adjusting the culture component level if the level is outside a predetermined range. In some embodiments, the culture component is glucose.

An element of methods provided herein is obtaining a Raman spectrum of the culture medium and parsing the Raman spectrum with the Raman signature of a culture component of interest (e.g., glucose). In some embodiments, a wide range Raman spectrum is obtained from the culture medium (e.g., including all or many of the wavelengths that are associated with Raman spectroscopy of components of culture mediums). However, in some embodiments, only narrow regions of the Raman spectrum that correspond to the Raman signature of the component of interest are obtained and/or interrogated. In some embodiments, multiple Raman spectra are obtained from different locations within a culture medium. The data from such multiple spectra may be averaged if appropriate.

In addition, in some embodiments, the intensity of a Raman spectra will be evaluated to determine the level of the culture component in a sample. In some embodiments, the intensity of a Raman spectra is evaluated only within one or more peaks of the spectra that correspond to a Raman signature to determine the level of the culture component in a sample. Thus, in some embodiments, only signature peaks need to be evaluated, and the intensity of an entire Raman spectra does not need to be evaluated Alternatively, or in addition, the Raman spectra may be parsed with Raman signatures associated with a specific level of the culture component of interest in culture medium. In some embodiments, the culture component is glucose and the Raman spectrum of the culture medium is parsed with the Raman signature of glucose in culture medium. In some embodiments, the intensity of the Raman spectra will be evaluated to determine the level of glucose in the sample. Alternatively, or in addition, the Raman spectra may be parsed with Raman signatures associated with a specific level of glucose in culture medium. In some embodiments, the Raman spectrum is parsed with one or more of the following Raman signatures:

1) a Raman signature of glucose comprising at least 4 peaks in the 200 $cm^{-1}$ to 3400 $cm^{-1}$ wavenumber range. In some embodiments, the 4 peaks are selected from the following 6 peaks:
peak 1, range: 364-440, peak 402 (all in $cm^{-1}$),
peak 2, range: 511-543, peak 527 (all in $cm^{-1}$),
peak 3, range: 577-600, peak 589 (all in $cm^{-1}$),
peak 4, range: 880-940, peak 911 (all in $cm^{-1}$),
peak 5, range: 1130-1180, peak 1155 (all in $cm^{-1}$), and
peak 6, range: 1262-1290, peak 1276 (all in $cm^{-1}$).

2) a Raman signature of glucose comprising at least 6 peaks in the 200 $cm^{-1}$ to 3400 $cm^{-1}$ wavenumber range. In some embodiments, the 6 peaks are:
peak 1, range: 364-440, peak 402 (all in $cm^{-1}$),
peak 2, range: 511-543, peak 527 (all in $cm^{-1}$),
peak 3, range: 577-600, peak 589 (all in $cm^{-1}$),
peak 4, range: 880-940, peak 911 (all in $cm^{-1}$),
peak 5, range: 1130-1180, peak 1155 (all in $cm^{-1}$), and
peak 6, range: 1262-1290, peak 1276 (all in $cm^{-1}$).

3) a Raman signature of glucose comprising at least 10 peaks in the 200 $cm^{-1}$ to 3400 $cm^{-1}$ wavenumber range. In some embodiments, the 10 peaks are:
peak 1, range: 364-440, peak 402 (all in $cm^{-1}$),
peak 2, range: 511-543, peak 527 (all in $cm^{-1}$),
peak 3, range: 577-600, peak 589 (all in $cm^{-1}$),
peak 4, range: 749-569, peak 759 (all in $cm^{-1}$),
peak 5, range: 880-940, peak 911 (all in cm-1),
peak 6, range: 1050-1070, peak 1060 (all in $cm^{-1}$),
peak 7, range: 1110-1140, peak 1125 (all in $cm^{-1}$),
peak 8, range: 1130-1180, peak 1155 (all in $cm^{-1}$),
peak 9, range: 1262-1290, peak 1276 (all in $cm^{-1}$), and
peak 10, range: 1520-1578, peak 1549 (all in $cm^{-1}$).

4) a Raman signature of glucose comprising at least 20 peaks in the 200 $cm^{-1}$ to 3400 $cm^{-1}$ wavenumber range. In some embodiments, the 20 peaks are:
peak 1, range: 364-440, peak 402 (all in $cm^{-1}$),
peak 2, range: 511-543, peak 527 (all in $cm^{-1}$),
peak 3, range: 577-600, peak 589 (all in $cm^{-1}$),
peak 4, range: 720-740, peak 732 (all in $cm^{-1}$),
peak 5, range: 769-799, peak 789 (all in $cm^{-1}$),
peak 6, range: 835-875, peak 855 (all in $cm^{-1}$),
peak 7, range: 880-940, peak 911 (all in $cm^{-1}$),
peak 8, range: 950-1015, peak 968 (all in $cm^{-1}$),
peak 9, range: 1050-1070, peak 1060 (all in $cm^{-1}$),
peak 10, range: 1063-1080, peak 1073 (all in $cm^{-1}$),
peak 11, range: 1110-1140, peak 1125 (all in $cm^{-1}$),
peak 12, range: 1130-1180, peak 1155 (all in $cm^{-1}$),
peak 13, range: 1190-1240, peak 1210 (all in $cm^{-1}$),
peak 14, range: 1262-1290, peak 1276 (all in $cm^{-1}$),
peak 15, range: 1330-1342, peak 1336 (all in $cm^{-1}$),
peak 16, range: 1350-1380, peak 1371 (all in $cm^{-1}$),
peak 17, range: 1390-1410, peak 1401 (all in $cm^{-1}$),
peak 18, range: 1425-1475, peak 1450 (all in $cm^{-1}$),
peak 19, range: 1465-1480, peak 1473 (all in $cm^{-1}$), and
peak 20, range: 1520-1578, peak 1549 (all in $cm^{-1}$).

In one aspect, methods of evaluating a culture component level in a culture medium comprise adjusting the glucose level if the level is outside a predetermined range. In some embodiments, methods further comprise adjusting the glucose level if the level is outside a range of 0.5-12 g/L, 1-3 g/L, 1-5 g/L, or 1-10 g/L. In some embodiments, the glucose level may be increased if the level is below a reference or threshold level, such as below 0.01 g/L, 0.1 g/L, 0.5 g/L, 1 g/L, 2.5 g/L, or 5 g/L. In some embodiments, the glucose level may be decreased if the level is above a reference or threshold level, such as above 3 g/L, 5 g/L, 10 g/L or 12 g/L. It should be appreciated that the optimal glucose level will depend on the nature of the production method, the type of cells, the duration of the production, the size of the production vessel, etc. However, a person of ordinary skill in the art can determine an optimal or desired range of glucose for a particular configuration. Determining that a level of glucose is outside this range (e.g., if glucose levels are too low) can be used as a trigger to adjust the glucose concentration. In some embodiments, methods further comprise adjusting the glucose level if the level is outside a range of 0.1-100 g/L, 0.2-50 g/L, 0.5-10 g/L, 1-5 g/L, or 1-3 g/L. In some embodiments, methods further comprise adjusting the glucose level if the level of glucose falls below 1 g/L. In some embodiments, methods further comprise adjusting the glucose level if the level of glucose falls below 3 g/L, 2 g/L, 1 g/L, 0.5 g/L, or lower. It should be appreciated that peak signatures and intensities that are used as references can be established for different concentrations of a compound of interest (e.g., glucose) and then used to determine the concentration of the compound of interest.

In one aspect, methods of evaluating a culture component level in a culture medium further comprise evaluating an additional culture parameter. In some embodiments, an additional culture parameter is one or more of the following culture parameters: viable cell density, level of lactate, level of glutamine, level of glutamate, level of ammonium, osmolality, or pH. It should be appreciated that the additional parameters may be determined by any method, for instance, pH may be determined by a pH meter or a coloring agent, while viable cell density may be determined by non-Raman spectroscopic methods. In some embodiments, the one or more culture parameters are determined by Raman spectroscopy. In some embodiments, evaluating the level of glucose and the one or more culture parameters is done simultaneously.

In one aspect, methods of evaluating a culture component level in a culture medium are provided that comprise adjusting the glucose level if the level is outside a predetermined combination of ranges of glucose level and the one or more culture parameters. In some embodiments, the glucose level is adjusted if the level is outside a range of 1-3 g/L. In some embodiments, methods of evaluating a culture component level in a culture medium comprise adjusting the one or more culture parameters if the one or more culture parameters are outside a predetermined combination of ranges of glucose level and the one or more culture parameters. It should be appreciated that methods provided herein allow for evaluation of and, the subsequent adjustment of, the level of glucose and additional parameters if such levels fall outside a predetermined range. The ranges of glucose and the one or more additional parameters can be set independently, or in combination. For instance, a level of glucose of 1-2 g/L may be desired if the viable cell density is at or below a reference level. However, a level of glucose of 2-3 g/L may be desired if the viable cell density is above a reference level. For example, a reference density may be $1\times10^4$ cells/mL, $5\times10^4$ cells/mL, $1\times10^5$ cells/mL, $5\times10^5$ cells/mL, $1\times10^6$ cells/mL, $5\times10^6$ cells/mL, $1\times10^6$ cells/mL, $5\times10^6$ cells/mL, In this example, the desired level of glucose depends on additional cell culture parameters, and both the level of glucose and the level of the additional parameter (e.g., viable cell density) are evaluated prior to making a decision on the adjustment of the level of glucose (or an additional parameter, such as the level of ammonium). It should further be appreciated that algorithms may be used that can aid in determining, or determine, if a level needs to be adjusted. For instance, Partial Least Squares (PLS) statistical methods can be used to build the correlations into predictive models. In some embodiments, the predictive models take into account the levels of glucose and viable cell density predictions and can be used to calculate the GUR (glucose uptake rate) of the system. The GUR is used to predict glucose consumption and therefore determine how much nutrient feed is required to maintain the system around a given set point.

In some embodiments of methods provided herein, the level of glucose and the one or more culture parameters are evaluated on an continuing basis, and the level of glucose and/or the one or more culture parameters are adjusted if the level of glucose and/or the one or more culture parameters are outside a predetermined combination of ranges of glucose level and the one or more culture parameters. In some embodiments, the level of glucose and the additional parameters are evaluated every hour. Monitoring on a continuing basis includes continuous monitoring and/or monitoring at regular intervals (e.g., once per minute, once per hour, twice per hour, daily, weekly, monthly, etc.)

It should be appreciated that methods provided herein allow for a feedback loop. In some embodiments, the level of glucose and, optionally, one or more additional parameters is determined and if the level of glucose and, optionally, one or more additional parameters is found to be unsatisfactory, the level of glucose and, optionally, one or more additional parameters is adjusted. In some embodiments, the adjustment is done automatically. For instance, if the level of glucose is evaluated and found to be too low, a pump may be activated that adds additional glucose to the culture medium. The monitoring of the levels of glucose and, optionally, one or more additional parameters may be done continuously. In some embodiments, the level of glucose and the additional parameters are evaluated continuously (multiple time within one minute), every minute, every 2 minutes, every 3 minutes, every 5 minutes, every 10 minutes, every 20 minutes, every 30 minutes, every hour, every 2 hours, or less frequently.

In one aspect, the disclosure provides an automated feedback system with one or more of the following elements: A data management system that uses the following information flow to drive automation:

Constituent concentration>>Laser wavenumber shift>>Raman collection system>>Raw Raman spectra>>Model application system>>Predicted Raman value>>Consumption calculation (within bioreactor interface)>>Feed required for maintenance>>Change in feed (via pump speed, weight change, etc.)>>Change in constituent concentration For instance, a culture component (e.g., glucose) is measured using Raman, the raw data is collected by the Raman system and transmitted to a model application system. Within the model application system the data treatments of the predictive PLS model are applied to raw spectra and the peaks are analyzed giving a predicted culture component value. The prediction is sent to the bioreactor interface which uses it to as an input for an algorithm which determines the consumption rate of the constituent and calculates the rate at which a feed must be added in order to maintain a specific concentration. The calculated pump speed will change the addition rate which will increase or decrease the concentration of the culture component as needed.

In some embodiments, multiple production reactors execute dozens of batches per year in an optimized run rate and high-throughput scale. Infrastructure and procedures are provided that support the volume of data, consistent addition of new data, and rolling manipulation from model to model and analyst to analyst. In some embodiments, Raman spectra-based data load from a single batch comprises about three thousand Raman shift data points per spectra or more, multiplied by roughly one thousand time course spectra collected each run, totaling an estimated three million data values per batch.

In some embodiments, Raman measurements may be performed to evaluate the level of constituents in cultures or product yield from cell cultures (e.g., mammalian cell cultures). In some embodiments, Raman spectroscopy may be used for microbial fermentation applications for determining in situ process titer, glucose and ethanol (for example), as well as simultaneous multi-component prediction and monitoring. In some embodiments, Raman measurements may be performed ex situ on supernatant samples (e.g., to evaluate product yield). In some embodiments, cell culture bioreactor monitoring may be used to evaluate in situ glucose, lactate, glutamine, glutamate, ammonium, VCD and TCD levels, among others. In some embodiments, set-point based control of glucose or other culture components may be accomplished via application of a Raman spectroscopy, e.g., using a derived PLS model.

In some embodiment, methods provided herein provide are useful for on-line monitoring and control of culture components (e.g., multiple components in parallel). In some embodiments, monitoring and control methods disclosed herein permit control set-points to be established on nutrient and/or waste concentrations, for example. In some embodiments, monitoring and control methods disclosed herein provided herein eliminate the need for bolus-feed additions which can drastically swing chemical compositions. In some embodiments, monitoring and control methods disclosed herein may be used to manipulate cumulative cellular metabolism by leveraging control set-point capability of nutrient components to dampen metabolic waste product accumulations, establishing robust continuous feed per cell implementations. In some embodiments, on-line monitoring provides information useful for batch level process trending and modeling applications, such as, for example, SIMCA Batch On-Line (SBOL) (Umetrics Inc., San Jose, Calif.), which permits rapid identification of batch-to-batch deviations to help improve process consistency.

In one aspect, the disclosure provides methods for the analysis of biological samples. In some embodiments, the disclosure provides methods for evaluating a biological production process. In some embodiments, the disclosure provides methods for evaluating a culture medium. In some embodiments, the disclosure provides methods for evaluating a culture component level in a culture medium.

In some embodiments, analysis of a culture medium comprises determining the presence of one or more culture components in a biological sample. In some embodiments, analysis of a biological sample comprises evaluating the level of a culture component. It should be appreciated that methods provided herein allow for the analysis of a wide variety of culture media and biological samples. Culture media and biological samples, as used herein, refer to media and samples that include one or more components (e.g., glucose) of a biological production process. For example, a biological process may be the production of one or more biological molecules in a cell production system. Biological molecules may be antibodies or other molecules (e.g., recombinant polypeptides). Components of a biological production process include sugars, amino acids, peptides, proteins, nucleic acids, etc.

In some embodiments, evaluating a culture medium includes evaluating the presence of one or more components (culture components) in a biological sample or culture medium. In some embodiments, evaluating a culture medium includes evaluating the level of one or more components in a biological sample. In some embodiments, the presence or level of one or more culture components can be correlated to the quality of the sample and/or the progress of a particular biological manufacturing process. Culture components that can be analyzed according to methods provided herein include sugars (e.g., glucose), amino acids, nucleic acid, etc. For instance, for an optimal biological production process it may be desired to have a specific level (e.g., concentration) of glucose to be present at the beginning of the biological production process. Determining the presence and/or the level of glucose than allows for evaluating a biological sample. Furthermore, as provided herein, if less than the desired level of glucose is present the level of glucose may be increased by the addition of glucose solution.

In some embodiments, a Raman spectroscope is configured inline with a bioreactor, vessel or fluid conduit of either one in order to non-invasively (e.g., in a sterile fashion) monitor and/or determine levels of culture components in the bioreactor or other vessel.

In some embodiments, the level of a component during the biological production process can be used to monitor the progress of the biological production process. Thus, for instance, if glucose is consumed during a biological production process, the presence of the same level of glucose during the progression of the biological production process as at the beginning of the biological production process is a sign that the bioprocess is not proceeding as desired. In addition, the presence of a new component can be a sign that the biological production process is proceeding in some embodiments, or not proceeding in other embodiments, as planned. Thus, a biological production process may be monitored for the occurrence of desired product or indicator that biological production process is progressing as desired. On the other hand, the presence of a particular metabolite may be a sign that cells in the biological production process are not generating the desired product but, for instance, are merely proliferating. Thus, determining the presence of one or more components in a biological sample is a way of evaluating the sample and predicting the successfulness (e.g., yield) of a biological production process.

It should be appreciated that the component analysis can also be expanded to multiple components. Thus, for instance, a biological production process may require a particular ratio of glucose to glutamate to proceed optimally. A sample may be monitored prior to or throughout the reaction for this relationship and the conditions may be adjusted if the observed ratio deviates from the desired ratio.

In one aspect, the disclosure provides methods for evaluating a biological sample by generating a reference library of Raman signatures of culture components that are associated with a sample with a particular outcome (e.g., if a particular component is not aggregated or oxidized). For instance, Raman signatures can be generated from components in samples that are known to result in a biological production process with a good yield and Raman signatures can be generated from samples that are associated with a low yield (e.g., where the Raman spectrum would show undesired degradation of a particular component). A Raman spectrum can subsequently be taken from an unknown sample and be parsed with the library of Raman signatures In some embodiments, the herein-described models and Raman spectra collected from culture medium may be used to optimize the culture medium for biological production. The cell growth may be, for example, for protein production (e.g., for antibody production, for example for humanized antibody production). In some embodiments, cell growth may be that of a recombinant cell (e.g., bacterial, yeast, mammalian or other cell type) that expresses a protein of interest. In some embodiments, a protein of interest may be, but is not limited to, anti-LINGO, anti-LINGO-1, interferon (e.g., interferon beta 1a—AVONEX), Abciximab (REOPRO®), Adalimumab (HUMIRA®), Alemtuzumab (CAMPATH®), Basiliximab (SIMULECT®), Bevacizumab (AVASTIN®), Cetuximab (ERBITUX®), Certolizumab pegol (CIMZIA®), Daclizumab (ZENAPAX®), Eculizumab (SOLIRIS®), Efalizumab (RAPTIVA®), Gemtuzumab (MYLOTARG®), Ibritumomab tiuxetan (ZEVALIN®), Infliximab (REMICADE®), Muromonab-CD3

(ORTHOCLONE OKT3®), Natalizumab (TYSABRI®), Omalizumab (XOLAIR®), Palivizumab (SYNAGIS®), Panitumumab (VECTIBIX®), Ranibizumab (LUCENTIS®), Rituximab (RITUXAN®), Tositumomab (BEXXAR®), and/or Trastuzumab (HERCEPTIN®). In some embodiments, the protein of interest is Natalizumab (TYSABRI®). In some embodiments, the protein of interest is a blood cascade protein. Blood cascade proteins are known in the art and include, but are not limited to, Factor VII, tissue factor, Factor IX, Factor X, Factor XI, Factor XII, Tissue factor pathway inhibitor, Factor V, prothrombin, thrombin, vonWillebrandFactor, kininigen, prekallikrien, kallikrein, fribronogen, fibrin, protein C, thrombomodulin, and antithrombin. In some embodiments, the blood cascade protein is Factor IX or Factor VIII. It should be appreciated that methods provided herein are also applicable for uses involving the production of versions of blood cascade proteins, including blood cascade proteins that are covalently bound to antibodies or antibody fragments, such as Fc. In some embodiments, the blood cascade protein is Factor IX-Fc (FIXFc) or Factor VIII-Fc (FVIIIFc). In some embodiments, one or more proteins of interest are hormones, regulatory proteins and/or neurotrophic factors. Neurotrophic factors are known in the art and include nerve growth factor (NGF), brain-derived neurotrophic factor (BDNF), neurotrophin-3 (NT-3), neurotrophin-4 (NT-4), members of the glial cell line-derived neurotrophic factor ligands (GDNF) and ciliary neurotrophic factor (CNTF). In some embodiments, the protein of interest is neublastin.

In some embodiments, a protein of interest may be, but is not limited to, Abagovomab, Abciximab, Actoxumab, Adalimumab, Adecatumumab, Afelimomab, Afutuzumab, Alacizumab pegol, ALD, Alemtuzumab, Alirocumab, Altumomab pentetate, Amatuximab, Anatumomab mafenatox, Anrukinzumab, Apolizumab, Arcitumomab, Aselizumab, Atinumab, Atlizumab, Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, Cedelizumab, Certolizumab pegol, Cetuximab, Citatuzumab bogatox, Cixutumumab, Clazakizumab, Clenoliximab, Clivatuzumab tetraxetan, Conatumumab, Concizumab, Crenezumab, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Eldelumab, Elotuzumab, Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab, Farletuzumab, Fasinumab, FBTA, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Margetuximab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN, Ticilimumab, Tildrakizumab, Tigatuzumab, TNX, Tocilizumab, Toralizumab, Tositumomab, Tovetumab, Tralokinumab, Trastuzumab, TRBS, Tregalizumab, Tremelimumab, Tucotuzumab celmoleukin, Tuvirumab, Ublituximab, Urelumab, Urtoxazumab, Ustekinumab, Vantictumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab and/or Zolimomab aritox.

Computer Implementations

It should be appreciated that methods disclosed herein may be implemented in any of numerous ways. For example, certain embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a smart phone, tablet, or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools (e.g., MATLAB), and also may be compiled as executable machine language code or intermediate code that is executed on a framework or virtual machine.

In this respect, aspects of the disclosure may be embodied as a computer readable medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other non-transitory, tangible computer storage medium) encoded with information (e.g., Raman signature information) and/or one or more programs that, when executed on one or more computers or other processors, perform methods that implement the various embodiments of the disclosure discussed above. The computer readable medium or media can be transportable, such that the program or programs stored thereon can be loaded onto one or more different computers or other processors to implement various aspects of the present disclosure as discussed above. As used herein, the term "non-transitory computer-readable storage medium" encompasses only a computer-readable medium that can be considered to be a manufacture (e.g., article of manufacture) or a machine.

The terms "program" or "software" are used herein in a generic sense to refer to any type of computer code or set of computer-executable instructions that can be employed to program a computer or other processor to implement various aspects of the present disclosure as discussed above. Additionally, it should be appreciated that according to one aspect of this embodiment, one or more computer programs that when executed perform methods of the present disclosure need not reside on a single computer or processor, but may be distributed in a modular fashion amongst a number of different computers or processors to implement various aspects of the present disclosure.

As used herein, the term "database" generally refers to a collection of data arranged for ease and speed of search and retrieval. Further, a database typically comprises logical and physical data structures. Those skilled in the art will recognize methods described herein may be used with any type of database including a relational database, an object-relational database and an XML-based database, where XML stands for "eXtensible-Markup-Language". For example, Raman spectra information may be stored in and retrieved from a database. The Raman spectra information may be stored in or indexed in a manner that relates culture component levels (e.g., glucose levels) or bioreactor conditions, or with a variety of other relevant information.

Computer-executable instructions may be in many forms, such as program modules, executed by one or more computers or other devices. Generally, program modules include routines, programs, objects, components, data structures, etc. that perform particular tasks (e.g., tasks relating to Feedback control) or implement particular abstract data types. Typically the functionality of the program modules may be combined or distributed as desired in various embodiments.

The present disclosure is further illustrated by the following Examples, which in no way should be construed as further limiting. The entire contents of all of the references (including literature references, issued patents, published patent applications, and co pending patent applications) cited throughout this application are hereby expressly incorporated by reference, in particular for the teaching that is referenced hereinabove.

The present disclosure is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

Raman spectroscopy was used for real time prediction of parameters including nutrient, metabolic waste and cell growth parameters within a mammalian cell culture setting. Components such as glucose, lactate, glutamate, ammonia and osmolality were robust in validation batch predictions and cross-scale applications.

Example 1: Materials and Methods

Bioreactor Cultures

Twenty cell culture process runs across three different stirred-tank bioreactor scales were used: 5 L Applikon (Applikon Biotechnology, The Netherlands) bench-scale glass bioreactors (n=13), 200 L custom ABEC (ABEC Inc., Bethlehem, Pa.) pilot-scale stainless steel bioreactors (n=4), and 2000 L custom ABEC manufacturing-scale stainless steel bioreactors (n=3). Here, a 13 day fed-batch process producing a monoclonal antibody via a CHO cell line is described. The process utilizes a proprietary chemically defined basal media solution with fixed amounts of daily nutrient feed (also chemically defined) and an option to add additional glucose stock if necessary, based on batch performance. The pH, temperature, and dissolved oxygen were controlled.

Bench-scale 5 L runs varied key process parameters to build process robustness into the dataset including +10% high volume feed (n=2), −10% low volume feed (n=2), +25% high initial seed density (n=3), and −25% low initial seed density (n=4). The dataset incorporated two control condition batches from the 5 L scale as well. All pilot and manufacturing-scale runs served as control process runs contributing scale-specific data into the model while applying traditional scale-up parameters such as power per volume and $k_La$ mass transfer to the selection of agitation and aeration strategies.

Cell Culture Sample Collection and Offline Analysis

Bench-scale runs were manually sampled a minimum of twice per day. Two of the pilot-scale runs were sampled six times per day by a BaychroMAT® inline automated sampling device (Bayer Technology Services GmbH, Leverkusen, Germany) coupled with an inline Cedex HiRes cell counter (Roche Custom Biotech, Roche Diagnostics, Indianapolis, Ind.) for cell density and viability analysis followed by inline 0.22 µm sterile filtering apparatus ultimately leading to a 2-8° C. chilled fraction collector. Two additional pilot-scale runs, as well as manufacturing-scale runs, were sampled manually three times per day. All samples were run on a Nova Biomedical BioProfile Flex metabolite analyzer (Nova Biomedical Corporation, Waltham, Mass.) measuring glucose, lactate, glutamate, ammonium, and osmolality. Cell density and viability data were measured for each sample using a Cedex cell counter (Roche Custom Biotech, Roche Diagnostics, Indianapolis, Ind.) involving a trypan blue exclusion assay except for the two pilot-scale runs, which utilized the inline Cedex HiRes instrument which employed the same trypan blue exclusion method but has a higher resolution camera than the Cedex instrument. The culture samples across the three scales were analyzed by the cell counting and metabolite analyzer equipment immediately upon collection except in the case of the two pilot-scale batches in which the automatic sampling device operated by pulling samples twenty four hours a day at an interval of 6 hours. The continuous nature of the auto-sampling device allowed for overnight sampling, filtration, and temperature controlled storage of the samples. On a daily basis, collected samples were analyzed on the BioProfile Flex instrument for metabolite measurements.

Collection of Raman Spectra

Raman spectra representing inelastic photon scattering data across a 150-3425 cm-1 wavenumber range were collected in situ during all process runs using a Kaiser RamanRxn2 analyzer (Kaiser Optical Systems Inc., Ann Arbor, Mich.). The base unit was comprised of an Invictus 785 nm laser excitation, an axial transmissive spectrograph with a HoloPlex transmission grating (Kaiser Optical Systems, Inc., Ann Arbor, Mich.), and a cooled charged-coupled device (CCD) detector maintained at −40° C. The base unit was connected to the sample location using fiber optics and application-optimized Raman probes. Bench-scale runs utilized bIO-LAB-220 (Kaiser Optical Systems Inc., Ann Arbor, Mich.) top-mounted vertical stainless steel immersion probes inserted in the glass vessels with standard threaded adaptors and aseptic boundary gaskets whereas pilot and manufacturing-scale runs utilized bIO-PRO (Kaiser Optical Systems, Inc., Ann Arbor, Mich.) stainless steel immersion probes secured with Ingold connections. Raman probes contained the same sapphire window material. Spectral acquisitions utilizing cosmic ray removal and intensity correction, both of which are standard options within iC Raman 4.1 Software (Mettler Toledo Autochem, Columbia, Md.), consisted of the co-addition of 600 individual spectral acquisitions at 1 second of exposure time each, resulting in 10 minutes total exposure time per spectrum.

Spectral Preprocessing and Multivariate Modeling

Univariate-Y, multivariate-X predictive component models were built from spectral data collected during fed-batch cell culture processing within bioreactors at the three respective scales; bench-scale (5 L), pilot-scale (200 L) and manufacturing-scale (2000 L). No spectral data collected off line or via reference solutions of chemically defined media or nutrient solutions were employed. Spectra exported from the Kaiser RamanRxn2 instrument as .spc files were aligned with offline instrument data in a spreadsheet format that served as an input file for SIMCA 12 (Umetrics Inc., San Jose, Calif.). Within SIMCA, mathematical pre-processing methods were applied to all X-block cell culture spectra including $1^{st}$ derivative Savitzky-Golay smoothing with 15 $cm^{-1}$ point spacing and a quadratic polynomial followed by Standard Normal Variate (SNV), and mean-centering. Y-block reference component data was treated with unit-variance scaling (UV). SIMCA was then used for multivariate analysis and partial least square (PLS) modeling to find a correlation between X and Y blocks on a component by component basis for all measured values from the Cedex cell counting and Nova Flex metabolite analyzer instruments. Y-block reference data outliers were identified and removed through analysis of scores plots, loading plots, residual plots, and Hotelling's $T^2$ plots within SIMCA. The variable influence on projection (VIP) algorithm, which ranks the importance of the X-variables (spectral regions) taking into consideration the amount of explained variation in the Y-component variance (offline measurements), was calculated within SIMCA software and used to determine relative correlation of spectral regions throughout the full Raman shift range with offline data. Spectral region selection criteria were set at VIP≥1.0 as terms with larger VIP values, especially larger than 1.0, are the most significant in correlation with Y-block data. An example of the process flow used to generate the PLS models is illustrated in FIG. 1, which shows the process flow diagram for data preprocessing, multivariate model building, optimization, and selection criteria for generated PLS models. This guideline includes the types and sequence of data preprocessing and normalization in addition to the iterative outlier removal and region selection rules followed. The criteria determining whether an optimized model was reached within the model building process was strategically focused solely on minimizing the root mean squared error of prediction (RMSEP) of the validation dataset of interest with a two pass iteration limitation placed on each of the possible outlier removal steps to support a rapid pace of model development.

Example 2: Scale-Specific Modeling

An assessment of the scale-up predictability of the technology was performed using six dataset combinations targeting permutations of the process scales (5 L, 200 L, and 2,000 L) to generate PLS calibration models which were evaluated while targeting a manufacturing-scale batch as a validation data set.

For each offline measured Y-block component, calibration data sets were created using the following scenarios: bench-scale data only, pilot-scale data only, bench-scale plus pilot-scale data, bench-scale plus pilot-scale data plus manufacturing-scale data. In one scenario, three iterations were created in order to use each of the three manufacturing data sets as an external validation set while including the other two. PLS model calibration statistics of these six designs, tracking parameters such as number of sample observations used (to reflect the size of the calibration models as well as the extent of dataset reduction resulting from outlier removal steps during model generation), number of PLS model factors, R2 (the percent of variation of Y-block reference data explained by the model), and Q2 (the percent of variation of Y-block reference data predicted by the model according to a leave-one-sample-out style internal cross validation) are illustrated in Table 1. An example of PLS model validation results, illustrated in Table 2, where each of the six calibration models, outlined in Table 1, were used to predict a single manufacturing-scale batch. The validation parameters tabulated include root mean squared error of estimation (RMSEE), root mean squared error of cross validation (RMSECV), root mean squared error of prediction (RMSEP) and average percent error between measured and predicted values.

Figure 2A:
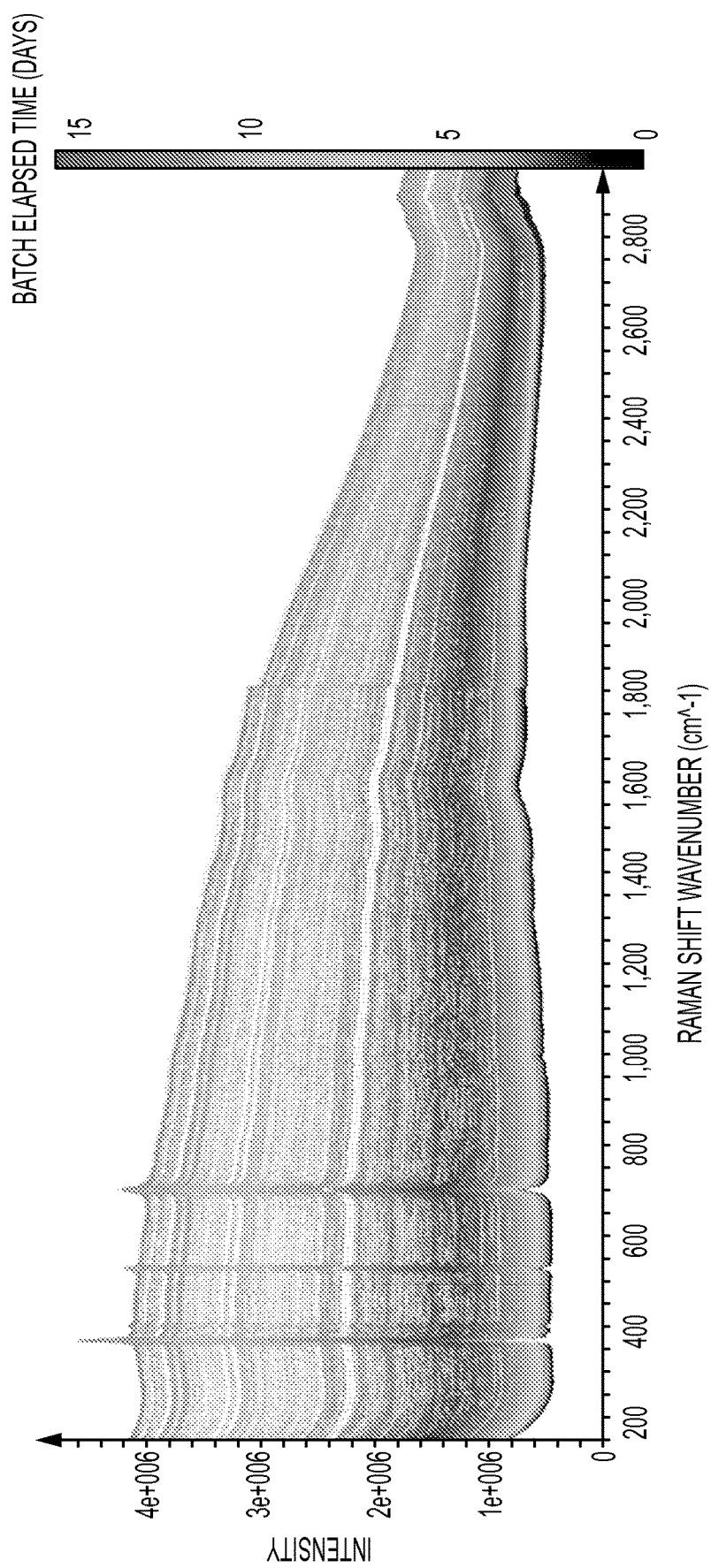
FIG. 2A is a non-limiting example of a manufacturing-scale time course spectra shaded by batch elapsed time (raw)
Figure 2B:
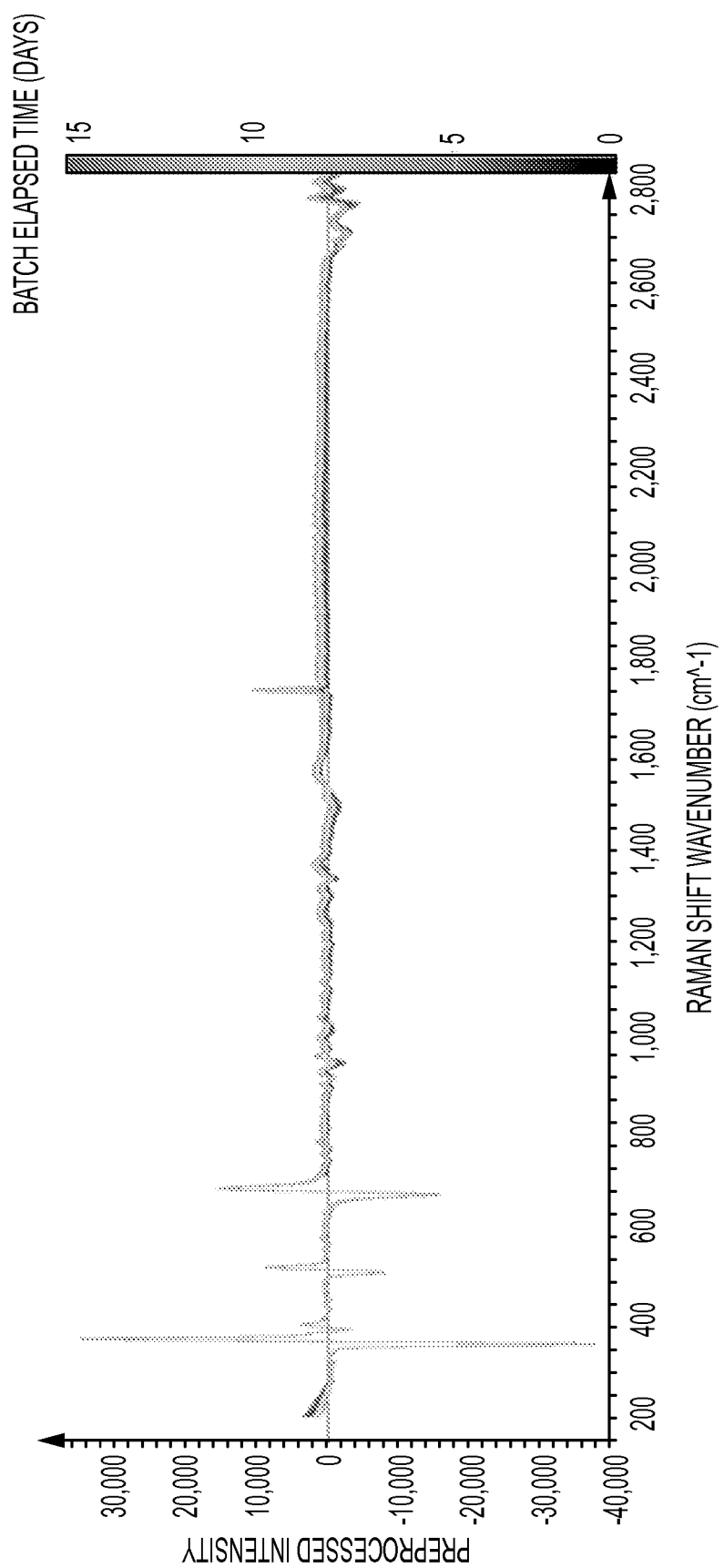
FIG. 2B is a non-limiting example of a manufacturing-scale time course spectra shaded by batch elapsed time (preprocessed with 1st derivative only)
Figure 2C:
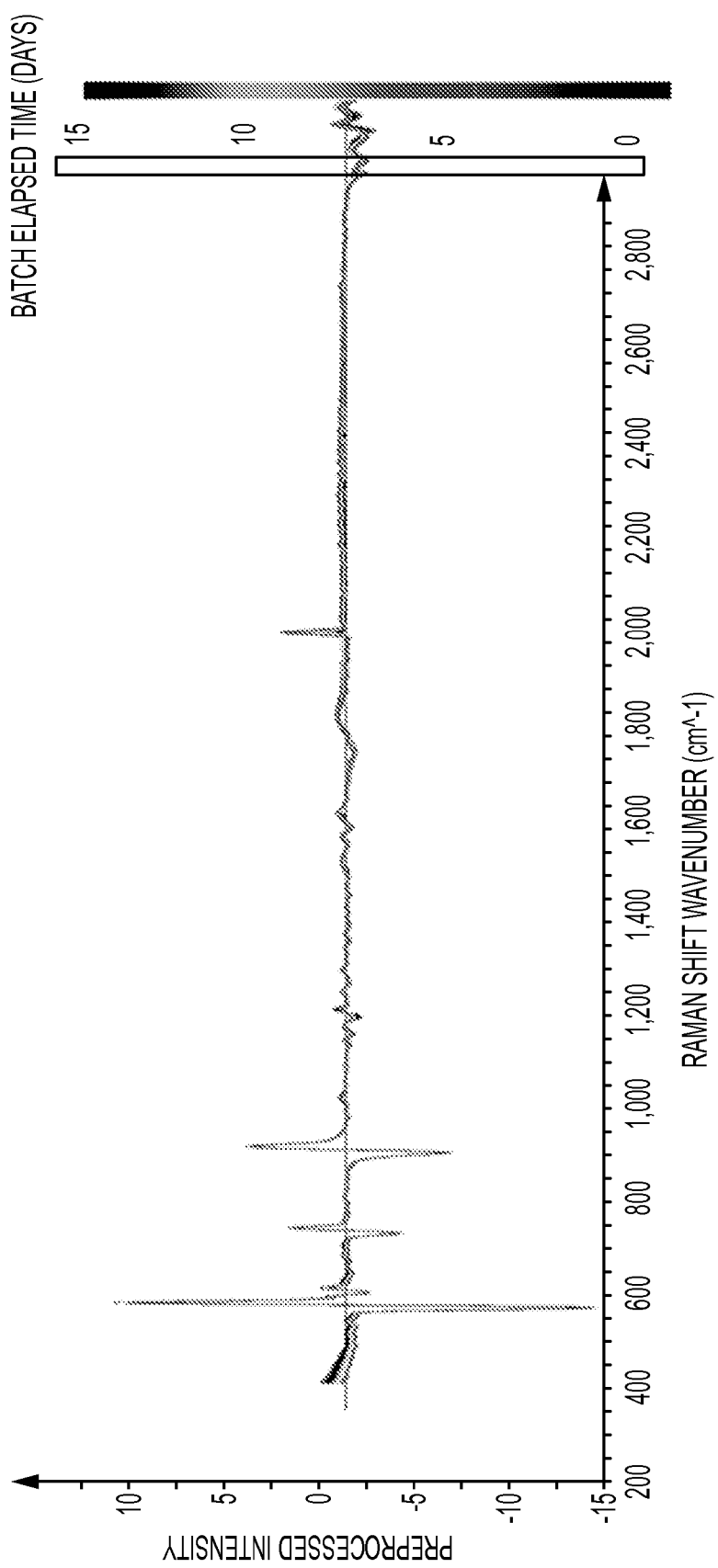
FIG. 2C is a non-limiting example of a manufacturing-scale time course spectra shaded by batch elapsed time (preprocessed with 1st derivative, Savitzky-Golay and SNV)

Approximately one thousand Raman spectra were captured during a manufacturing batch, illustrated in FIGS. 2A-C, in different forms. In one form, FIG. 2A, the raw spectra illustrate that shift is relatively minimal during the first six days of the process but increases at a faster rate following day 6. In another form, FIG. 2B, the 1st derivative preprocessed spectra removes much of the intensity variation across the full spectrum, and in yet another form, FIG. 2C, the 1st derivative, Savitzky-Golay and SNV preprocessed spectra lead to further normalization.

Figure 3A:
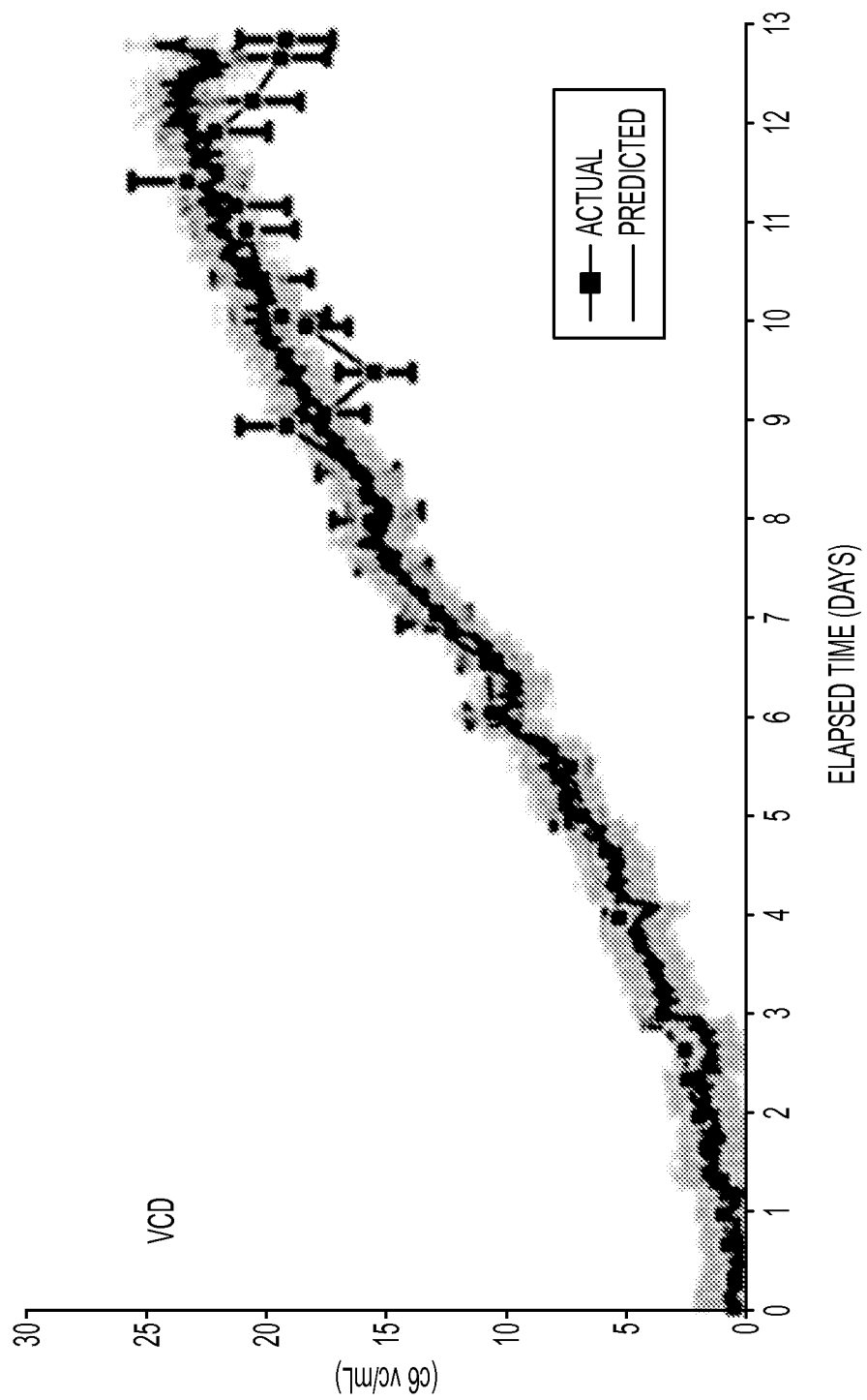
FIG. 3A is a non-limiting example of PLS model prediction results, predicting a single 2,000 L manufacturing-scale validation batch for VCD.
Figure 3B:
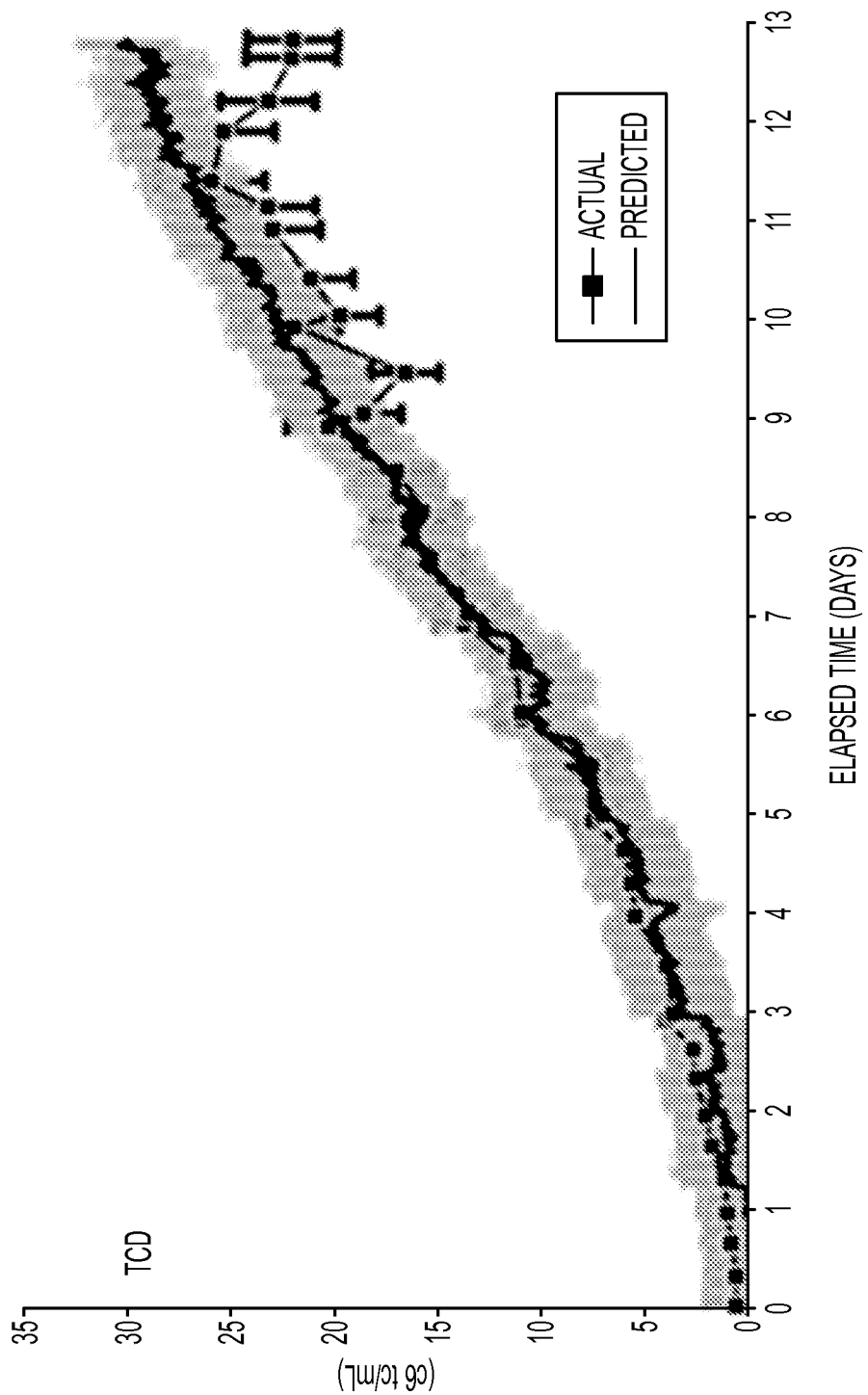
FIG. 3B is a non-limiting example of PLS model prediction results, predicting a single 2,000 L manufacturing-scale validation batch for TCD.
Figure 3C:
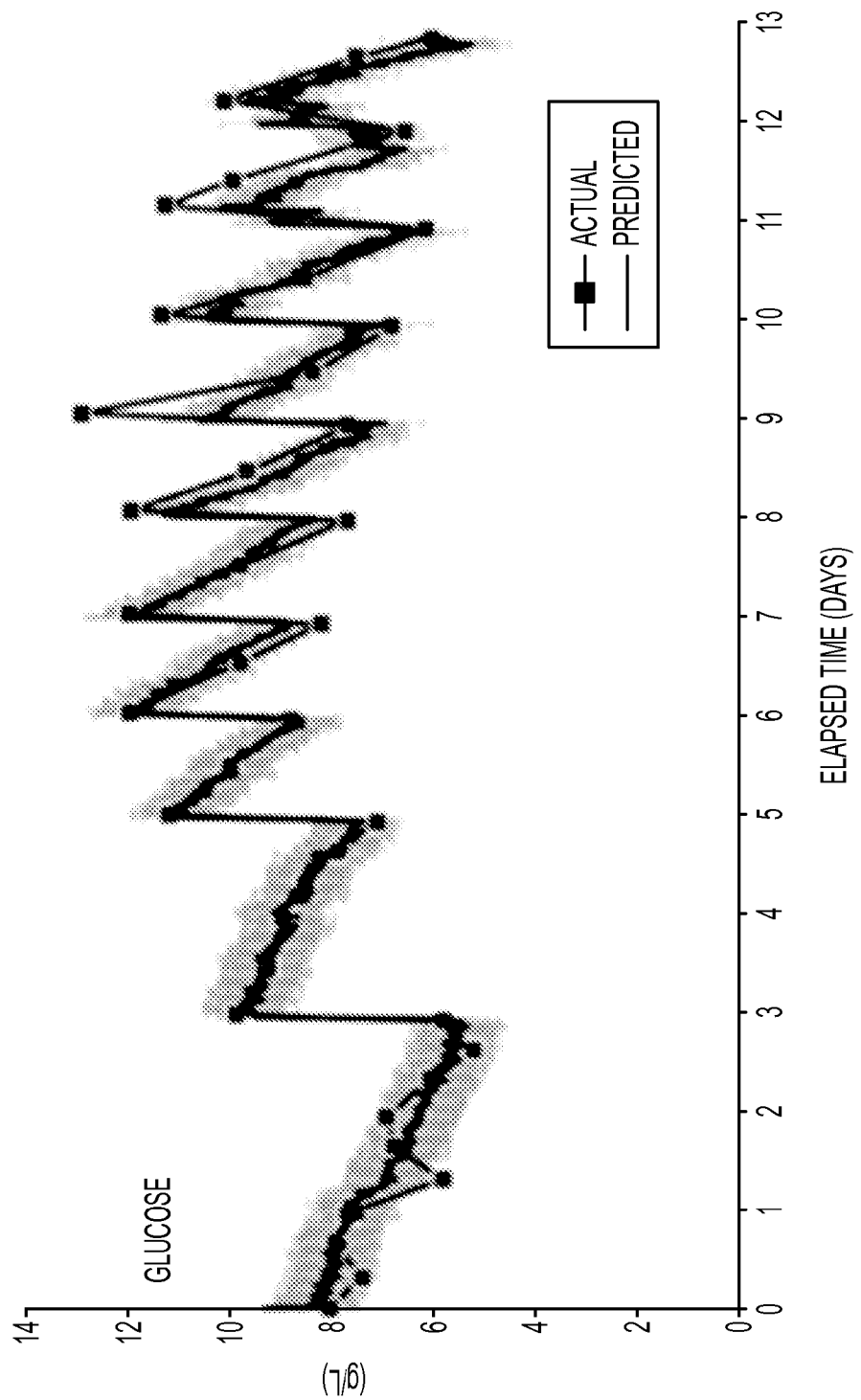
FIG. 3C is a non-limiting example of PLS model prediction results, predicting a single 2,000 L manufacturing-scale validation batch for glucose.
Figure 3D:
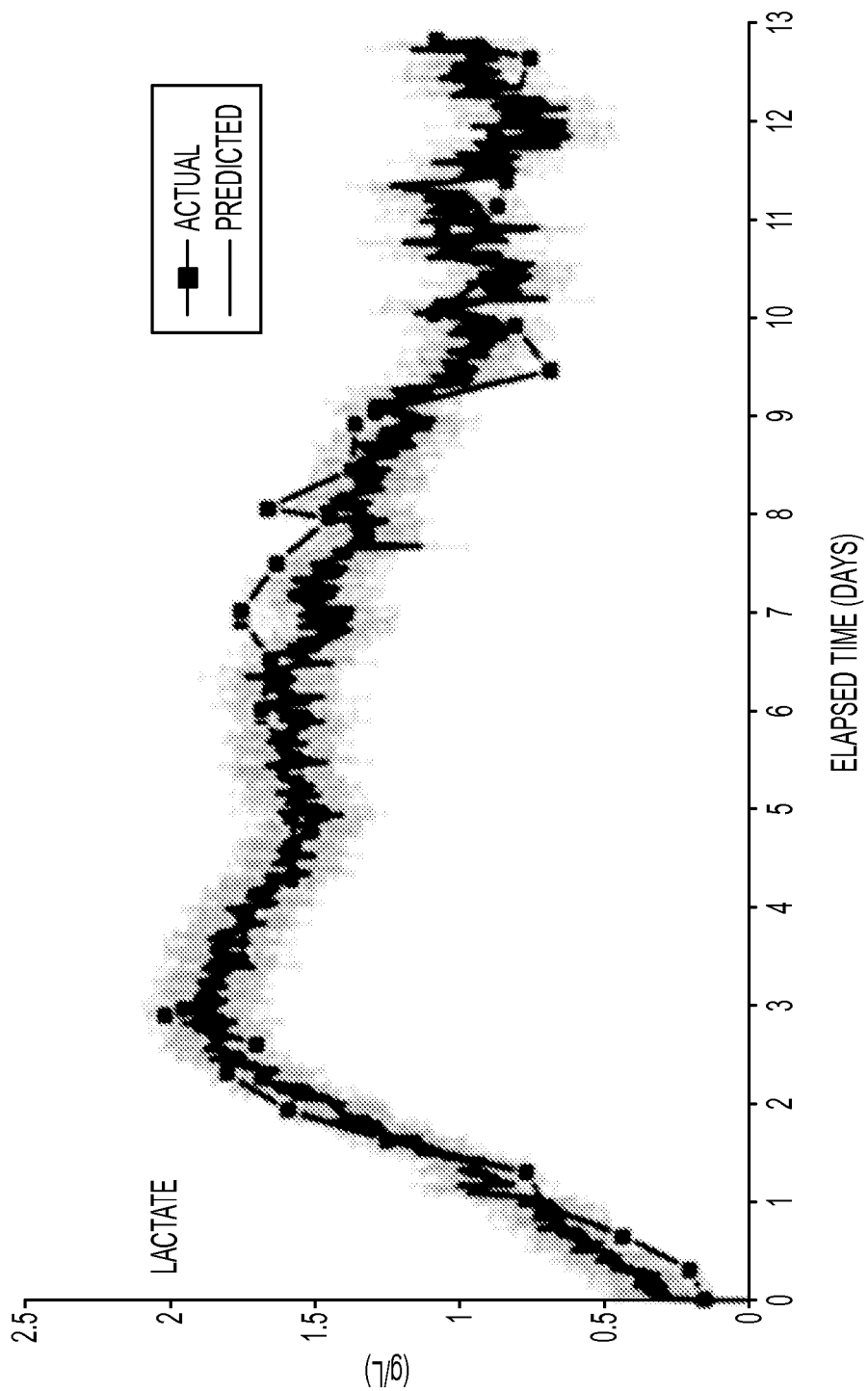
FIG. 3D is a non-limiting example of PLS model prediction results, predicting a single 2,000 L manufacturing-scale validation batch lactate.
Figure 3E:
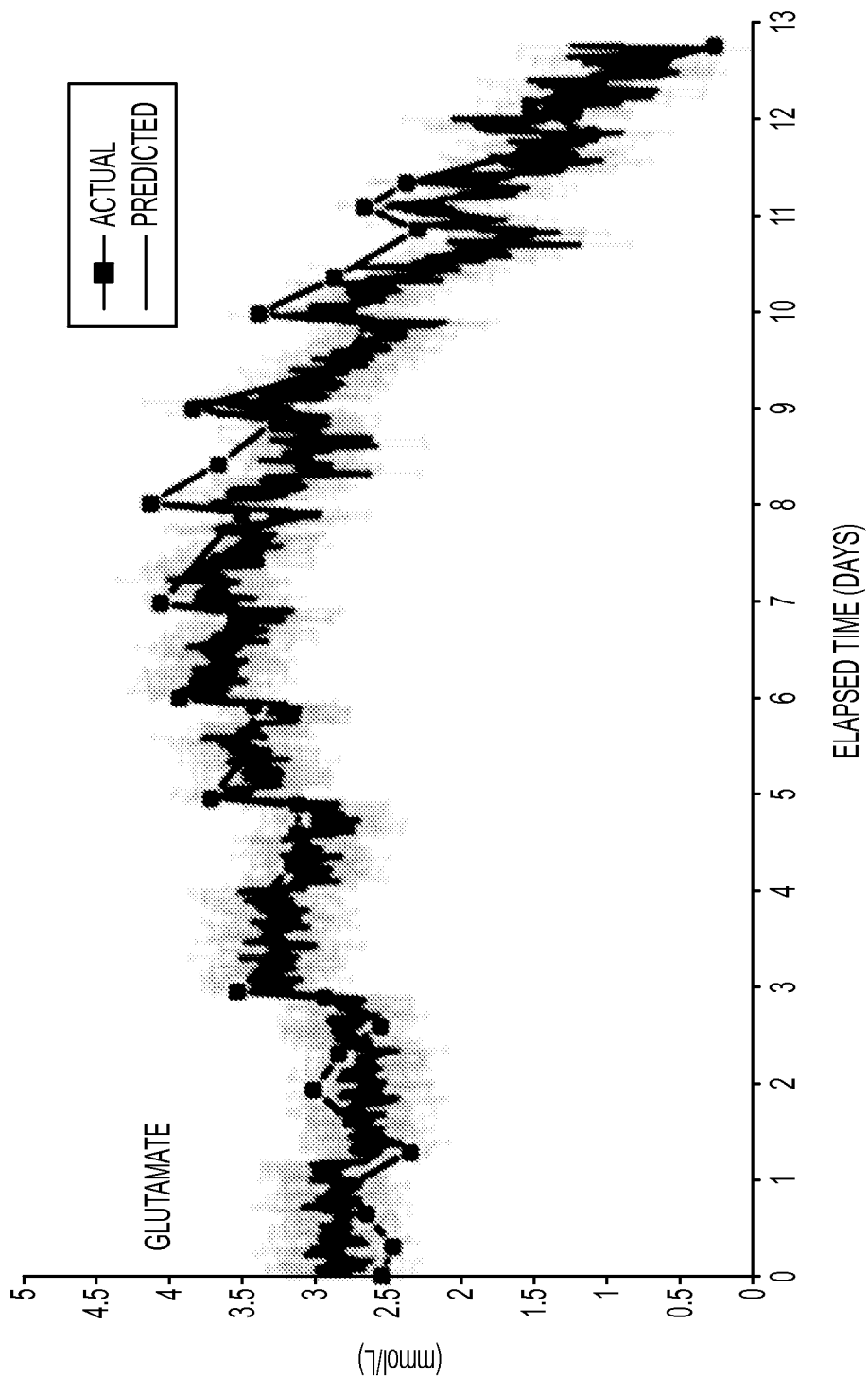
FIG. 3E is a non-limiting example of PLS model prediction results, predicting a single 2,000 L manufacturing-scale validation batch for glutamate.
Figure 3F:
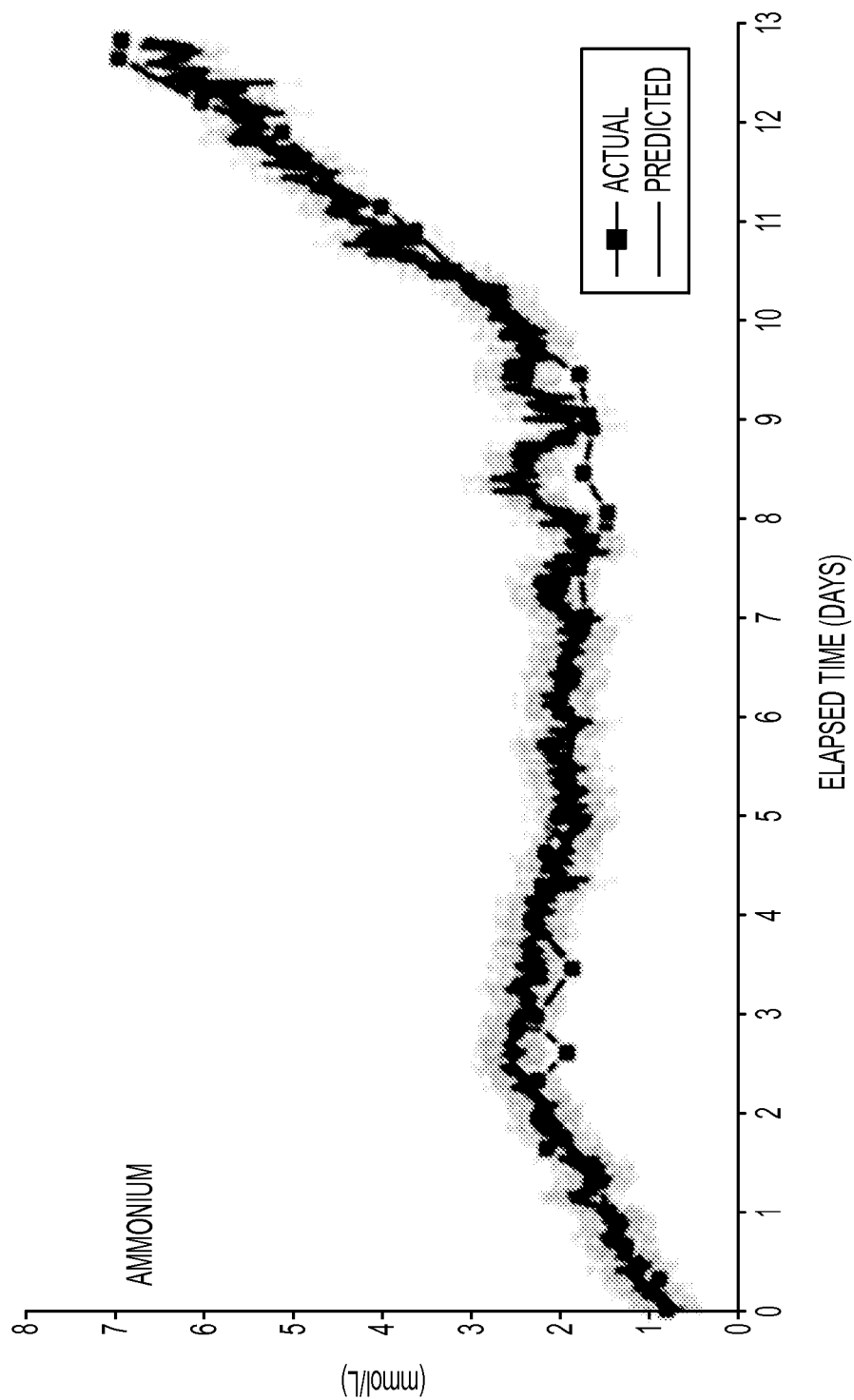
FIG. 3F is a non-limiting example of PLS model prediction results, predicting a single 2,000 L manufacturing-scale validation batch for ammonium.
Figure 3G:
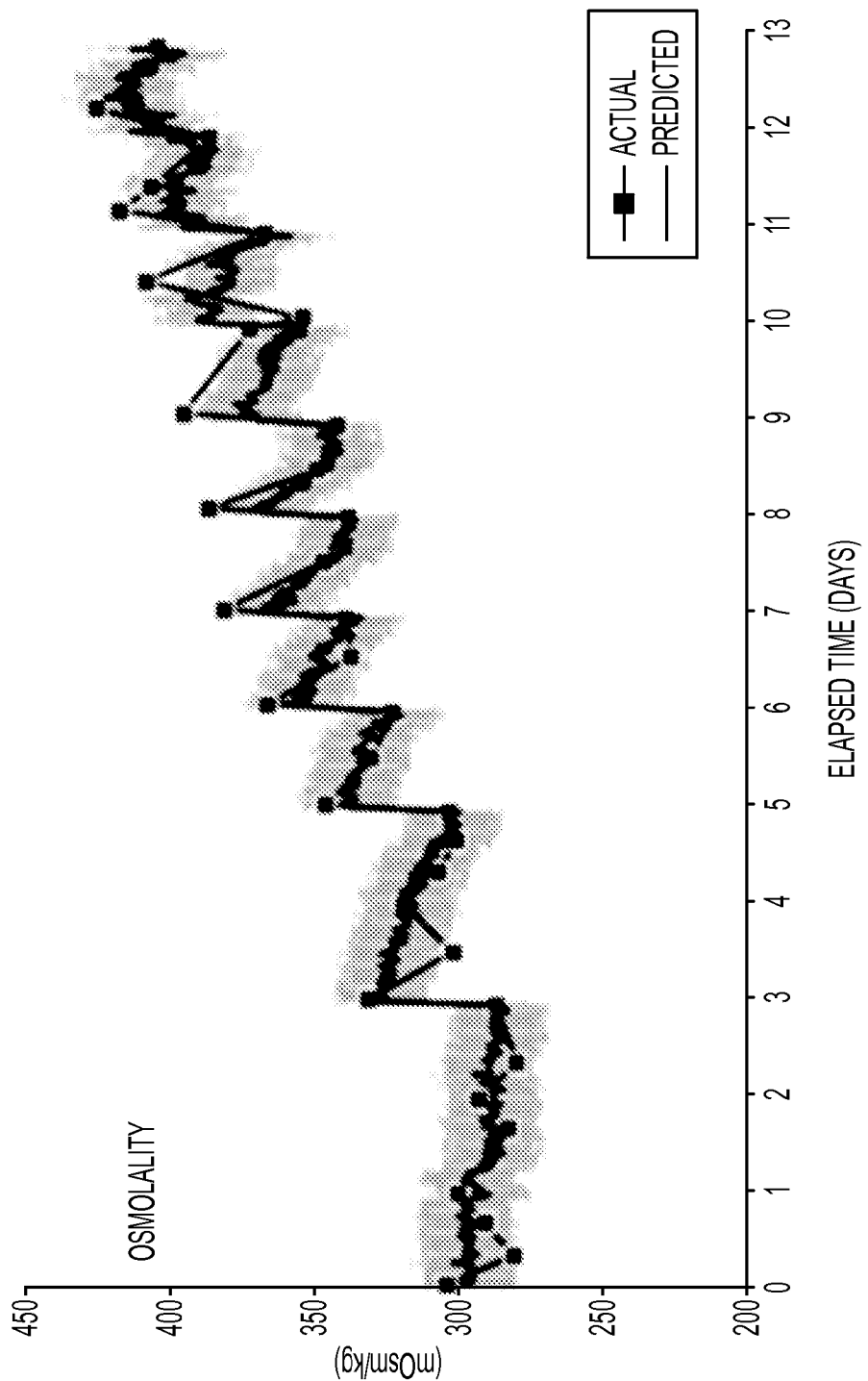
FIG. 3G is a non-limiting example of PLS model prediction results, predicting a single 2,000 L manufacturing-scale validation batch osmolality.

Time course prediction trends of a manufacturing batch using a calibration model built from bench-scale, pilot-scale, and two manufacturing batches were used to evaluate; VCD, TCD, glucose, lactate, glutamate, ammonium, and osmolality. PLS model prediction results were obtained from calibration data containing bench-scale, pilot-scale, and manufacturing-scale (batch 1 and 2) predicting a single 2,000 L manufacturing-scale validation batch (batch 3) for VCD (FIG. 3A), TCD (FIG. 3B), glucose (FIG. 3C), lactate (FIG. 3D), glutamate (FIG. 3E), ammonium (FIG. 3F), and osmolality (FIG. 3G). In FIGS. 3A-G, square-dotted trends represent measured values (actual), black trends represent PLS model predictions, and gray error bars around all black prediction trends visualize PLS model root mean squared error of prediction (RMSEP) for each component model, a fixed value error. The square-dotted trend lines (actual) of FIGS. 3A and 3B contain error bars around measured VCD and TCD values, indicating an assumed 10% measurement variability of Cedex cell counter, a fixed percent error.

Figure 4:
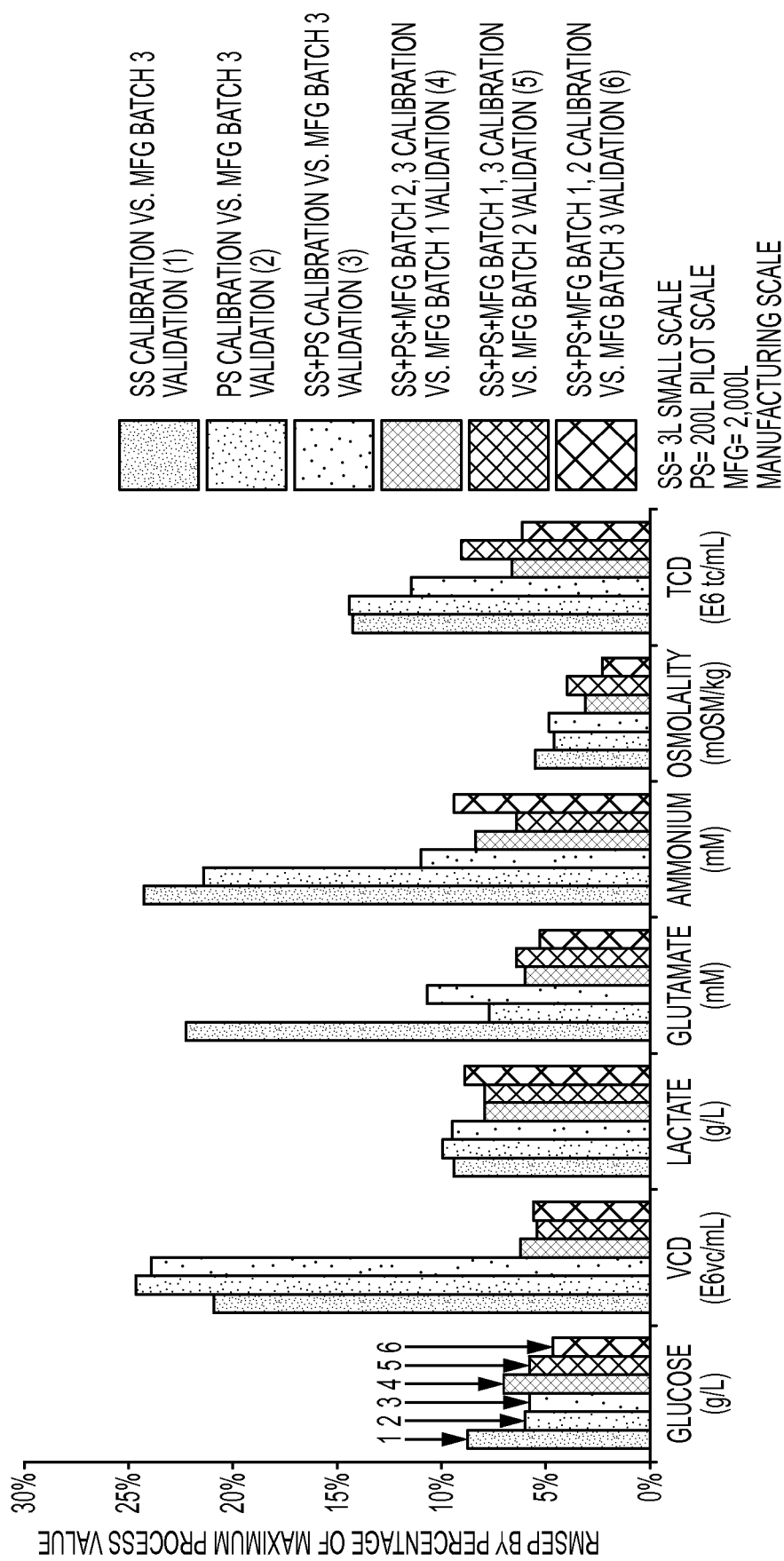
FIG. 4 is a non-limiting example of a root mean squared error of prediction (RMSEP) across various single-scale and combination-scale models.

The root mean squared error of prediction (RMSEP) was determined as a percentage of maximum process value for each component to assess predictive performance of the models across different single scales and combinations of scales. As illustrated in FIG. 4, glucose, lactate and osmolality models predicted at or below 10% relative RMSEP regardless of the combination of scale-specific data that were built in.

Figure 5A:
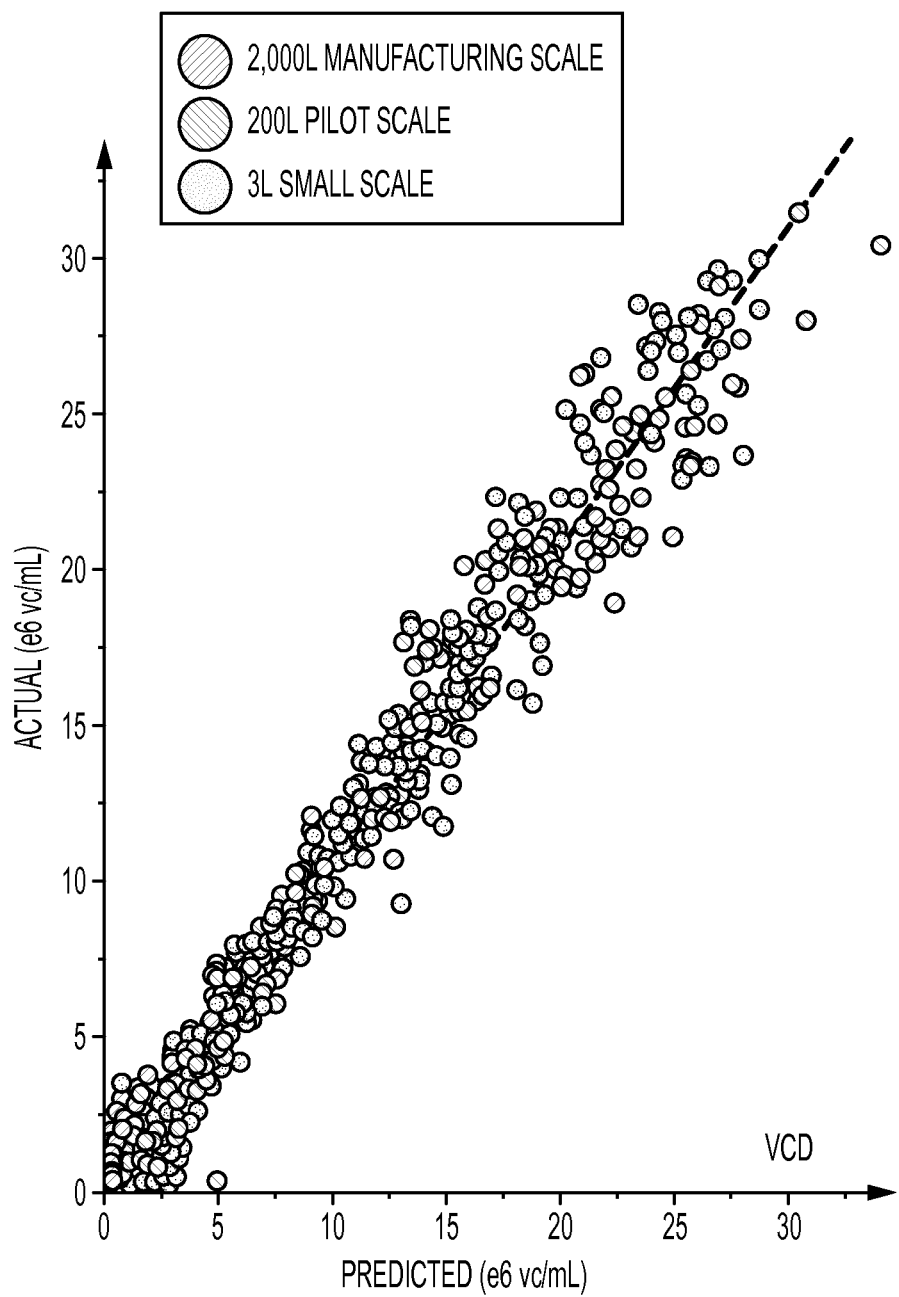
FIG. 5A is a non-limiting example of a calibration model of actual (offline reference data) versus predicted (PLS model generated) values across various culture processing scales for VCD.
Figure 5B:
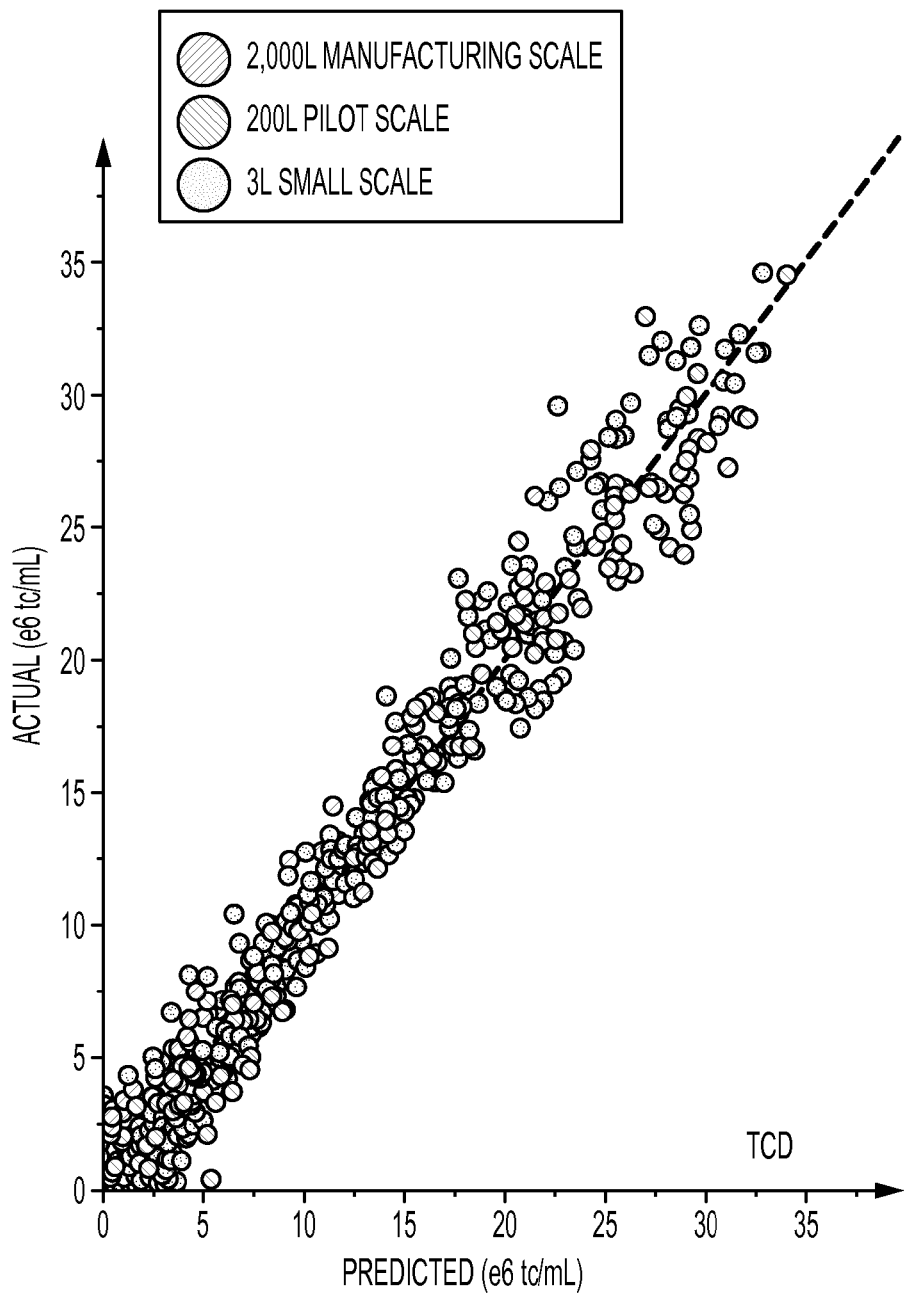
FIG. 5B is a non-limiting example of a calibration model of actual (offline reference data) versus predicted (PLS model generated) values across various culture processing scales for TCD.
Figure 5C:
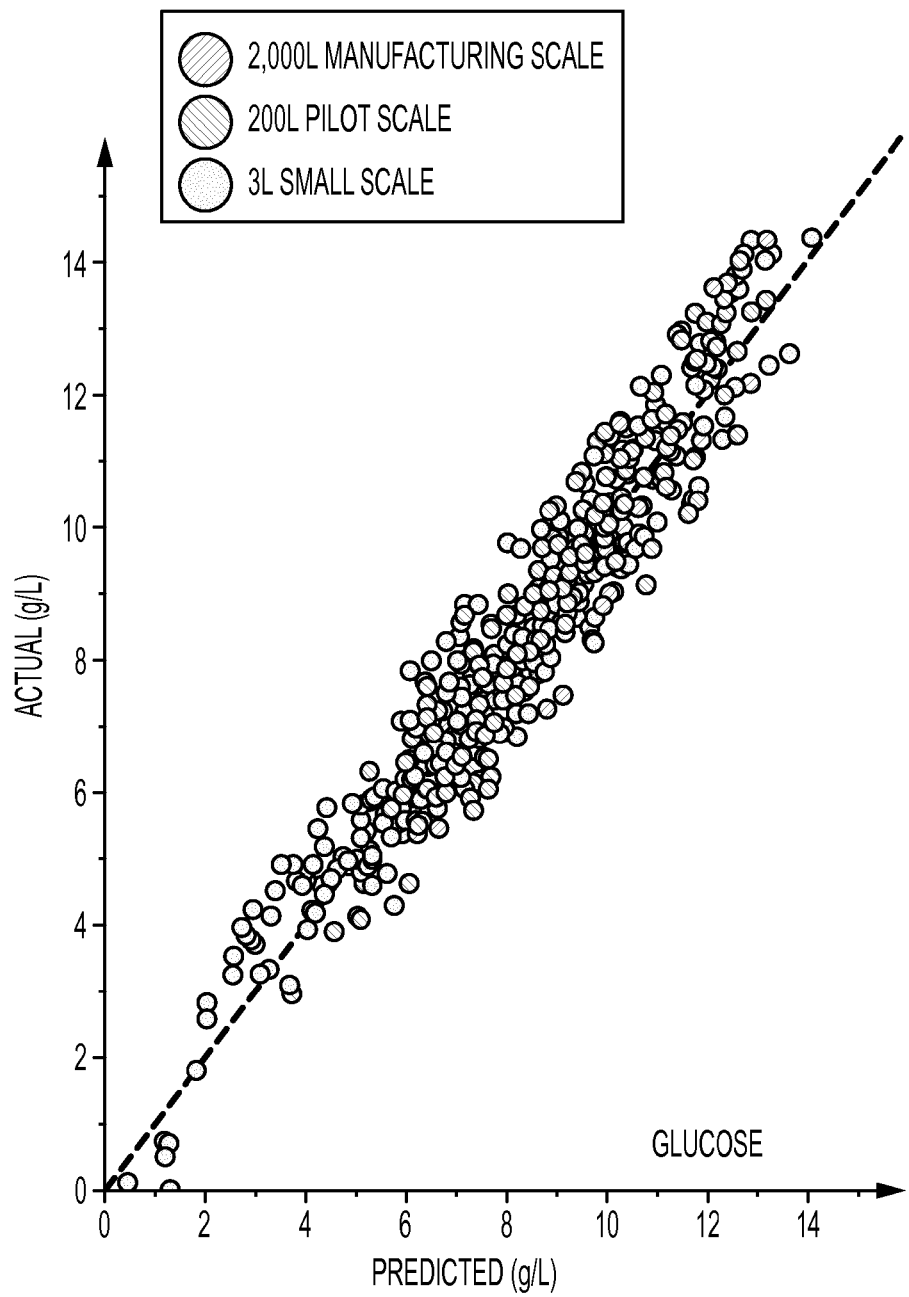
FIG. 5C is a non-limiting example of a calibration model of actual (offline reference data) versus predicted (PLS model generated) values across various culture processing scales for glucose.
Figure 5D:
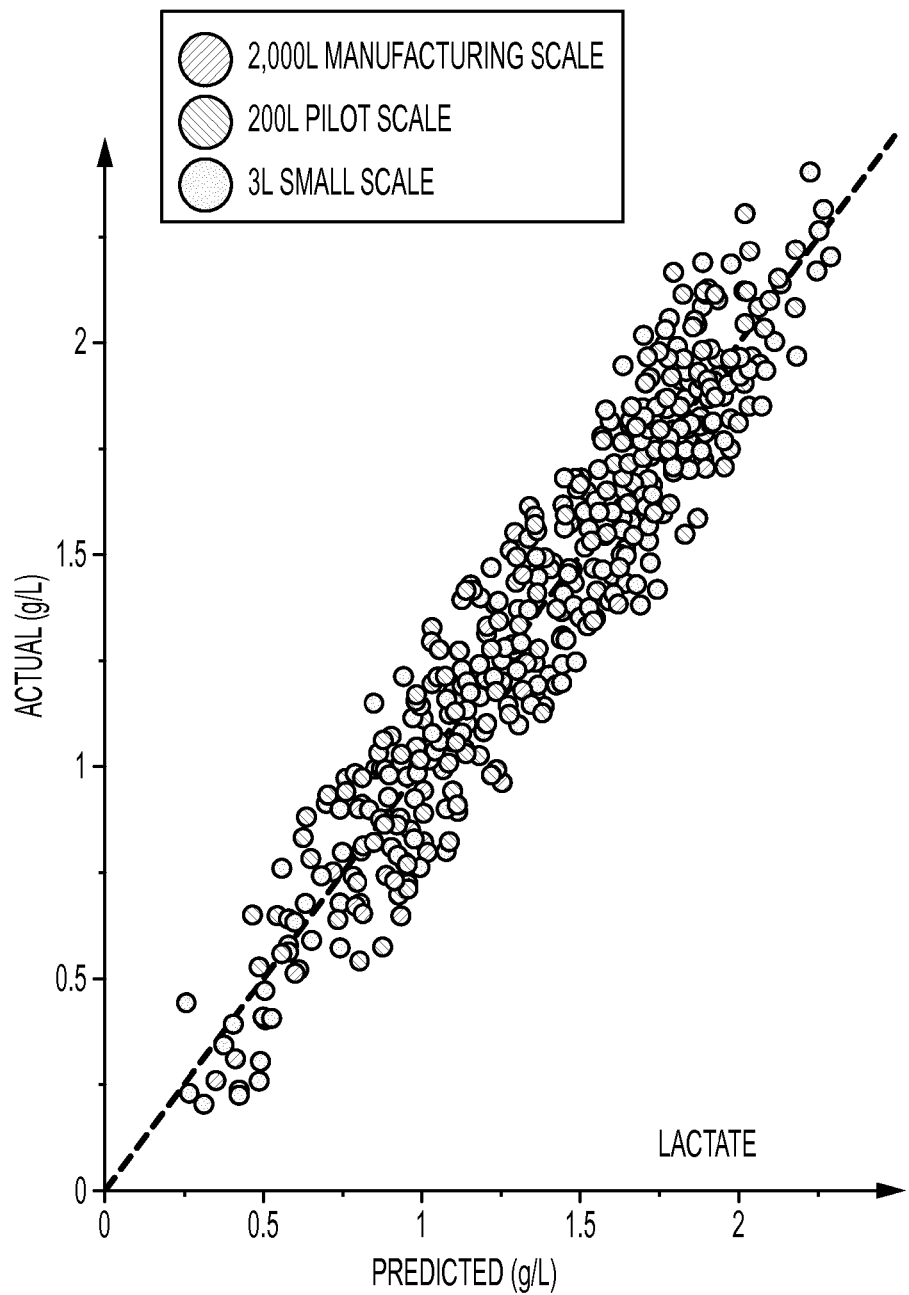
FIG. 5D is a is a non-limiting example of a calibration model of actual (offline reference data) versus predicted (PLS model generated) values across various culture processing scales for lactate.
Figure 5E:
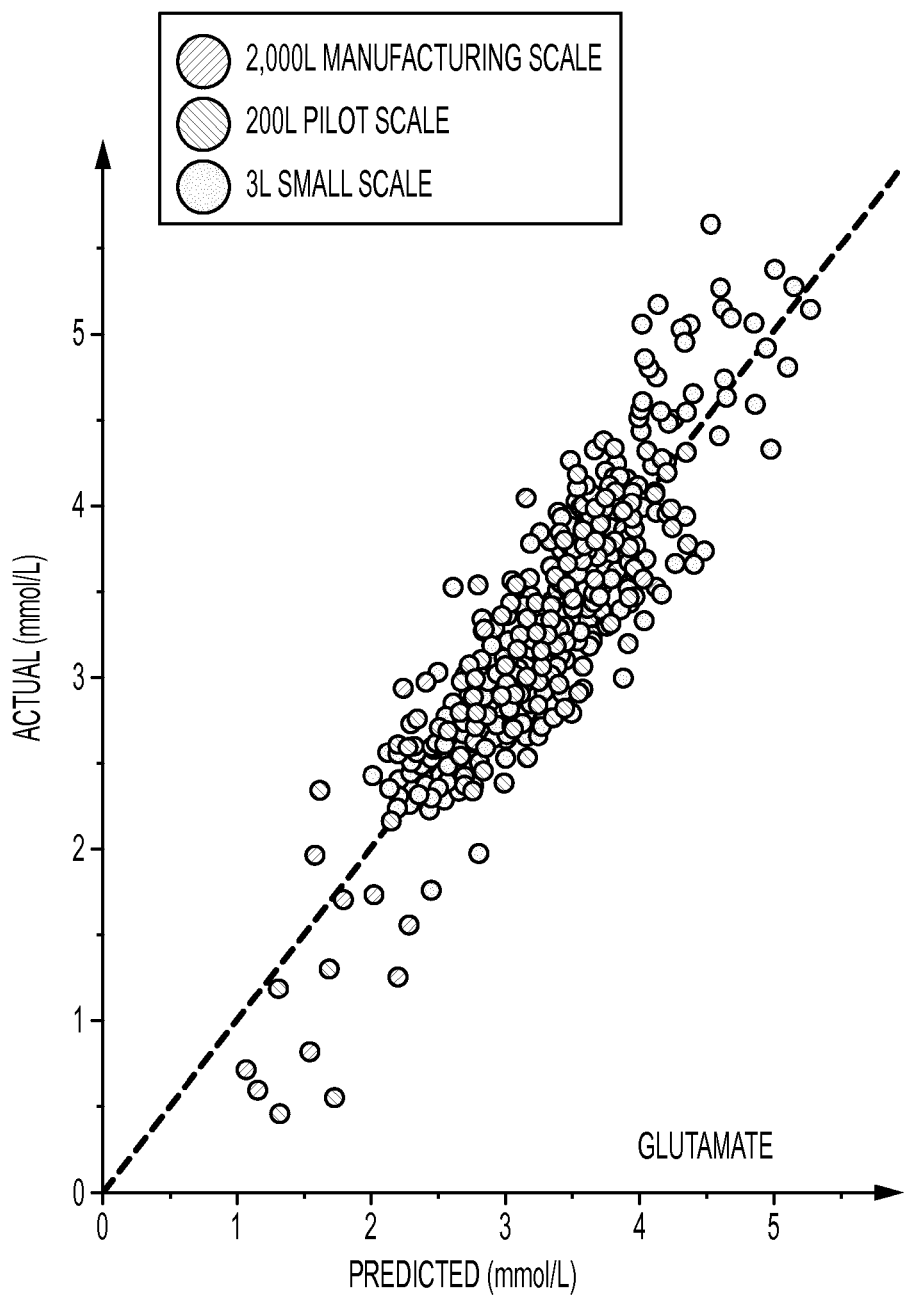
FIG. 5E is a non-limiting example of a calibration model of actual (offline reference data) versus predicted (PLS model generated) values across various culture processing scales for glutamate.
Figure 5F:
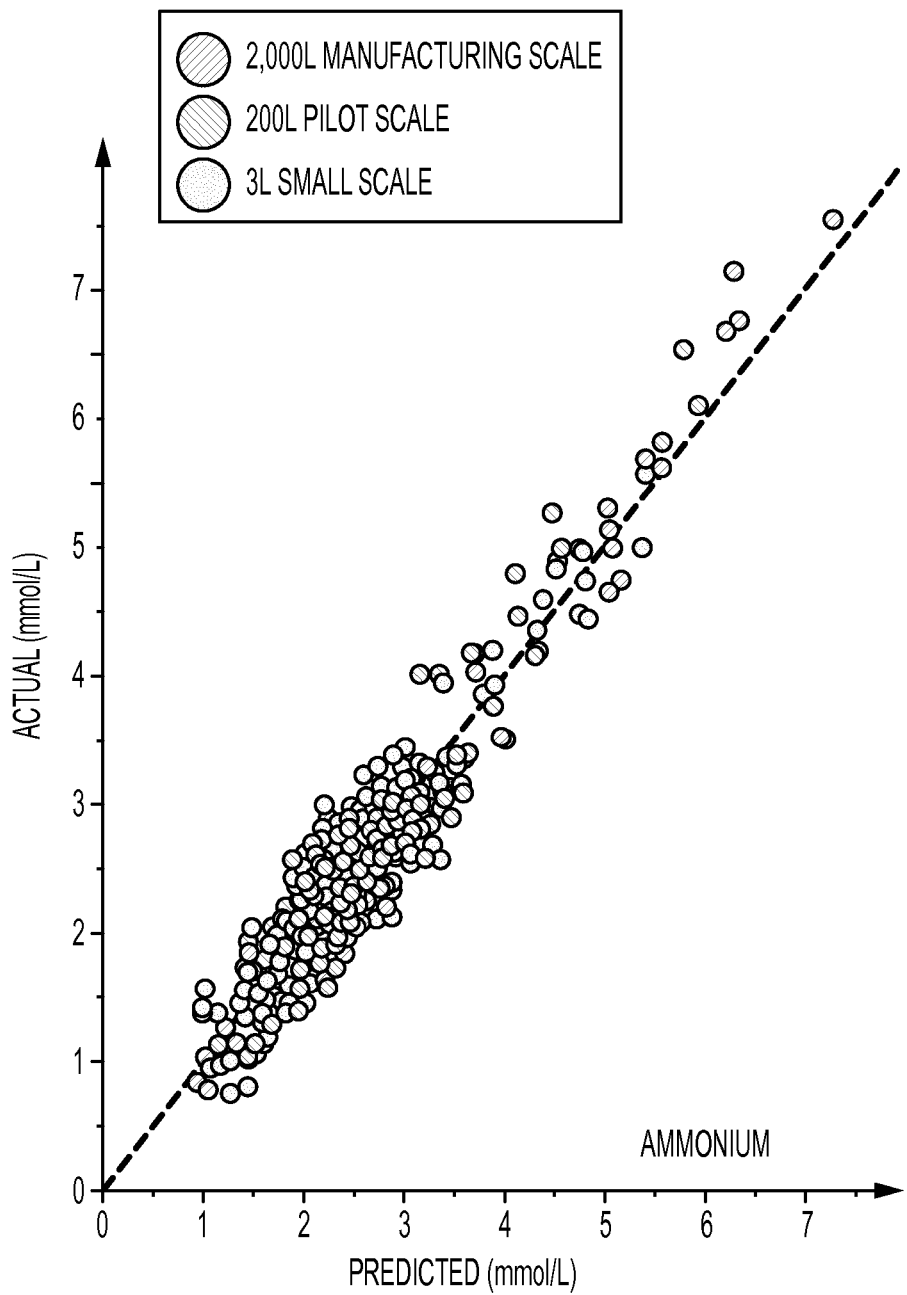
FIG. 5F is a non-limiting example of a calibration model of actual (offline reference data) versus predicted (PLS model generated) values across various culture processing scales for ammonium.
Figure 5G:
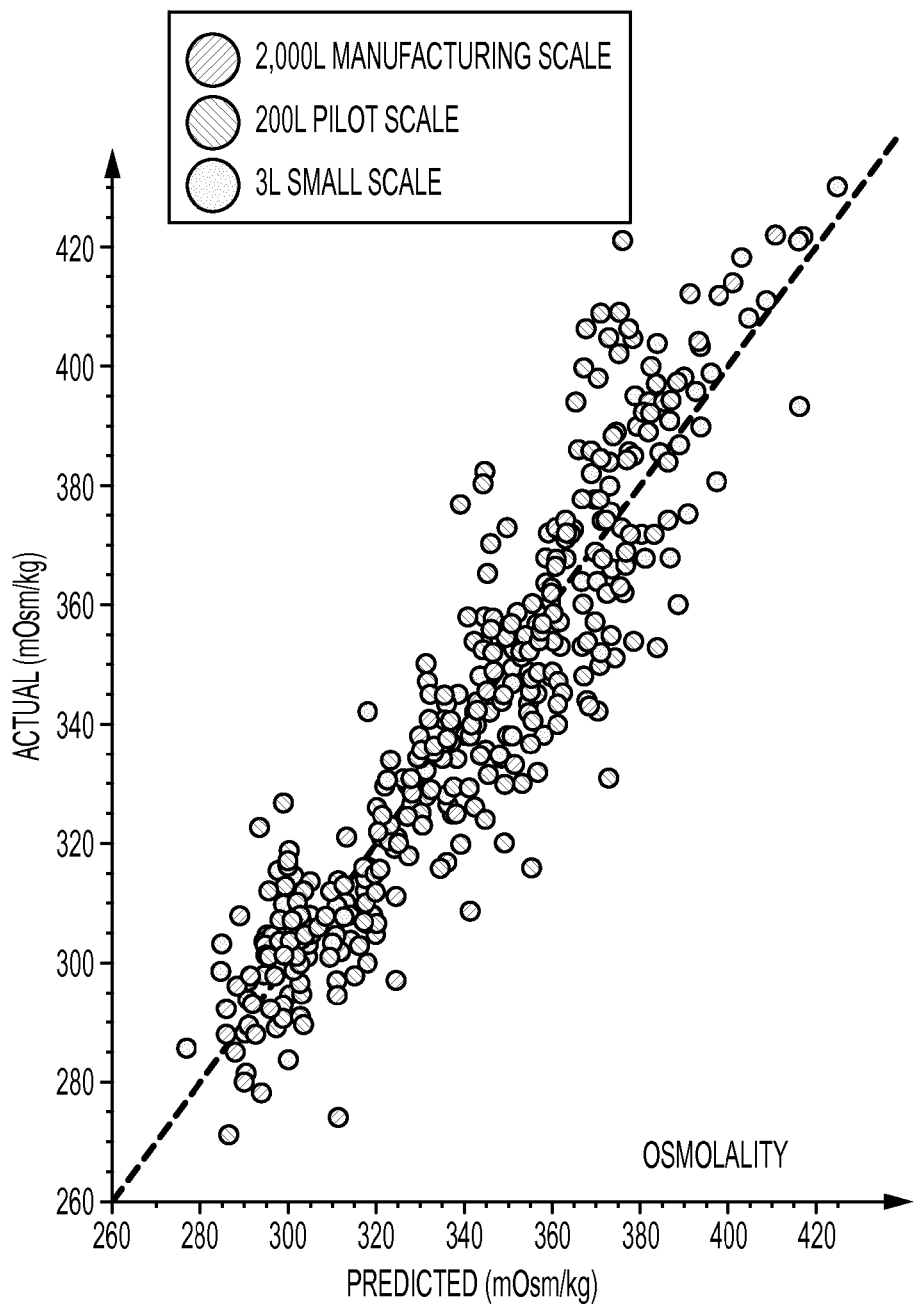
FIG. 5G is a non-limiting example of a calibration model of actual (offline reference data) versus predicted (PLS model generated) values across various culture processing scales for osmolality.

PLS models were generated and used to analyze effectiveness in cross-scale models such as in the VCD and TCD prediction capabilities where it may be advantageous to include at-scale data to decrease the prediction error for the manufacturing-scale validation batch. Thus, in some embodiments, the components of viable cell density (VCD) and total cell density (TCD) were predicted with at-scale manufacturing data included into the model. In one embodiment, relative RMSEP trends for glutamate and ammonium models, as shown in FIG. 4, demonstrate a level of scale-dependency similar to those observed in VCD and TCD. Evaluation of the concentration range captured for glutamate and ammonium components by each scale's set of runs, as illustrated in the observed vs. predicted linearity trends of FIGS. 5E-F, show that the manufacturing runs had minimum and maximum values similar to pilot-scale runs but stretch out wider than the minimum and maximum values captured in small scale runs. In some embodiments, therefore, it is desirable to use models based on a range of concentration values of particular components that will be experienced in the prediction context (e.g., at a manufacturing-scale).

Example 3: Lactate Assessment

Raman spectroscopy was used for prediction of lactate levels in a bioreactor culture. Sodium L-lactate solution, procured from SIGMA (>99% sodium L-lactate P/N 71718), was spiked into chemically defined cell culture media. The L-Lactate is representative of the lactate secreted by our cells, as opposed to D-Lactate. Sodium L-lactate was used instead of lactic acid so only an increase in sodium ions rather than hydroxide was created, which would affect the pH controlled 3 L bioreactor vessel.

The experiment was executed in a 3 L glass bioreactor vessel at process temperature (37 C), controlled between 6.9-7.0 pH, using cell free chemically defined basal media, and Raman probes installed. The spiking solution used was the same chemically defined basal media formulation with 20 g/L of the sodium L-lactate solution added into the formulation to minimize the amount of dilution occurring with other components in the basal media.

Figure 6A:
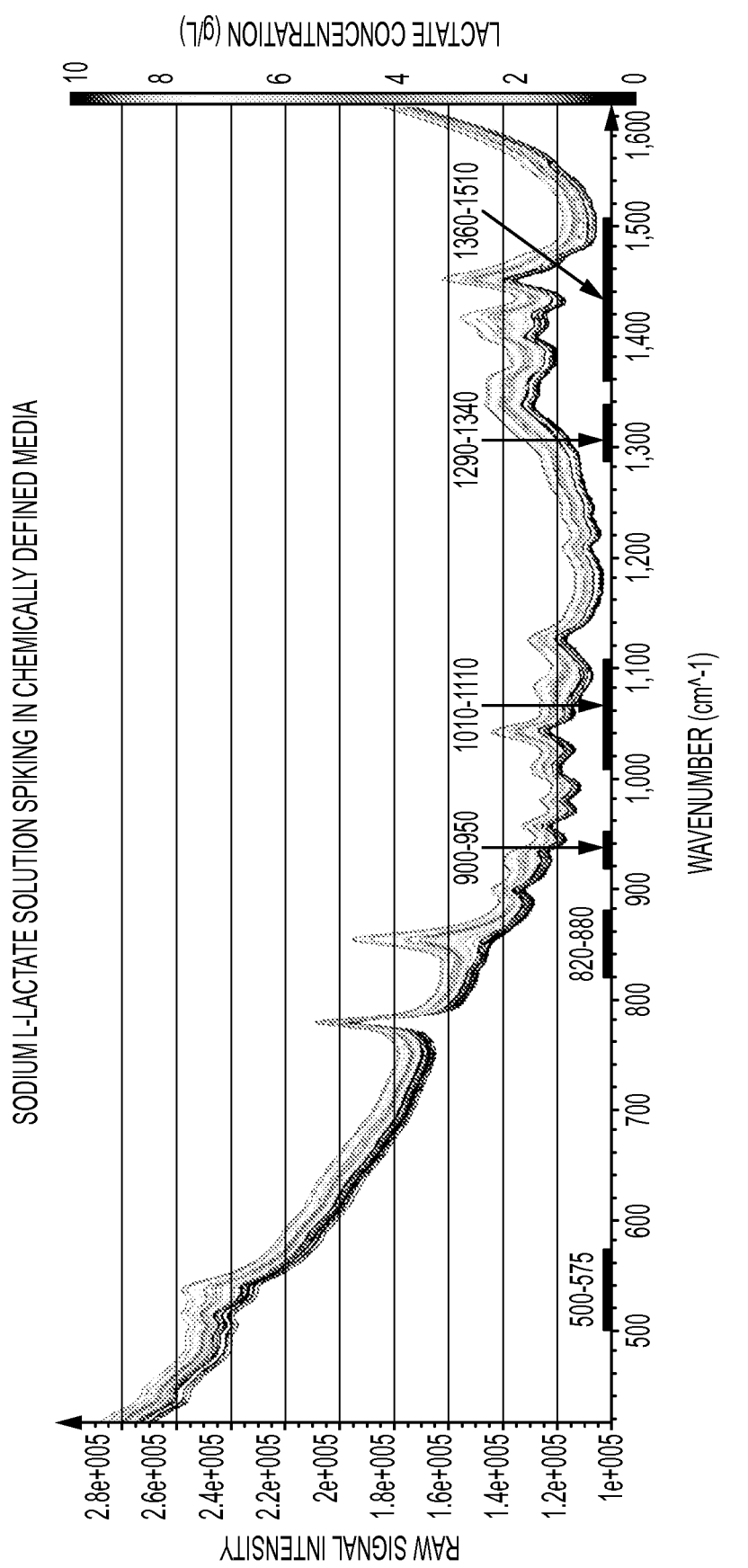
FIG. 6A is a non-limiting example of a raw Raman spectra of sodium L-lactate solution in chemically defined cell culture media zoomed in at the regions between 420-1600 wavenumber (cm-1), the following peaks are annotated: Peak 1 (500-575 cm-1), Peak 2 (820-880 cm-1), Peak 3 (900-950 cm-1), Peak 4 (1010-1110 cm-1), Peak 5 (1290-1340 cm-1), and Peak 6 (1360-1510 cm-1)
Figure 6B:
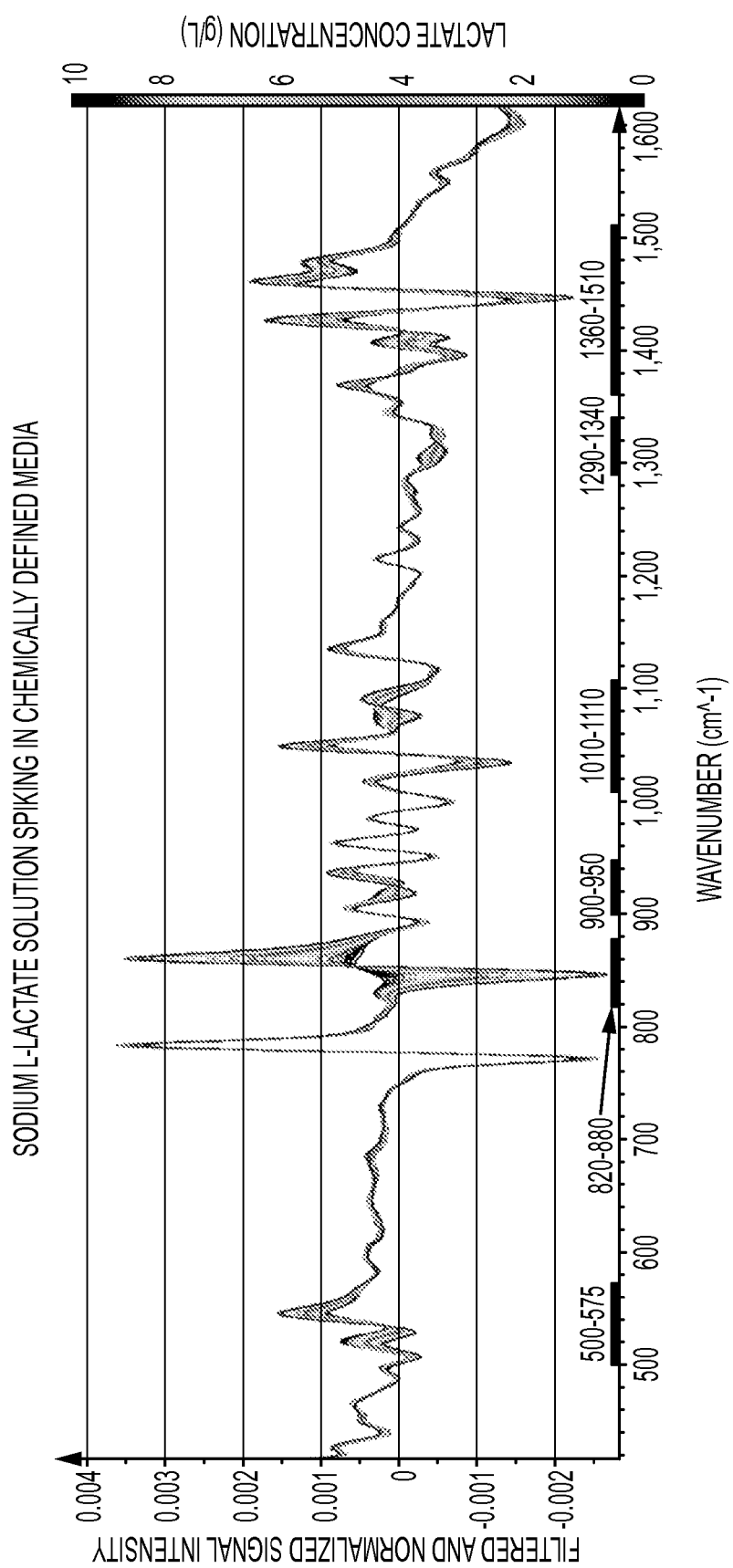
FIG. 6B is a non-limiting example of a signal processed and normalized Raman spectra of sodium L-lactate solution in chemically defined cell culture media zoomed in at the regions between 420-1600 wavenumber (cm-1), the following peaks are annotated: Peak 1 (500-575 cm-1), Peak 2 (820-880 cm-1), Peak 3 (900-950 cm-1), Peak 4 (1010-1110 cm-1), Peak 5 (1290-1340 cm-1), and Peak 6 (1360-1510 cm-1)
Figure 6C:
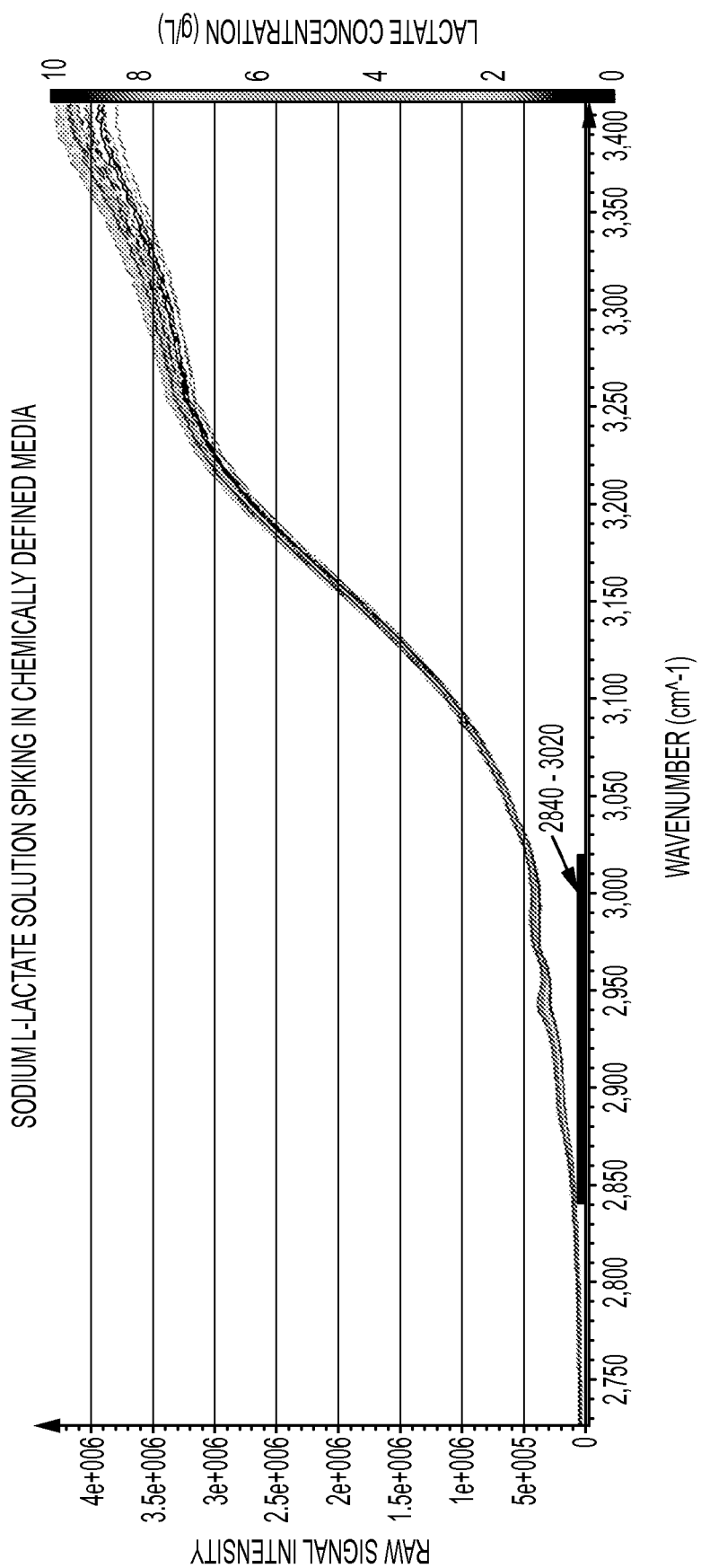
FIG. 6C is a non-limiting example of a raw Raman spectra of sodium L-lactate solution in chemically defined cell culture media zoomed in at the regions between & 2750-3400 wavenumber (cm-1), the following peak is annotated: Peak 7 (2840-3020 cm-1)
Figure 6D:
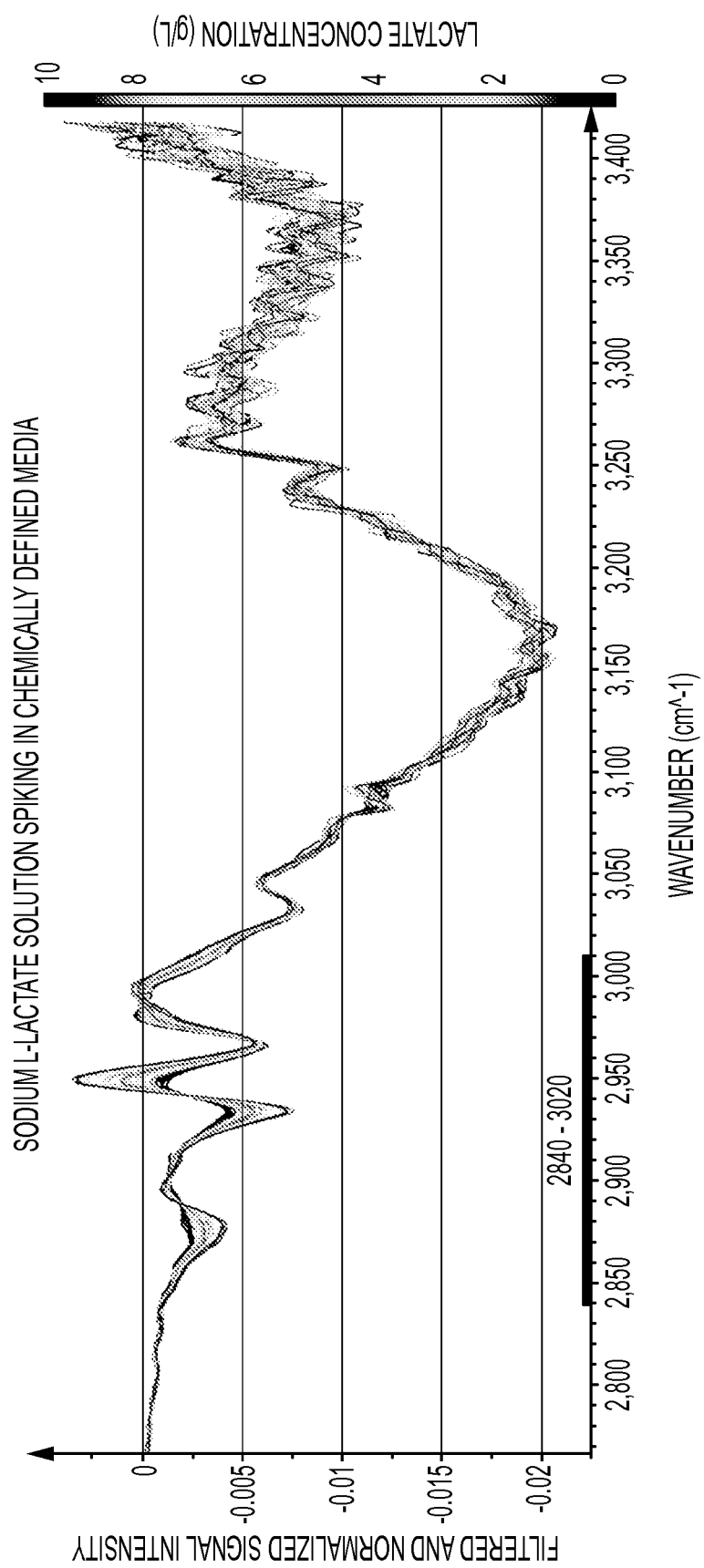
FIG. 6D is a is a non-limiting example of a signal processed and normalized Raman spectra of sodium L-lactate solution in chemically defined cell culture media zoomed in at the regions between 2750-3400 wavenumber (cm-1), the following peak is annotated: Peak 7 (2840-3020 cm-1).

Raw Raman spectra were collected between 420-1600 (cm-1) wavenumber (FIG. 6A), and between 2750-3400 (cm-1) wavenumber (FIG. 6C). The spectra were signal processed and normalized between 420-1600 (cm-1) wavenumber (FIG. 6B), and between 2750-3400 (cm-1) wavenumber (FIG. 6D).

Tables

TABLE 1

Summary of a PLS model calibration.
The column headers indicate different combinations of scale-specific calibration models. In the three cases where manufacturing data was built into calibration models, only two out of three batches were used to allow the use of one batch as a validation dataset, which allows for three possible combinations.

|  | Bench-scale | Pilot-scale | Bench + Pilot-scale | Bench + Pilot + MFG 1&2 | Bench + Pilot + MFG 1&3 | Bench + Pilot + MFG 2&3 |
|---|---|---|---|---|---|---|
| Number of Calibration Samples Used | | | | | | |
| Glucose | 226 | 142 | 475 | 569 | 560 | 592 |
| Lactate | 244 | 211 | 413 | 584 | 516 | 536 |
| Glutamate | 177 | 219 | 497 | 597 | 595 | 585 |
| Ammonium | 276 | 236 | 518 | 604 | 579 | 571 |
| Osmolality | 131 | 234 | 330 | 431 | 400 | 402 |
| VCD | 324 | 147 | 461 | 562 | 638 | 517 |
| TCD | 385 | 155 | 511 | 555 | 554 | 510 |
| Number of PLS Model Factors | | | | | | |
| Glucose | 4 | 3 | 5 | 4 | 5 | 5 |
| Lactate | 7 | 6 | 7 | 8 | 6 | 9 |
| Glutamate | 3 | 5 | 8 | 10 | 10 | 8 |

TABLE 1-continued

Summary of a PLS model calibration.
The column headers indicate different combinations of scale-specific calibration models. In the three cases where manufacturing data was built into calibration models, only two out of three batches were used to allow the use of one batch as a validation dataset, which allows for three possible combinations.

|  | Bench-scale | Pilot-scale | Bench + Pilot-scale | Bench + Pilot + MFG 1&2 | Bench + Pilot + MFG 1&3 | Bench + Pilot + MFG 2&3 |
|---|---|---|---|---|---|---|
| Ammonium | 8 | 8 | 8 | 7 | 9 | 9 |
| Osmolality | 6 | 4 | 5 | 5 | 6 | 7 |
| VCD | 3 | 3 | 4 | 4 | 4 | 4 |
| TCD | 5 | 4 | 5 | 3 | 3 | 3 |
| $R^2$ | | | | | | |
| Glucose | 0.942 | 0.936 | 0.926 | 0.875 | 0.918 | 0.903 |
| Lactate | 0.93 | 0.92 | 0.862 | 0.888 | 0.907 | 0.946 |
| Glutamate | 0.93 | 0.88 | 0.83 | 0.853 | 0.81 | 0.833 |
| Ammonium | 0.88 | 0.96 | 0.82 | 0.83 | 0.88 | 0.89 |
| Osmolality | 0.97 | 0.74 | 0.91 | 0.86 | 0.86 | 0.87 |
| VCD | 0.967 | 0.978 | 0.97 | 0.97 | 0.966 | 0.974 |
| TCD | 0.97 | 0.99 | 0.97 | 0.96 | 0.97 | 0.97 |
| $\sigma^2$ | | | | | | |
| Glucose | 0.93 | 0.927 | 0.917 | 0.869 | 0.909 | 0.892 |
| Lactate | 0.91 | 0.88 | 0.842 | 0.862 | 0.888 | 0.929 |
| Glutamate | 0.92 | 0.81 | 0.78 | 0.794 | 0.73 | 0.788 |
| Ammonium | 0.88 | 0.93 | 0.72 | 0.78 | 0.83 | 0.84 |
| Osmolality | 0.93 | 0.68 | 0.88 | 0.85 | 0.83 | 0.83 |
| VCD | 0.957 | 0.972 | 0.965 | 0.966 | 0.962 | 0.972 |
| TCD | 0.96 | 0.98 | 0.97 | 0.96 | 0.96 | 0.97 |

TABLE 2

Results of PLS model validation.
Manufacturing batch 3 was used as the validation batch for bench-scale only, pilot-scale only, and bench-scale + pilot-scale calibration data sets. The manufacturing validation batch used for calibration models is built with manufacturing-scale data is the batch not indicated in the column header.

|  | Bench-scale | Pilot-scale | Bench + Pilot-scale | Bench + Pilot + MFG 1&2 | Bench + Pilot + MFG 1&3 | Bench + Pilot + MFG 2&3 |
|---|---|---|---|---|---|---|
| Root Mean Square Error of Estimation (RMSEE) Bench-scale | | | | | | |
| Glucose (g/L) | 0.58 | 0.52 | 0.73 | 0.88 | 0.72 | 0.83 |
| Lactate (g/L) | 0.12 | 0.13 | 0.17 | 0.16 | 0.14 | 0.12 |
| Glutamate (mM) | 0.11 | 0.2 | 0.29 | 0.28 | 0.32 | 0.3 |
| Ammonium (mM) | 0.24 | 0.23 | 0.35 | 0.38 | 0.3 | 0.29 |
| Osmolality (mOsm/kg) | 8.25 | 15.92 | 11.24 | 13.93 | 12.91 | 12.81 |
| VCD ($\times 10^6$ vc/mL) | 1.55 | 1.3 | 1.46 | 1.48 | 1.58 | 1.3 |
| TCD ($\times 10^6$ tc/mL) | 1.86 | 1.13 | 1.64 | 1.78 | 1.72 | 1.48 |
| Root Mean Square Error of Cross Validation (RMSECV) Bench-scale | | | | | | |
| Glucose (g/L) | 0.65 | 0.55 | 0.78 | 0.88 | 0.77 | 0.89 |
| Lactate (g/L) | 0.14 | 0.18 | 0.17 | 0.18 | 0.16 | 0.14 |
| Glutamate (mM) | 0.12 | 0.27 | 0.33 | 0.34 | 0.39 | 0.34 |
| Ammonium (mM) | 0.29 | 0.35 | 0.45 | 0.46 | 0.38 | 0.37 |
| Osmolality (mOsm/kg) | 12.78 | 17.74 | 13.06 | 14.76 | 14.46 | 14.3 |
| VCD ($\times 10^6$ vc/mL) | 1.76 | 1.48 | 1.58 | 1.58 | 1.69 | 1.37 |
| TCD ($\times 10^6$ tc/mL) | 2.22 | 1.33 | 1.85 | 1.81 | 1.76 | 1.51 |
| Root Mean Square Error of Prediction (RMSEP) Bench-scale | | | | | | |
| Glucose (g/L) | 1.13 | 77 | 0.74 | 0.6 | 0.74 | 0.91 |
| Lactate (g/L) | 0.19 | 0.2 | 0.19 | 0.18 | 0.16 | 0.16 |

TABLE 2-continued

Results of PLS model validation.
Manufacturing batch 3 was used as the validation batch for bench-scale only,
pilot-scale only, and bench-scale + pilot-scale calibration data sets. The
manufacturing validation batch used for calibration models is built with manu-
facturing-scale data is the batch not indicated in the column header.

|  | Bench-scale | Pilot-scale | Bench + Pilot-scale | Bench + Pilot + MFG 1&2 | Bench + Pilot + MFG 1&3 | Bench + Pilot + MFG 2&3 |
|---|---|---|---|---|---|---|
| Glutamate (mM) | 1.18 | 0.41 | 0.57 | 0.33 | 0.34 | 0.32 |
| Ammonium (mM) | 1.21 | 1.07 | 0.55 | 0.47 | 0.32 | 0.42 |
| Osmolality (mOsm/kg) | 23.2 | 19.5 | 20.8 | 10.7 | 14.6 | 13.1 |
| VCD ($\times 10^6$ vc/mL) | 4.87 | 5.75 | 5.57 | 1.3 | 1.27 | 1.46 |
| TCD ($\times 10^6$ tc/mL) | 3.68 | 3.72 | 2.95 | 1.64 | 2.35 | 1.71 |
| Average % Error | | | | | | |
| Glucose | 10.73 | 7.14 | 6.57 | 5.94 | 6.1 | 9.3 |
| Lactate | 15.17 | 17.17 | 18.9 | 17.28 | 14.7 | 15.66 |
| Glutamate | 74.92 | 26.17 | 35.7 | 29.46 | 15.6 | 34.51 |
| Ammonium | 19.1 | 46.93 | 14.15 | 14.96 | 12.1 | 13.19 |
| Osmolality | 6.4 | 5.16 | 5.5 | 2.34 | 2.6 | 3.37 |
| VCD | 60.87 | 66.57 | 59.15 | 22.87 | 11.7 | 18.3 |
| TCD | 57.46 | 23.56 | 38.64 | 21.16 | 28.3 | 21.59 |

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, e.g., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method of assessing a bioreactor culture, the method comprising:
   (i) obtaining a Raman spectrum of a manufacturing-scale bioreactor culture using a probe configured inline with the bioreactor; and
   (ii) determining a culture parameter of the manufacturing-scale bioreactor culture using a multivariate partial least squares (PLS) model that relates the Raman spectrum to the culture parameter, wherein the model was developed based on one or more test bioreactor cultures;
   wherein the working volume of the manufacturing-scale bioreactor culture is in a range of 1,000 L to 100,000 L;
   wherein the working volumes of the one or more test bioreactor cultures are in a range of 0.1 L to 100 L;
   wherein the model was built from spectral data collected during fed-batch cell culture processing from the one or more test bioreactor cultures by exporting the data from one or more respective Raman probes; and
   wherein each of the one or more Raman probes is configured for obtaining a Raman spectrum of the respective bioreactor culture during cell growth.

2. The method of claim 1, wherein
   (i) the test bioreactor culture is in a range of 1 L to 5 L; and/or
   (ii) the test bioreactor culture is is in a range of 50 L to 100 L.

3. The method of claim 1, wherein the culture parameter is a level of glucose, glutamate, ammonia or lactate in the culture.

4. The method of claim 3, wherein
   (a) the culture parameter is a level of glucose, and wherein the model has:
      (i) a root mean square error of estimation in a range of 0.50 g/L to 1 g/L, and/or
      (ii) a root mean square error of cross validation in a range of 0.50 g/L to 1 g/L, and/or
      (iii) a root mean square error of prediction in a range of 0.50 g/L to 1.5 g/L, and/or
      (iv) an average percentage error of up to 10%;
   (b) the culture parameter is a level of lactate, and wherein the model has:
      (i) a root mean square error of estimation in a range of 0.10 g/L to 0.20 g/L, and/or
      (ii) a root mean square error of cross validation in a range of 0.10 g/L to 0.20 g/L, and/or
      (iii) a root mean square error of prediction in a range of 0.10 g/L to 0.20 g/L, and/or
      (iv) an average percentage error of up to 20%;
   (c) the culture parameter is a level of glutamate, and wherein the model has;
      (i) a root mean square error of estimation in a range of 0.10 mM to 0.20 mM, and/or
      (ii) a root mean square error of cross validation in a range of 0.10 mM to 0.40 mM, and/or
      (iii) a root mean square error of prediction in a range of 0.40 mM to 1.5 mM, and/or
      (iv) an average percentage error of up to 35%; or
   (d) the culture parameter is a level of ammonium, and wherein the model has:
      (i) a root mean square error of estimation in a range of 0.20 mM to 0.40 mM, and/or
      (ii) a root mean square error of cross validation in a range of 0.20 mM to 0.50 mM, and/or
      (iii) a root mean square error of prediction in a range of 0.40 mM to 1.5 mM, and/or
      (iv) an average percentage error of up to 20%.

5. The method of claim 1, wherein the culture parameter is the osmolality of the culture.

6. The method of claim 5, wherein the model has:
   (i) a root mean square error of estimation in a range of 5 mOsm/kg to 15 mOsm/kg, and/or
   (ii) a root mean square error of cross validation in a range of 10 mOsm/kg to 15 mOsm/kg, and/or
   (iii) a root mean square error of prediction in a range of 10 mOsm/kg to 25 mOsm/kg, and/or
   (iv) an average percentage error of up to 10%.

7. The method of claim 1, wherein the volume of the manufacturing-scale bioreactor culture is in a range of 2000 L to 20000 L.

8. The method of claim 1, wherein the volume of the manufacturing-scale bioreactor culture is in a range of 2000 L to 15000 L.

9. A method comprising:
   (i) obtaining a Raman spectrum of a first bioreactor culture of a first volume using a probe configured inline with the bioreactor; and
   (ii) determining a culture parameter of the first bioreactor culture using a multivariate partial least squares (PLS) model, which model was developed based on a second bioreactor culture of a second volume, that relates the Raman spectrum to the culture parameter, wherein the second volume is in a range of 0.1% to 10% of the first volume;
   wherein the model was built from spectral data collected during fed-batch cell culture processing from the one or more test bioreactor cultures by exporting the data from one or more respective Raman probes; and
   wherein each of the one or more Raman probes is configured for obtaining a Raman spectrum of the respective bioreactor culture during cell growth.

10. The method of claim 1, wherein the model was further developed based on at least one bioreactor culture of substantially the same volume as the manufacturing-scale bioreactor culture.

11. The method of claim 1, wherein
(i) the Raman spectrum comprises spectral signal in the 200cm$^{-1}$ to 3400cm$^{-1}$ wavenumber range;
(ii) the Raman spectrum comprises spectral signal in the visible, near infrared, infrared, near ultraviolet, or ultraviolet (UV) range;
(iii) the Raman spectrum is obtained using Surface Enhanced Raman Spectroscopy (SERS), resonance Raman spectroscopy, tip-enhanced Raman spectroscopy, polarized Raman spectroscopy, stimulated Raman spectroscopy, transmission Raman spectroscopy, spatially offset Raman spectroscopy, difference Raman spectroscopy, Fourier Transform (FT) Raman spectroscopy, or hyper Raman spectroscopy; and/or
(iv) the Raman spectrum is obtained using a Raman analyzer configured with a laser or other suitable light source configured to operate at wavelengths in a range of 325 nm to 1064 nm.

12. A bioreactor system comprising:
a bioreactor chamber configured for containing a manufacturing-scale bioreactor culture;
a probe configured for obtaining a Raman spectrum of the manufacturing-scale bioreactor culture; and
a computer configured for determining a culture parameter of the manufacturing-scale bioreactor culture, wherein the computer comprises:
an input interface configured to receive information indicative of the Raman spectrum obtained from the probe;
at least one processor programmed to evaluate a model that relates the Raman spectrum to the culture parameter, wherein the model was developed based on one or more test bioreactor cultures, and
an output interface configured to output a signal indicative of the determined culture parameter;
wherein the working volume of the manufacturing-scale bioreactor culture is in a range of 1,000 L to 100,000 L;
wherein the working volumes of the one or more test bioreactor cultures are in a range of 0.1 L to 100 L;
wherein the model was built from spectral data collected during fed-batch cell culture processing from the one or more test bioreactor cultures by exporting the data from one or more respective Raman probes; and
wherein each of the one or more Raman probes is configured for obtaining a Raman spectrum of the respective bioreactor culture during cell growth.

13. The bioreactor system of claim 12, wherein the output comprises a feedback control signal for controlling operation of a device for altering the culture parameter or wherein the device for altering the culture parameter is a pump or valve configured to control flow, into or out from the bioreactor culture, of a medium comprising one or more culture components.

14. The bioreactor system of claim 12, wherein
(i) the test bioreactor culture is in a range of 1 L to 5 L; and/or
(ii) the test bioreactor culture is in a range of 50 L to 100 L; and/or
(v) the model is a partial least squares model.

15. The bioreactor system claim 12, wherein the culture parameter is a level of glucose, glutamate, ammonia or lactate in the culture, or wherein the culture parameter is the osmolality of the culture.

16. The bioreactor system of claim 12, wherein
(a) the culture parameter is a level of glucose, and wherein the model has:
(i) a root mean square error of estimation in a range of 0.50 g/L to 1 g/L, and/or
(ii) a root mean square error of cross validation in a range of 0.50 g/L to 1 g/L, and/or
(iii) a root mean square error of prediction in a range of 0.50 g/L to 1.5 g/L, and/or
(iv) an average percentage error of up to 10%;
(b) the culture parameter is a level of lactate, and wherein the model has:
(i) a root mean square error of estimation in a range of 0.10 g/L to 0.20 g/L, and/or
(ii) a root mean square error of cross validation in a range of 0.10 g/L to 0.20 g/L, and/or
(iii) a root mean square error of prediction in a range of 0.10 g/L to 0.20 g/L, and/or
(iv) an average percentage error of up to 20%;
(c) the culture parameter is a level of glutamate, and wherein the model has
(i) a root mean square error of estimation in a range of 0.10 mM to 0.20 mM, and/or
(ii) a root mean square error of cross validation in a range of 0.10 mM to 0.40 mM, and/or
(iii) a root mean square error of prediction in a range of 0.40 mM to 1.5 mM, and/or
(iv) an average percentage error of up to 35%; and/or
(d) the culture parameter is a level of ammonium, and wherein the model has:
(i) a root mean square error of estimation in a range of 0.20 mM to 0.40 mM, and/or
(ii) a root mean square error of cross validation in a range of 0.20 mM to 0.50 mM, and/or
(iii) a root mean square error of prediction in a range of 0.40 mM to 1.5 mM, and/or
(iv) an average percentage error of up to 20%.

17. The bioreactor system of claim 12, wherein the culture parameter is the osmolality of the culture and the model has:
(i) a root mean square error of estimation in a range of 5 mOsm/kg to 15 mOsm/kg, and/or
(ii) a root mean square error of cross validation in a range of 10 mOsm/kg to 15 mOsm/kg, and/or
(iii) a root mean square error of prediction in a range of 10 mOsm/kg to 25 mOsm/kg, and/or
(iv) an average percentage error of up to 10%.

18. The bioreactor system of claim 12, wherein
(i) the Raman spectrum comprises spectral signal in the 200cm$^{-1}$ to 3400cm-1 wavenumber range;
(ii) the Raman spectrum comprises spectral signal in the visible, near infrared, infrared, near ultraviolet, or ultraviolet (UV) range;
(iii) the Raman spectrum is obtained using Surface Enhanced Raman Spectroscopy (SERS), resonance Raman spectroscopy, tip-enhanced Raman spectroscopy, polarized Raman spectroscopy, stimulated Raman spectroscopy, transmission Raman spectroscopy, spatially offset Raman spectroscopy, difference Raman spectroscopy, Fourier Transform (FT) Raman spectroscopy, or hyper Raman spectroscopy; and/or
(iv) the probe comprises a Raman analyzer configured with a laser or other suitable light source configured to operate at wavelengths in a range of 325 nm to 1064 nm.

19. The bioreactor system of claim 12, wherein the model was further developed based on at least one bioreactor culture of substantially the same volume as the manufacturing-scale bioreactor culture.

20. The method of claim 12, wherein the volume of the manufacturing-scale bioreactor culture is in a range of 2000 L to 20000 L.

21. The method of claim 12, wherein the volume of the manufacturing-scale bioreactor culture is in a range of 2000 L to 15000 L.

* * * * *

UNITED STATES PATENT AND TRADEMARK OFFICE
CERTIFICATE OF CORRECTION

PATENT NO. : 10,563,163 B2  
APPLICATION NO. : 15/322560  
DATED : February 18, 2020  
INVENTOR(S) : Brandon Berry et al.

Page 1 of 2

It is certified that error appears in the above-identified patent and that said Letters Patent is hereby corrected as shown below:

In the Claims

Claim 2, Column 37, Lines 53-54, the text:
"(ii) the test bioreactor culture is is in a range of 50 L to 100 L."
Should read:
--(ii) the test bioreactor culture is in a range of 50 L to 100 L.--

Claim 4, Column 38, Lines 10-11, the text:
"(c) the culture parameter is a level of glutamate, and wherein the model has;"
Should read:
--(c) the culture parameter is a level of glutamate, and wherein the model has:--

Claim 11, Column 39, Lines 2-3, the text:
"(i) the Raman spectrum comprises spectral signal in the 200cm-$^1$ to 3400cm-$^1$ wavenumber range;"
Should read:
--(i) the Raman spectrum comprises spectral signal in the 200cm$^{-1}$ to 3400cm$^{-1}$ wavenumber range;--

Claim 13, Column 39, Lines 48-54, the text:
"13. The bioreactor system of claim 12, wherein the output comprises a feedback control signal for controlling operation of a device for altering the culture parameter or wherein the device for altering the culture parameter is a pump or valve configured to control flow, into or out from the bioreactor culture, of a medium comprising one or more culture components."
Should read:
--13. The bioreactor system of claim 12, wherein the output comprises a feedback control signal for controlling operation of a device for altering the culture parameter, wherein the device for altering the culture parameter is a pump or valve configured to control flow, into or out from the bioreactor culture, of a medium comprising one or more culture components.--

Signed and Sealed this  
Twenty-first Day of July, 2020

Andrei Iancu  
*Director of the United States Patent and Trademark Office*

Claim 14, Column 39, Lines 58-60, the text:
"(ii) the test bioreactor culture is in a range of 50 L to 100 L; and/or
(v) the model is a partial least squares model."
Should read:
--(ii) the test bioreactor culture is in a range of 50 L to 100 L.--

Claim 18, Column 40, Lines 47-48, the text:
"(i) the Raman spectrum comprises spectral signal in the $200 cm^{-1}$ to $3400 cm^{-1}$ wavenumber range;"
Should read:
--(i) the Raman spectrum comprises spectral signal in the $200 cm^{-1}$ to $3400 cm^{-1}$ wavenumber range;--